United States Patent
Karmarkar et al.

(10) Patent No.: US 10,492,881 B2
(45) Date of Patent: *Dec. 3, 2019

(54) SURGICAL IMAGE-GUIDED NAVIGATION DEVICES AND RELATED SYSTEMS

(71) Applicant: MRI Interventions, Inc., Irvine, CA (US)

(72) Inventors: Parag V. Karmarkar, Columbia, MD (US); Kimble Jenkins, Memphis, TN (US)

(73) Assignee: MRI Interventions, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/492,747

(22) Filed: Apr. 20, 2017

(65) Prior Publication Data
US 2017/0215981 A1 Aug. 3, 2017

Related U.S. Application Data

(63) Continuation of application No. 14/693,456, filed on Apr. 22, 2015, now Pat. No. 9,763,745, which is a
(Continued)

(51) Int. Cl.
*A61B 5/05* (2006.01)
*A61B 90/11* (2016.01)
(Continued)

(52) U.S. Cl.
CPC ............ *A61B 90/11* (2016.02); *A61B 5/0476* (2013.01); *A61B 5/055* (2013.01); *A61B 5/6847* (2013.01);
(Continued)

(58) Field of Classification Search
CPC . A61B 2034/2051; A61B 34/20; A61B 5/055; A61B 90/11; A61B 2017/00039;
(Continued)

(56) References Cited

U.S. PATENT DOCUMENTS 2,697,433 A 12/1954 Zehnder
4,051,845 A 10/1977 Collins
(Continued)

FOREIGN PATENT DOCUMENTS

DE 19625834 1/1998
DE 10029736 3/2002
(Continued)

OTHER PUBLICATIONS

Dorward et al., Accuracy of true frameless stereotaxy: in vivo measurement and laboratory phantom studies, J. Neurosurg., 1999, 90:160-168.
(Continued)

*Primary Examiner* — Christopher L Cook
(74) *Attorney, Agent, or Firm* — Myers Bigel, P.A.

(57) ABSTRACT

MRI compatible localization and/or guidance systems for facilitating placement of an interventional therapy and/or device in vivo include: (a) a mount adapted for fixation to a patient; (b) a targeting cannula with a lumen configured to attach to the mount so as to be able to controllably translate in at least three dimensions; and (c) an elongate probe configured to snugly slidably advance and retract in the targeting cannula lumen, the elongate probe comprising at least one of a stimulation or recording electrode. In operation, the targeting cannula can be aligned with a first trajectory and positionally adjusted to provide a desired internal access path to a target location with a corresponding trajectory for the elongate probe. Automated systems for determining an MR scan plane associated with a trajectory and for determining mount adjustments are also described.

20 Claims, 32 Drawing Sheets

Related U.S. Application Data continuation of application No. 12/066,862, filed as application No. PCT/US2006/045752 on Nov. 29, 2006, now Pat. No. 9,042,958.

(60) Provisional application No. 60/740,353, filed on Nov. 29, 2005.

(51) Int. Cl.

| | | |
|---|---|---|
| *A61B 5/0476* | (2006.01) | |
| *A61B 5/055* | (2006.01) | |
| *A61B 5/00* | (2006.01) | |
| *A61N 1/05* | (2006.01) | |
| *G01R 33/28* | (2006.01) | |
| *G01R 33/34* | (2006.01) | |
| *A61B 34/20* | (2016.01) | |
| *A61B 34/10* | (2016.01) | |
| *A61B 90/14* | (2016.01) | |
| *A61M 39/08* | (2006.01) | |
| *A61N 1/08* | (2006.01) | |
| *A61B 17/00* | (2006.01) | |
| *A61N 1/37* | (2006.01) | |
| *G01R 33/48* | (2006.01) | |
| *A61N 1/372* | (2006.01) | |
| *A61B 90/00* | (2016.01) | |

(52) U.S. Cl.
CPC .......... *A61B 5/6864* (2013.01); *A61B 5/6865* (2013.01); *A61B 5/7435* (2013.01); *A61B 34/10* (2016.02); *A61B 34/20* (2016.02); *A61B 90/14* (2016.02); *A61M 39/08* (2013.01); *A61N 1/0529* (2013.01); *A61N 1/0534* (2013.01); *A61N 1/0539* (2013.01); *A61N 1/08* (2013.01); *G01R 33/285* (2013.01); *G01R 33/286* (2013.01); *G01R 33/287* (2013.01); *G01R 33/34084* (2013.01); *A61B 2017/00039* (2013.01); *A61B 2034/107* (2016.02); *A61B 2034/2051* (2016.02); *A61B 2090/374* (2016.02); *A61B 2090/3954* (2016.02); *A61N 1/086* (2017.08); *A61N 1/372* (2013.01); *A61N 1/3718* (2013.01); *G01R 33/288* (2013.01); *G01R 33/4808* (2013.01)

(58) Field of Classification Search
CPC ...... A61B 2090/374; A61B 2090/3954; A61B 5/0476; A61B 5/6847; A61B 5/6864; A61B 5/6865; A61B 5/7435; A61B 19/5244; A61B 2034/107; A61B 34/10; A61B 90/14

See application file for complete search history.

(56) References Cited

U.S. PATENT DOCUMENTS

| | | |
|---|---|---|
| 4,209,258 A | 6/1980 | Oakes |
| 4,276,697 A | 7/1981 | Drake et al. |
| 4,319,136 A | 3/1982 | Jinkins |
| 4,386,602 A | 6/1983 | Sheldon et al. |
| 4,826,487 A * | 5/1989 | Winter .................. A61B 90/11 604/175 |
| 4,838,265 A | 6/1989 | Cosman et al. |
| 4,922,915 A | 5/1990 | Arnold et al. |
| 5,052,035 A | 9/1991 | Krupnick |
| 5,125,888 A | 6/1992 | Howard et al. |
| 5,154,179 A | 10/1992 | Ratner |
| 5,154,723 A | 10/1992 | Kubota et al. |
| 5,201,742 A | 4/1993 | Hasson |
| 5,260,985 A | 11/1993 | Mosby |
| 5,342,356 A | 8/1994 | Ellman et al. |
| 5,427,099 A | 6/1995 | Adams |
| 5,469,847 A | 11/1995 | Zinreich et al. |
| 5,638,819 A | 6/1997 | Manwaring |
| 5,655,084 A | 8/1997 | Pinsky et al. |
| 5,695,501 A | 12/1997 | Carol et al. |
| 5,697,958 A | 12/1997 | Paul et al. |
| 5,699,801 A | 12/1997 | Atalar et al. |
| 5,707,335 A | 1/1998 | Howard et al. |
| 5,728,079 A | 3/1998 | Webber et al. |
| 5,743,899 A | 4/1998 | Zinreich |
| 5,776,144 A | 7/1998 | Leysieffer et al. |
| 5,779,694 A | 7/1998 | Howard et al. |
| 5,800,353 A | 9/1998 | McLaurin, Jr. |
| 5,817,017 A | 10/1998 | Young et al. |
| 5,855,582 A | 1/1999 | Gildenberg |
| 5,873,822 A | 2/1999 | Ferre et al. |
| 5,928,145 A | 7/1999 | Ocali et al. |
| 5,961,455 A | 10/1999 | Daum et al. |
| 5,971,984 A | 10/1999 | Taylor et al. |
| 5,993,463 A | 11/1999 | Truwit |
| 6,006,126 A | 12/1999 | Cosman |
| 6,050,992 A | 4/2000 | Nichols |
| 6,052,477 A | 4/2000 | Wang et al. |
| 6,119,032 A | 9/2000 | Martin et al. |
| 6,159,497 A | 12/2000 | LaPrade et al. |
| 6,167,292 A | 12/2000 | Badano et al. |
| 6,167,311 A | 12/2000 | Rezai |
| 6,195,577 B1 | 2/2001 | Truwit et al. |
| 6,206,890 B1 | 3/2001 | Truwit |
| 6,216,030 B1 | 4/2001 | Howard et al. |
| 6,263,229 B1 | 7/2001 | Atalar et al. |
| 6,264,607 B1 | 7/2001 | Goll et al. |
| 6,267,769 B1 | 7/2001 | Truwit et al. |
| 6,267,770 B1 | 7/2001 | Truwit |
| 6,273,896 B1 | 8/2001 | Franck et al. |
| 6,282,437 B1 | 8/2001 | Franck et al. |
| 6,284,971 B1 | 9/2001 | Atalar et al. |
| 6,298,262 B1 | 10/2001 | Franck et al. |
| 6,351,573 B1 | 2/2002 | Schneider |
| 6,351,662 B1 | 2/2002 | Franck et al. |
| 6,356,786 B1 | 3/2002 | Rezai et al. |
| 6,368,329 B1 | 4/2002 | Truwit |
| 6,405,079 B1 | 6/2002 | Ansarinia |
| 6,419,680 B1 | 7/2002 | Cosman et al. |
| 6,438,423 B1 | 8/2002 | Rezai et al. |
| 6,526,318 B1 | 2/2003 | Ansarinia |
| 6,529,765 B1 | 3/2003 | Franck et al. |
| 6,539,263 B1 | 3/2003 | Schiff et al. |
| 6,546,277 B1 | 4/2003 | Franck et al. |
| 6,574,497 B1 | 6/2003 | Pacetti |
| 6,584,351 B1 | 6/2003 | Ekwall |
| 6,591,128 B1 | 7/2003 | Wu et al. |
| 6,606,513 B2 | 8/2003 | Lardo et al. |
| 6,609,030 B1 | 8/2003 | Rezai et al. |
| 6,628,980 B2 | 9/2003 | Atalar et al. |
| 6,675,033 B1 | 1/2004 | Lardo et al. |
| 6,701,176 B1 | 3/2004 | Halperin et al. |
| 6,708,064 B2 | 3/2004 | Rezai |
| 6,725,080 B2 | 4/2004 | Melkent et al. |
| 6,725,092 B2 | 4/2004 | MacDonald et al. |
| 6,752,812 B1 | 6/2004 | Truwit |
| 6,772,000 B2 | 8/2004 | Talpade |
| 6,782,288 B2 | 8/2004 | Truwit et al. |
| 6,902,569 B2 | 6/2005 | Parmer et al. |
| 6,904,307 B2 | 6/2005 | Karmarkar et al. |
| 6,920,347 B2 | 7/2005 | Simon et al. |
| 7,022,082 B2 | 4/2006 | Sonek |
| 7,155,316 B2 | 12/2006 | Sutherland et al. |
| 7,167,760 B2 | 1/2007 | Dawant et al. |
| 7,174,219 B2 | 2/2007 | Wahlstrand et al. |
| 7,203,551 B2 | 4/2007 | Houben et al. |
| 7,204,840 B2 | 4/2007 | Skakoon et al. |
| 7,212,611 B2 | 5/2007 | De Godzinsky |
| 7,217,276 B2 | 5/2007 | Henderson et al. |
| 7,235,084 B2 | 6/2007 | Skakoon et al. |
| 7,241,283 B2 | 7/2007 | Putz |
| 7,313,430 B2 | 12/2007 | Urquhart et al. |
| 7,559,935 B2 | 7/2009 | Solar et al. |
| 7,561,906 B2 | 7/2009 | Atalar et al. |

(56) References Cited

U.S. PATENT DOCUMENTS

| | | | |
|---|---|---|---|
| 7,637,915 | B2 | 12/2009 | Parmer et al. |
| 7,658,879 | B2 | 2/2010 | Solar |
| 7,660,621 | B2 | 2/2010 | Skakoon et al. |
| 7,697,972 | B2 | 4/2010 | Verard et al. |
| 7,699,854 | B2 | 4/2010 | Mazzocchi et al. |
| 7,792,568 | B2 | 9/2010 | Zhong et al. |
| 7,794,469 | B2 | 9/2010 | Kao et al. |
| 7,896,889 | B2 | 3/2011 | Mazzocchi et al. |
| 7,955,385 | B2 | 6/2011 | Crittenden |
| 8,128,577 | B2 | 3/2012 | Viola |
| 2001/0004676 | A1 | 6/2001 | Ouchi |
| 2001/0047126 | A1 | 11/2001 | Nagai et al. |
| 2001/0053879 | A1 | 12/2001 | Mills et al. |
| 2002/0019641 | A1 | 2/2002 | Truwit |
| 2002/0049451 | A1 | 4/2002 | Parmer et al. |
| 2002/0052610 | A1 | 5/2002 | Skakoon et al. |
| 2002/0082495 | A1 | 6/2002 | Biswal et al. |
| 2003/0009095 | A1 | 1/2003 | Skarda |
| 2003/0028095 | A1 | 2/2003 | Tulley et al. |
| 2003/0050557 | A1 | 3/2003 | Susil et al. |
| 2003/0055436 | A1 | 3/2003 | Daum et al. |
| 2003/0055449 | A1 | 3/2003 | Lee et al. |
| 2003/0097116 | A1 | 5/2003 | Putz |
| 2003/0120143 | A1 | 6/2003 | Franklin et al. |
| 2003/0205233 | A1 | 11/2003 | Aboul-Hosn et al. |
| 2004/0002642 | A1 | 1/2004 | Dekel et al. |
| 2004/0024308 | A1 | 2/2004 | Wickline et al. |
| 2004/0044279 | A1 | 3/2004 | Lewin et al. |
| 2004/0046557 | A1 | 3/2004 | Karmarkar et al. |
| 2004/0064148 | A1 | 4/2004 | Daum et al. |
| 2004/0092810 | A1 | 5/2004 | Daum et al. |
| 2004/0122446 | A1 | 6/2004 | Solar |
| 2004/0167393 | A1 | 8/2004 | Solar et al. |
| 2004/0167542 | A1 | 8/2004 | Solar et al. |
| 2004/0167543 | A1 | 8/2004 | Mazzocchi et al. |
| 2004/0215279 | A1 | 10/2004 | Houben et al. |
| 2004/0228796 | A1 | 11/2004 | Talpade |
| 2005/0004453 | A1 | 1/2005 | Tearney et al. |
| 2005/0058363 | A1 | 3/2005 | Florent et al. |
| 2005/0070781 | A1 | 3/2005 | Dawant et al. |
| 2005/0131522 | A1 | 6/2005 | Stinson et al. |
| 2005/0165301 | A1 | 7/2005 | Smith et al. |
| 2005/0171425 | A1 | 8/2005 | Burke |
| 2005/0193609 | A1 | 9/2005 | Schwartz |
| 2005/0203384 | A1 | 9/2005 | Sati et al. |
| 2005/0255046 | A1 | 11/2005 | Zhong et al. |
| 2006/0173283 | A1 | 8/2006 | Axelsson et al. |
| 2006/0195119 | A1 | 8/2006 | Mazzocchi et al. |
| 2006/0229641 | A1 | 10/2006 | Gupta et al. |
| 2006/0241368 | A1 | 10/2006 | Fichtinger et al. |
| 2006/0241400 | A1 | 10/2006 | Bucholz |
| 2006/0252314 | A1 | 11/2006 | Atalar et al. |
| 2007/0106305 | A1 | 5/2007 | Kao et al. |
| 2008/0039709 | A1 | 2/2008 | Karmarkar |

FOREIGN PATENT DOCUMENTS

| | | |
|---|---|---|
| DE | 10029737 | 5/2003 |
| EP | 1524626 | 4/2005 |
| WO | WO 1998/52064 | 11/1998 |
| WO | WO 99/034732 | 7/1999 |
| WO | WO 02/43003 | 5/2002 |
| WO | WO 2003/102614 | 12/2003 |
| WO | WO 2004/029782 | 4/2004 |
| WO | WO 2004/058086 | 7/2004 |
| WO | PCT/US/2005/026508 | 4/2005 |
| WO | WO 2006/081409 | 8/2006 |
| WO | WO 2006/099475 | 9/2006 |
| WO | WO 2007/047966 | 4/2007 |
| WO | WO 2007/106558 | 9/2007 |

OTHER PUBLICATIONS

Fitzpatrick, et al., Accuracy of Customized Miniature Stereotactic Platforms, abstract only, Stereotactic and Functional Neurosurgery, vol. 83, No. 1, 2005, http://content.karger.com, 2 sheets.

Francel, NEXFRAME System, Bilateral Activa Lead Delivery to STN Using NEXFRAME, Oklahoma University Presbyterian Hospital, Image-Guided Neurolgics, 2 Pages, 2004.

Franck, et al., STarFix™, Power Point presentation, www.tgt.vanderbilt.edu/reu2/REU2002/chris.ppt, 2002, 19 Sheets.

Grimson et al., An automatic registration method for frameless stereotaxy, image guided surgery, and visualization, IEEE Tran on Medical Imaging, Apr. 1996, 129-140.

Hall et al., Brian biopsy sampling by using prospective stereotaxis and a trajectory guide, J. Neurosurg., 2001, 94:67-71.

International Search Report and Written Opinion for corresponding PCT application No. PCT/US2008/011050, dated Jun. 24, 2009.

International Search Report and Written Opinion of the International Searching Authority for PCT Application No. PCT/US2006/045752, dated Sep. 28, 2007.

Invitation to Pay Additional Fees and Partial International Search for PCT application PCT/US2008/007169, dated Nov. 19, 2008.

Invitation to Pay Additional Fees and Partial Search for corresponding PCT Application No. PCT/US2008/011050, dated Mar. 10, 2009.

Lin, Fa-Hsuan et al., A Wavelet-Based Approximation of Surface Coil Sensitivity Profiles for Correction of Image Intensity Inhomogeneity and Parallel Imaging Reconstruction, Human Brain Mapping, vol. 19, No. 2, pp. 96-111, (2003).

Liu et al., Remotely-Controlled Approach for Stereotactic Neurobiopsy, Computer Aided Surgery, 2002, 7:237-247.

Martin et al, Placement of Deep Brain Stimulator Electrodes Using Real-Time High-Field Interventional Magnetic Resonance Imaging, Magnetic Resonance in Medicine, 2005, 54: 1107-1114.

Singh, Manbir and Moriel NessAiver, Accurate Intensity Correction for Endorectal Surface Coil MR Imaging of the Prostate, IEEE Transactions on Nuclear Science, vol. 40, No. 4, pp. 1307-1309, (1993).

Smith et al., The Neurostation—A Highly Accurate, Minimally Invasive Solution to Frameless Stereotactic Neurosurgery, Computerized Medical Imaging and Graphics, 1994, 247-256, 18(4).

Truwit et al., Prospective Stereotaxy: A Novel Method of Trajectory Alignment Using Real-Time Image Guidance, J. Magn. Reson. Imag., 2001, 13:452-457.

Willems, et al., Frameless Stereotaxy, VHL Family Alliance, http://www.vhl.org/newsletter/vhl2000/00aefrst.htm, Mar. 2000, 3 Sheets.

Wirtz et al., Image-Guided Neurosurgery with Intraoperative MRI: Update of Frameless Stereotaxy and Radicality Control, Sterotact Funct Neurosurg 1997, 68:39-43.

* cited by examiner

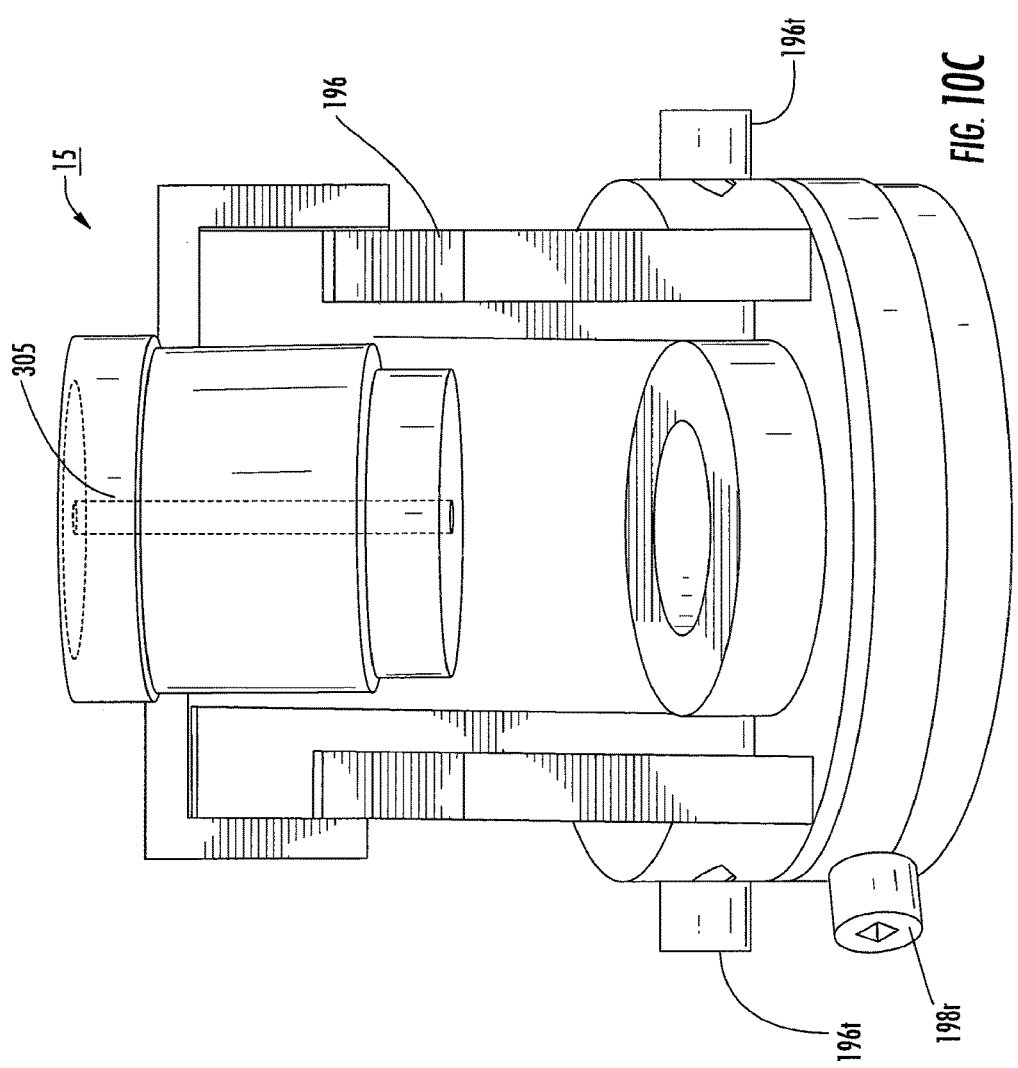

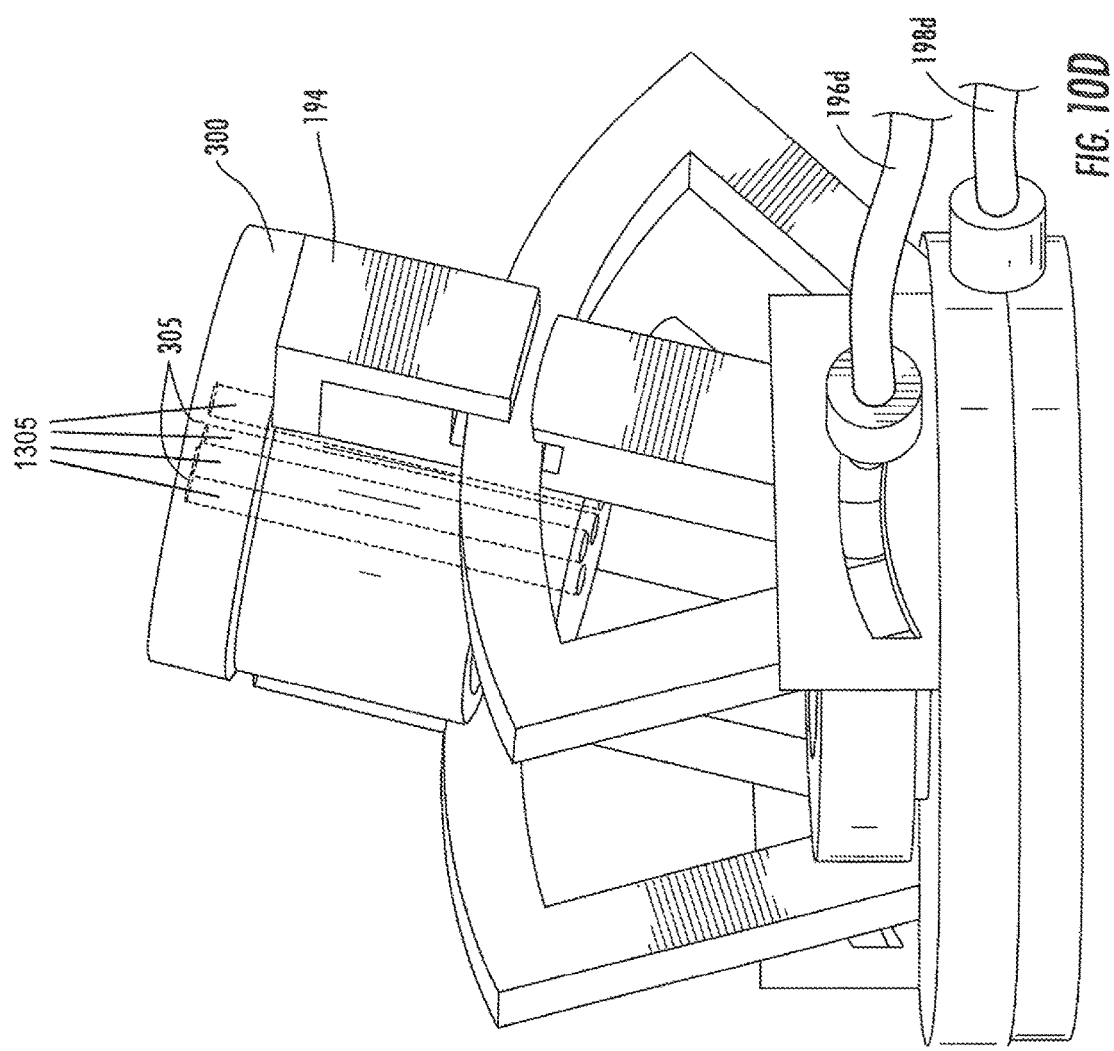

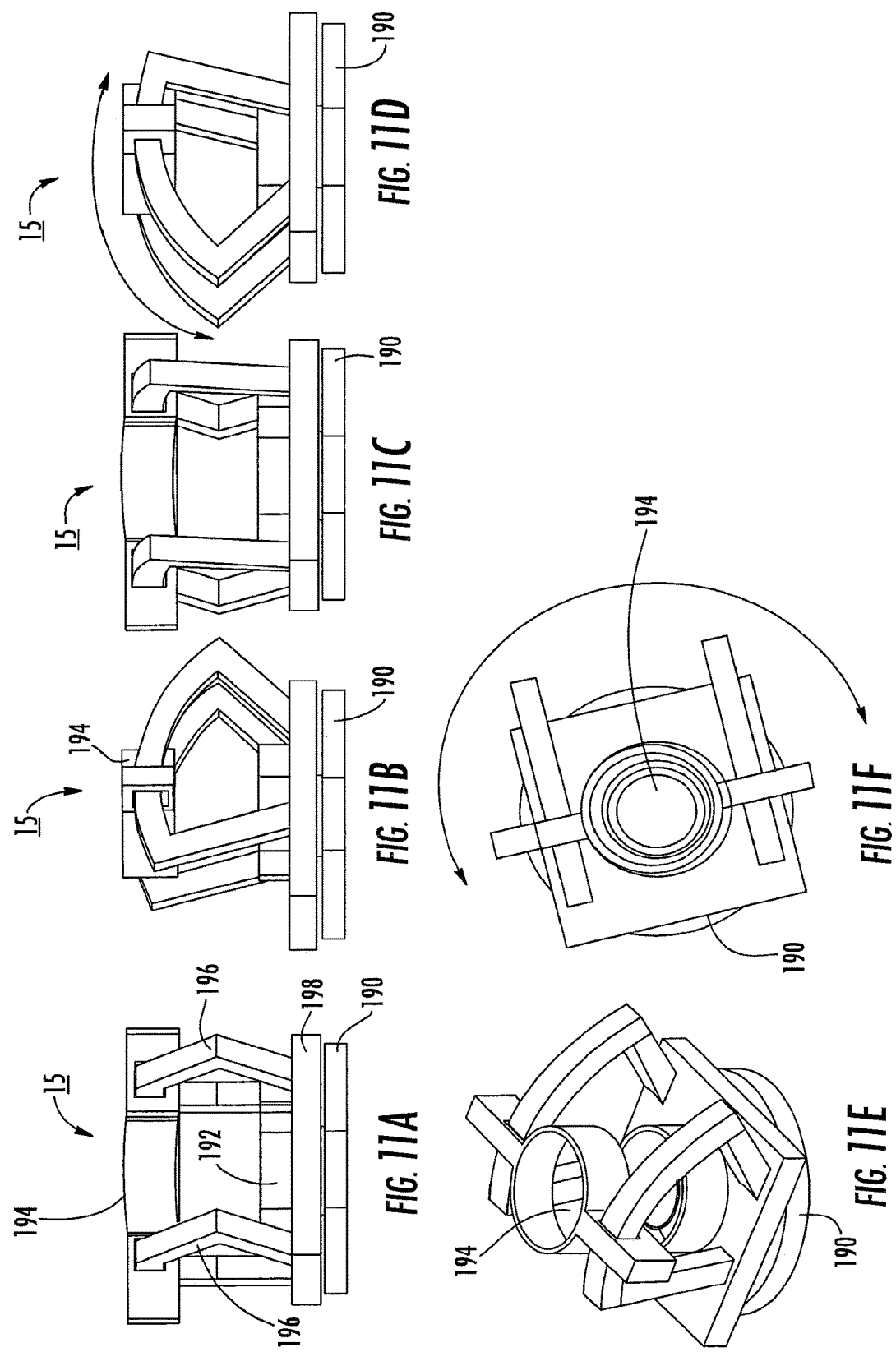

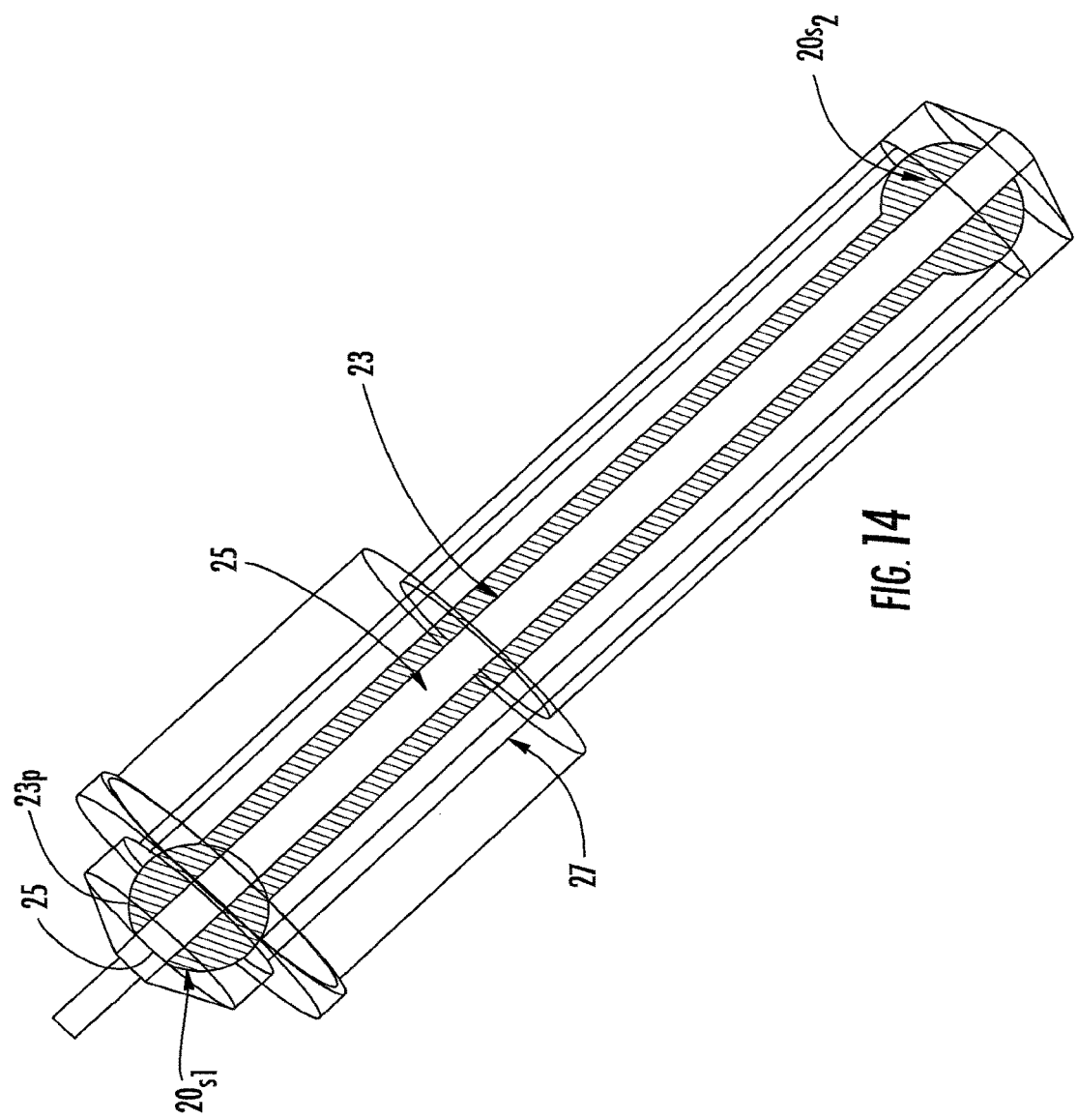

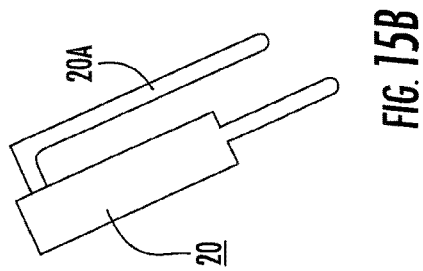
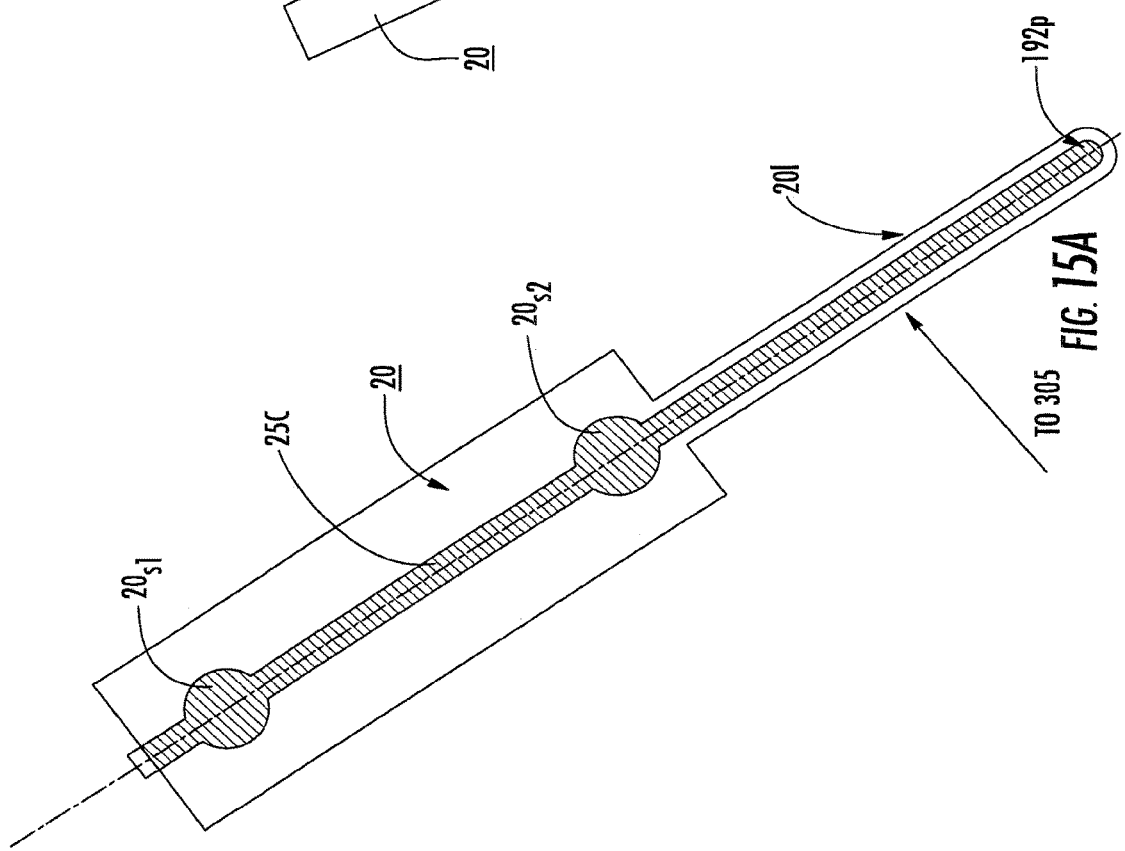

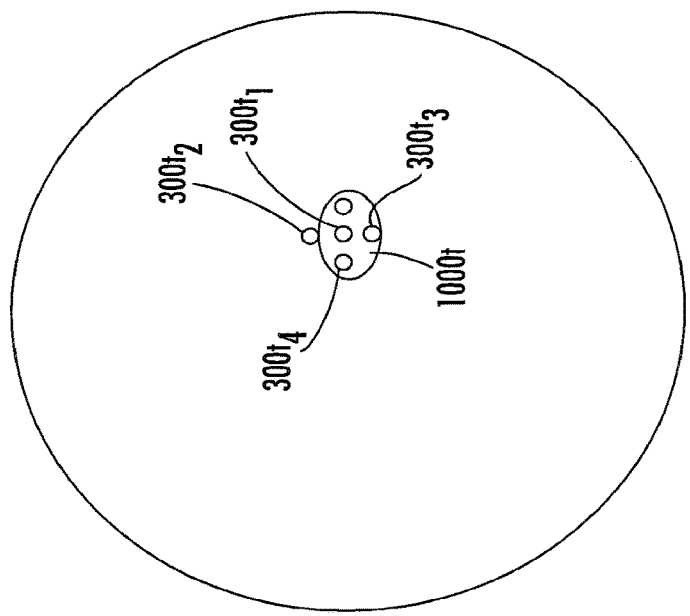
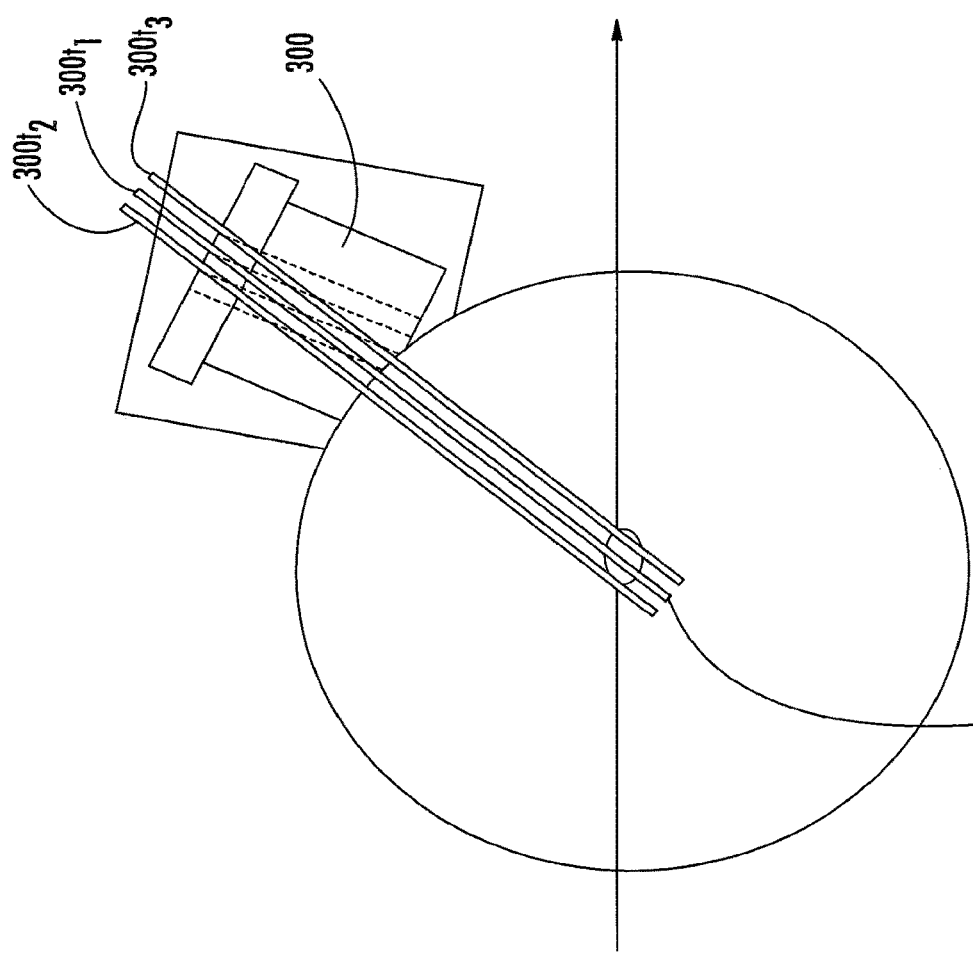
FIG. 16B
FIG. 16A

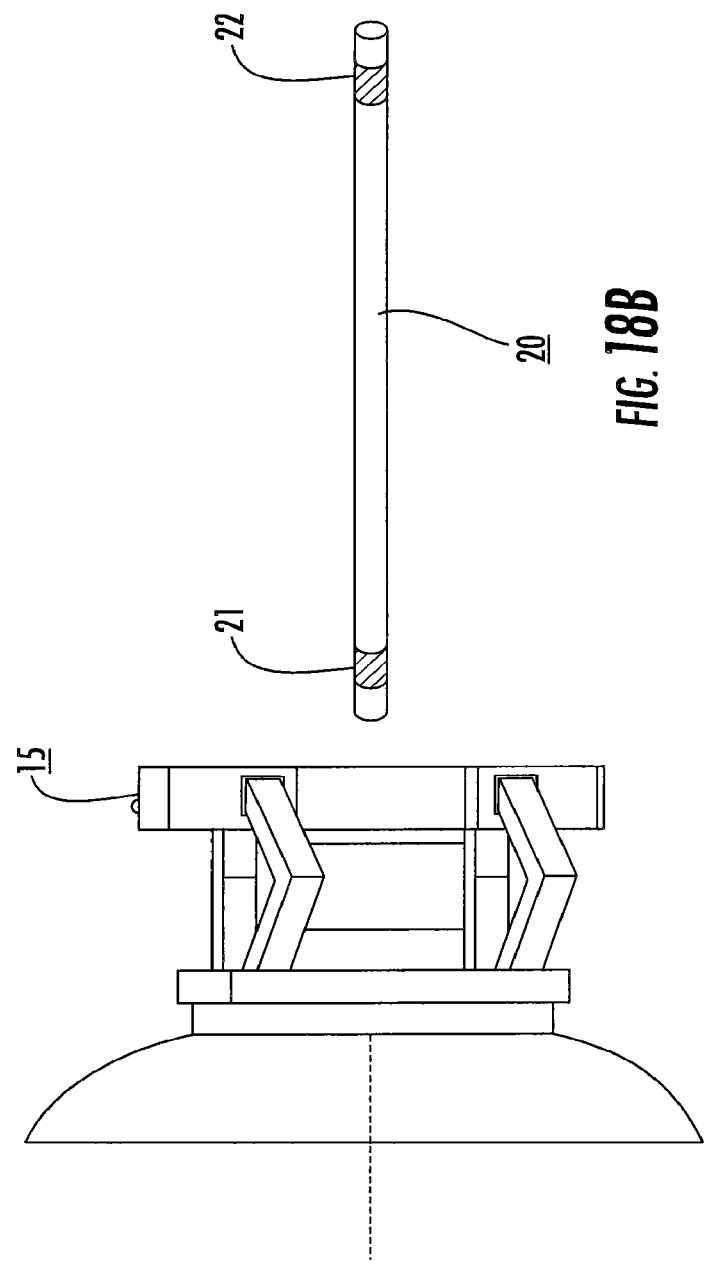

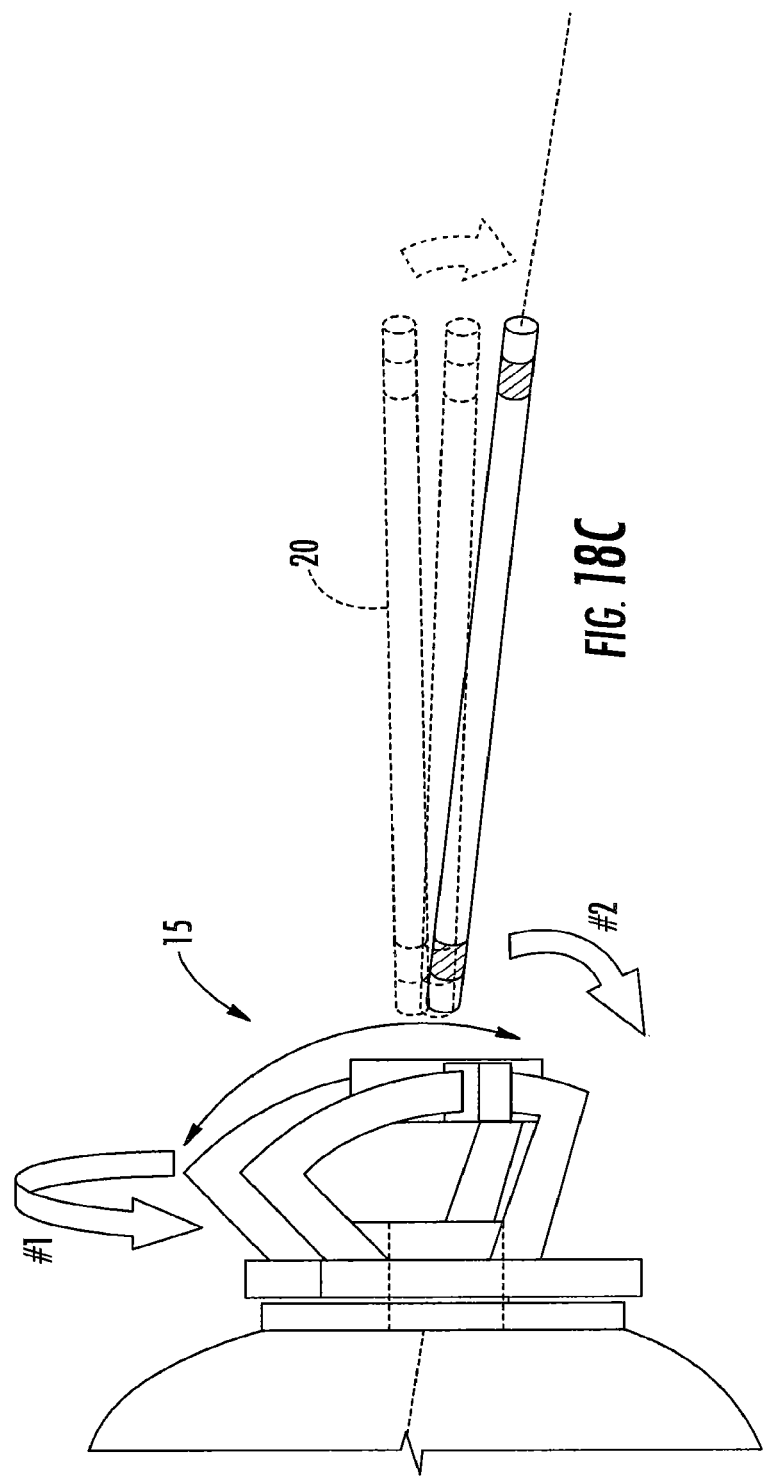

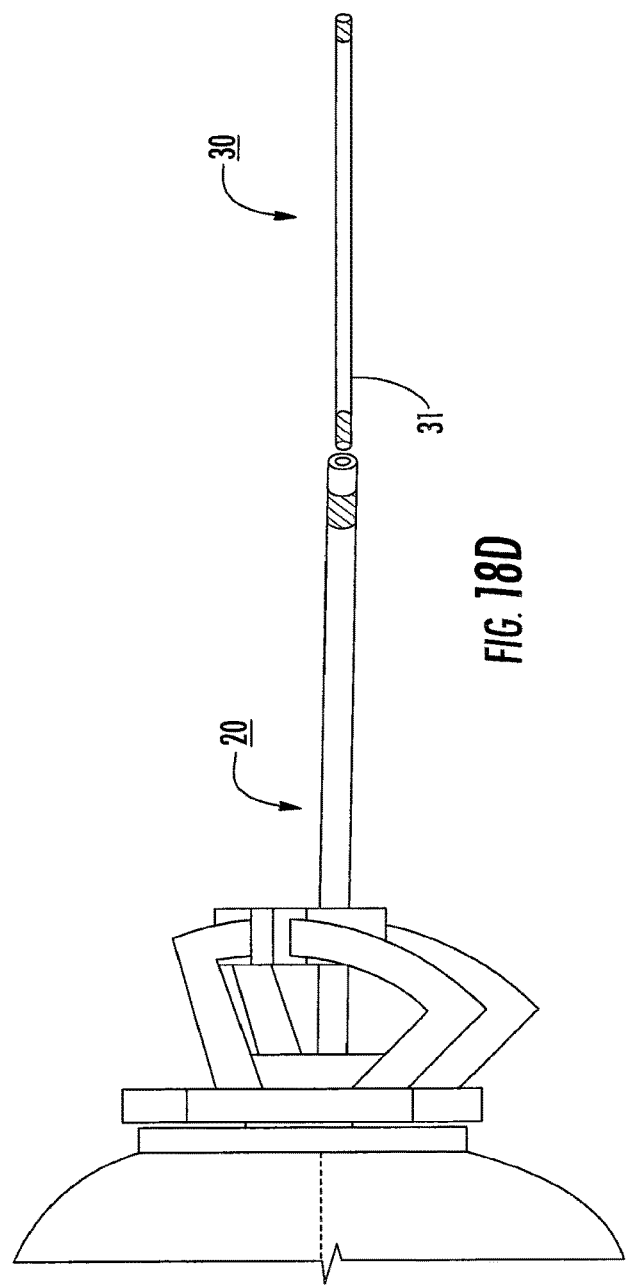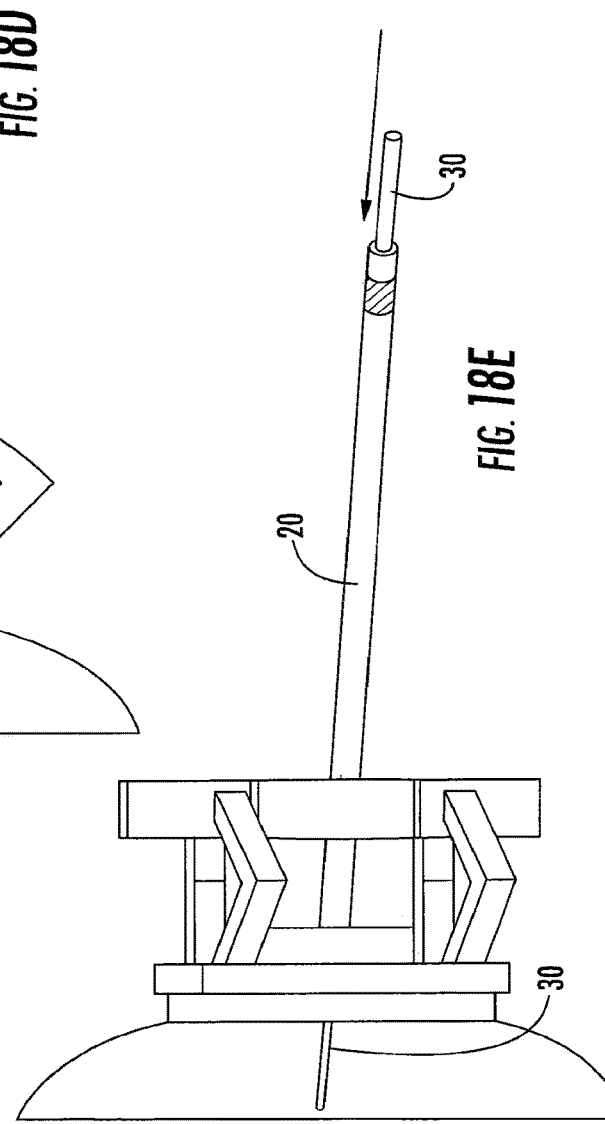

SURGICAL IMAGE-GUIDED NAVIGATION DEVICES AND RELATED SYSTEMS

RELATED APPLICATIONS

This application is a continuation of U.S. patent application Ser. No. 14/693,456, filed Apr. 22, 2015, which is a continuation of U.S. patent application Ser. No. 12/066,862, with an international filing date Nov. 29, 2006 (with a national phase filing date of Aug. 29, 2008), which is now U.S. Pat. No. 9,042,958, issued May 26, 2015, which is a 35 USC 371 national phase application of PCT/US2006/045752, filed Nov. 29, 2006, which claims the benefit of U.S. Provisional Patent Application Ser. No. 60/740,353, filed Nov. 29, 2005, the contents of which are hereby incorporated by reference as if recited in full herein.

FIELD OF THE INVENTION

The present invention relates to placement/localization of interventional medical devices and/or therapies in the body. Embodiments of the present invention may be particularly suitable for placing neuro-modulation leads, such as Deep Brain Stimulation ("DBS") leads, implantable parasympathetic or sympathetic nerve chain leads and/or CNS stimulation leads.

BACKGROUND OF THE INVENTION

Deep Brain Stimulation (DBS) is becoming an acceptable therapeutic modality in neurosurgical treatment of patients suffering from chronic pain, Parkinson's disease or seizure, and other medical conditions. Other electro-stimulation therapies have also been carried out or proposed using internal stimulation of the sympathetic nerve chain and/or spinal cord, etc.

One example of a prior art DBS system is the Activa® system from Medtronic, Inc. The Activa® system includes an implantable pulse generator stimulator that is positioned in the chest cavity of the patient and a lead with axially spaced apart electrodes that is implanted with the electrodes disposed in neural tissue. The lead is tunneled subsurface from the brain to the chest cavity connecting the electrodes with the pulse generator. These leads can have multiple exposed electrodes at the distal end that are connected to conductors which run along the length of the lead and connect to the pulse generator placed in the chest cavity.

MRI is an imaging modality that can be used to evaluate cardiac, neurological and/or other disorders. It may be desirable to use MRI for patients with implanted stimulation devices and leads. However, currently available lead systems may be unsuitable to use in a magnetic resonance imaging (MRI) environment. For example, the devices may not be MRI compatible, i.e., they may contain ferromagnetic materials, which may distort the MRI images. Also, currently available lead/probe/cable systems may be susceptible to unwanted induced RF and/or AC current and/or localized heating of the tissue. For example, the Medtronic Activa® device typically recommends that MRI imaging be carried out in a 1.5T magnet without using body coils, i.e., only using head coils for transmission of the RF excitation pulse(s). Also, the problem of unwanted RF deposition may increase as higher magnetic fields, such as 3T systems, become more common for MRI imaging (the RF pulses having shorter wavelengths).

It is believed that the clinical outcome of certain medical procedures, particularly those using DBS, may depend on the precise location of the electrodes that are in contact with the tissue of interest. For example, to treat Parkinson's tremor, presently the DBS probes are placed in neural tissue with the electrodes transmitting a signal to the thalamus region of the brain. DBS stimulation leads are conventionally implanted during a stereotactic surgery, based on pre-operative MRI and CT images. These procedures can be long in duration and may have reduced efficacy as it has been reported that, in about 30% of the patients implanted with these devices, the clinical efficacy of the device/procedure is less than optimum.

Notwithstanding the above, there remains a need for alternative interventional tools.

SUMMARY OF EMBODIMENTS OF THE INVENTION

Embodiments of the present invention are directed to medical tools, systems and methods useful for MRI-guided localization and/or placement of interventional therapies and/or devices.

Some embodiments of the present invention provide systems that utilize at least one MRI to visualize (and/or locate) a therapeutic region of interest (such as, for example, a target site inside the brain) and utilize at least one MRI to visualize (and/or locate) an interventional tool or tools that are used to deliver a therapy and/or to place a chronically (typically permanently) implantable device that will deliver a therapy.

Some embodiments include a targeting cannula with a lumen sized and configured to slidably receive an elongate probe. The elongate probe can include a recording electrode (e.g., transducer) and/or a stimulation electrode. Optionally, the targeting cannula and/or probe or components thereof may be MRI visible.

Some embodiments of the present invention can be used to place interventional lead systems in the body. The lead placement systems can be configured to both collect MRI and/or NMR data and sense local signals (e.g., EEG signals) and may also or alternatively be configured to stimulate local (e.g., neural) tissue. The lead placement system may be used to place implantable deep brain stimulation leads. The lead placement systems may also be configured to place implantable cardiac interventional leads or devices.

The lead placement system can include a probe and/or sheath that can be relatively long, having a length in the body of greater than 10 cm, or may have a lesser length, such as between about 3-6 cm. The probe and/or lead can hold one or a plurality of electrodes and/or at least one may be a recording electrode. The probe may hold a recording and a stimulating electrode. The probe and/or sheath can be MRI active (include MRI imaging coils and/or cooperate with other components to define an MRI antenna).

In some embodiments, the electrodes and stimulation control module can be configured to generate different stimulation field patterns having different size and shape stimulation volumes and different directional stimulation volumes and the patient data analysis module may be configured to automatically determine an optimal location of an electrode for DBS for a particular patient.

Still other embodiments are directed to systems for MRI guided placement of deep brain stimulation leads. The systems include a translatable targeting cannula, a frameless mount configured to hold the targeting cannula, and an MRI antenna with transducer configured to releasably engage the targeting cannula. The cannula may be configured to be inserted into a burr hole placed in a patient's skull and the stimulation probe and MRI antenna and stimulation probe may be configured for deep brain placement guided through the cannula.

Some embodiments are directed to MRI compatible localization and/or guidance systems for facilitating placement of an interventional device in vivo. The systems include: (a) a mount having a base with a patient access aperture adapted for fixation to a patient, wherein an upper portion of the mount is able to controllably translate with at least two degrees of freedom; (b) a targeting cannula having at least one axially extending lumen configured to attach to the mount; and (c) an elongate probe configured to snugly slidably advance and retract in one of the at least one axially extending lumen of the targeting cannula, the elongate probe comprising at least one of a recording electrode or a stimulation electrode. In operation, the mount can be adjusted to provide a desired internal access path trajectory to a target location.

Some embodiments are directed to MRI compatible localization and/or guidance systems for facilitating placement of an interventional device in vivo. The systems include: (a) a mount having a receiving port and a base with an access aperture adapted for fixation to a patient, the mount port configured to translate with at least two degrees of freedom; (b) a targeting cannula having at least one axially extending lumen configured to reside in the port; and (c) an elongate probe configured to define an MRI antenna configured to snugly slidably advance and retract in one of the at least one axially extending lumen of the targeting cannula. In operation, the targeting cannula can be positionally adjusted in the mount to provide a desired internal access path trajectory through the mount access aperture to a target location.

Some embodiments are directed to MRI interventional tools that include: (a) a cannula with a through lumen and at least one axially extending closed fluid filled lumen or channel; and (b) a first multipurpose probe configured to slidably extend through the lumen of the cannula.

Some embodiments are directed to MRI-compatible interventional tools that include: (a) a frameless mount; (b) a multi-lumen insert configured to mount to the frameless mount; and (c) an MRI visible targeting cannula with a closed perimeter configured to slidably reside in one lumen of the multilumen insert when the insert is mounted to the frameless mount.

Other embodiments are directed to MRI interventional or placement tools that include: (a) a mount having a patient access aperture configured to mount to a patient; (b) an elongate delivery sheath extendable from through the access aperture of the mount to a target access location in the patient; and (c) a fluid filled tube configured to slidably advance with and retract from the sheath.

Still other embodiments are directed to MRI guided localization systems. The systems include: (a) a base with an in vivo access aperture configured to mount to a patient; (b) a translatable mount member attached to the base, the translatable member configured to translate about a pivot point extending proximate the base access aperture, the translatable member having a receiving port configured to receive at least one of a targeting cannula or a multi-lumen insert; (c) a plurality of sensors in communication with at least one of the base and translatable member whereby the sensors define positional data of the mount member; (d) a drive system in communication with the translatable mount member; and (e) a control circuit in communication with the drive system configured to direct the translatable member to translate to define a desired trajectory orientation.

Some embodiments are directed to automated trajectory adjustment systems. The systems include: (a) a mount member with a base having an access aperture therethrough configured to reside against a mounting surface of a patient; (b) an MRI visible elongate member configured to mount to the mount member; (c) at least one position sensor in communication with the mount member; (d) a drive system in communication with the mount member; and (e) a control circuit in communication with the drive system configured to identify adjustments to alter the position of the mount member to obtain a desired trajectory of an access path through the access aperture into the patient.

Other embodiments are directed to systems for MRI guided localization of therapies/tools. The systems include: (a) an MRI visible elongate member; and (b) a localization system in communication with a MRI scanner configured to programmatically determine a scan plane location of the elongate member having a first trajectory in 3D MRI space whereby the elongate member acts as an MRI detectable marker.

Still other embodiments are directed to methods for automatically defining a scan plane associated with an elongate MRI visible marker. The methods include programmatically determining a scan plane location of an MRI visible elongate member held in a mount affixed to a patient and residing in 3D MRI space with an associated first trajectory.

Some embodiments are directed to frameless head mounts for MRI interventional procedures. The mounts include: (a) a base having a patient access aperture configured to affix to a burr hole in a skull of a patient; (b) a rotatable platform attached to the base; and (c) a pair of spaced apart upwardly extending arms holding a receiving port, the receiving port being able to translate in response to translation of the arms.

The frameless mount may optionally also include respective non-ferromagnetic flexible drive cables attached to the rotation and pitch adjustment members to allow a user to adjust an access path trajectory while the user resides proximate but outside an end of a bore of a magnet associated with an MRI scanner without moving the patient. The mount may also optionally include an automated trajectory adjustment circuit in communication with the adjustment members whereby the receiving port is automatically moved to a desired position based on MRI data.

Another aspect of the invention relates to methods of adjusting a trajectory of a head mount defining an internal access path trajectory during an MRI-guided interventional procedure. The method includes: (a) affixing a head mount with a holding member having adjustable pitch and rotation to a head of a patient; and (b) adjusting at least one of pitch or rotation of the holding member to define a desired access path trajectory into the patient while the patient remains in position in a bore of a magnet.

Although described above with respect to method aspects of the present invention, it will be understood that the present invention may also be embodied as systems and computer program products.

Other systems, methods, and/or computer program products according to embodiments of the invention will be or become apparent to one with skill in the art upon review of the following drawings and detailed description. It is intended that all such additional systems, methods, and/or computer program products be included within this description, be within the scope of the present invention, and be protected by the accompanying claims.

These and other embodiments will be described further below.

BRIEF DESCRIPTION OF THE DRAWINGS

FIG. 10C is a greatly enlarged front perspective view of the device shown in FIG. 10B.

FIG. 10D is a greatly enlarged side perspective view of the device shown in FIG. 10B.

FIGS. 11A-11F illustrate different configurations of the frameless mount shown in FIG. 10A.

FIG. 14 is a partially transparent side view of a targeting cannula with a through lumen and a fluid filled axially extending segment according to embodiments of the invention.

FIG. 15A is a schematic side view of a targeting cannula with a fluid filled chamber that can reside in a lumen of a multi-lumen insert such as that shown in FIG. 12A.

FIG. 15B is a side schematic view of the targeting cannula shown in FIG. 15A alternately configured with an axially extending side arm according to some embodiments of the invention.

FIG. 16A is a schematic illustration of a visualization of trajectory lines in an oblique coronal/sagittal image extending from different lumens to a target site according to some embodiments of the invention.

FIG. 16B is a schematic illustration of the trajectory lines as they intersect the target site in an axial/oblique scan according to embodiments of the invention.

FIGS. 18A-18E are schematic illustration of additional steps that can be taken to define a trajectory and/or place an interventional device according to embodiments of the invention.

DETAILED DESCRIPTION OF EMBODIMENTS OF THE INVENTION

Figure 1A:
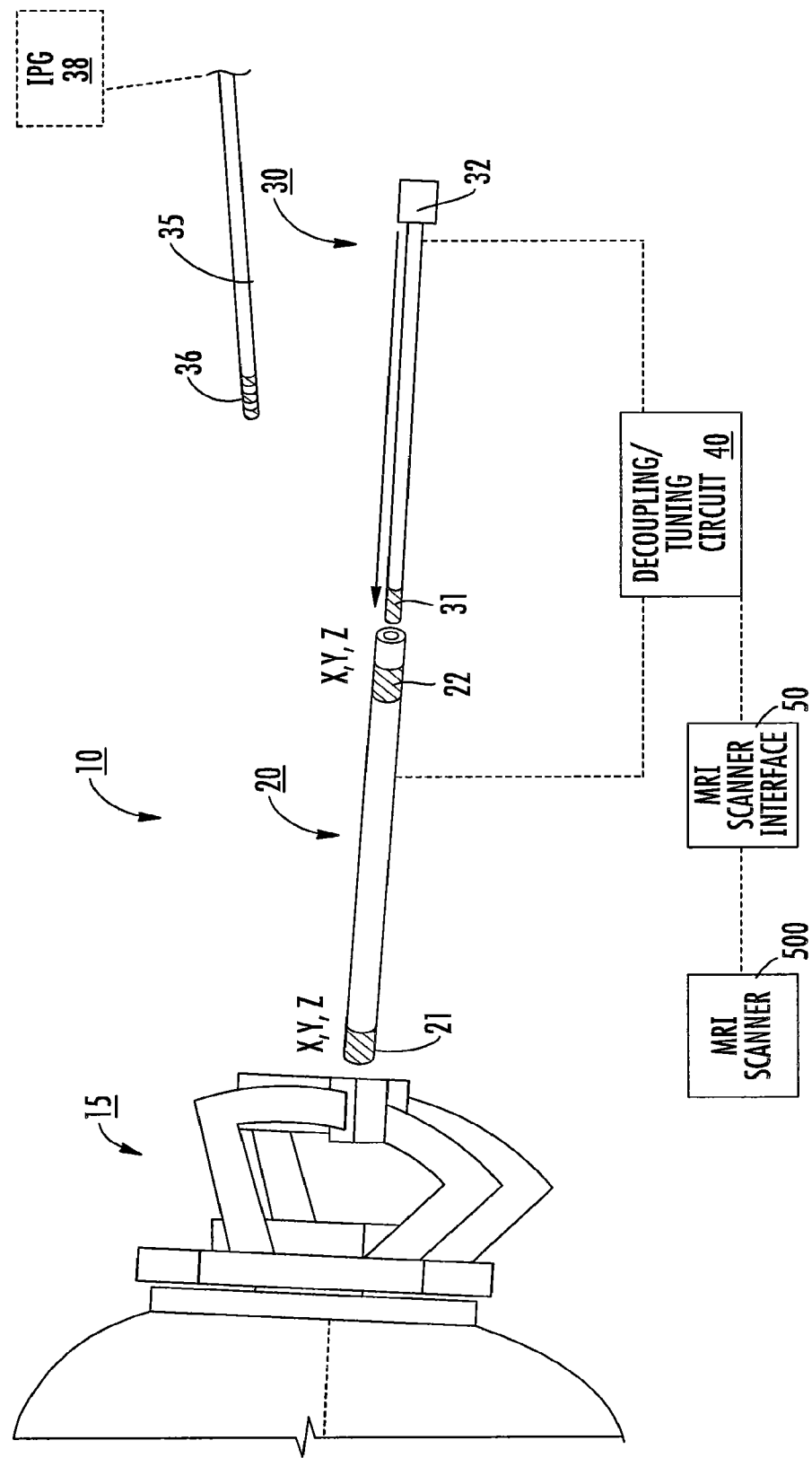
FIG. 1A is a schematic illustration of a MRI guided localization system according to embodiments of the present invention.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain antenna embodiment, features or operation of one lead system embodiment can apply to others.

In the drawings, the thickness of lines, layers, features, components and/or regions may be exaggerated for clarity and broken lines illustrate optional features or operations, unless specified otherwise. In addition, the sequence of operations (or steps) is not limited to the order presented in the claims unless specifically indicated otherwise. It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. Although described or shown with respect to one embodiment, the features so described or shown can apply to other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

The term "RF safe" means that the device, lead or probe is configured to operate safely when exposed to normal RF signals associated with conventional MRI systems. The device can be configured with RF chokes, RF traps, high impedance segments and/or other electrical circuits that allow for the RF safe operation in MRI environments. The device may be active or decoupled during RF transmit in an MRI procedure.

The term "MRI visible" means that the device is visible, directly or indirectly, in an MRI image. The visibility may be indicated by the increased SNR of the MRI signal proximate to the device (the device can act as an MRI receive antenna to collect signal from local tissue) and/or that the device actually generates MRI signal itself, such as via suitable hydro-based coatings and/or fluid (typically aqueous solutions) filled channels or lumens. The term "MRI compatible" means that the so-called system and/or component(s) is safe for use in an MRI environment and/or can operate as intended in an MRI environment, and, as such, if residing within the high-field strength region of the magnetic field, is typically made of a non-ferromagnetic MRI compatible material(s) suitable to reside and/or operate in a high magnetic field environment. The term high-magnetic field refers to field strengths above about 0.5 T, typically above 1.0T, and more typically between about 1.5T and 10T.

The term "targeting cannula" refers to an elongate device, typically having a substantially tubular body that can be oriented to provide positional data relevant to a target treatment site and/or define a desired access path orientation or trajectory. At least portions of the targeting cannulae contemplated by embodiments of the invention can be configured to be visible in an MRI image, thereby allowing a clinician to visualize the location and orientation of the targeting cannula in vivo relative to fiducial and/or internal tissue landscape features. Thus, the term "cannula" refers to an elongate device that can be inserted into a mount that attaches to a patient, but does not necessarily enter the body of a patient.

The term "imaging coils" refers to a device that is configured to operate as an MRI receive antenna. The term "coil" with respect to imaging coils is not limited to a coil shape but is used generically to refer to MR' antenna configurations, loopless, looped, etc., as are known to those of skill in the art. The term "fluid-filled" means that the component includes an amount of the fluid but does not require that the fluid totally, or even substantially, fill the component or a space associated with the component. The fluid may be an aqueous solution, MR contrast agent, or any material that generates MRI signal.

The term "two degrees of freedom" means that the mount allows for at least translational (swivel or tilt) and rotational movement over a fixed site, which may be referred to as a Remote Center of Motion (RCM).

The term "interactive" refers to a device and/or algorithm that can respond to user input to provide an output, typically using a Graphic User Interface (GUI). The GUI may operate with known GUI drawing tools, such as spline inputs to define a target treatment site and/or trajectory to the site in an image of an MRI visualization of the patient on a clinician workstation display. The term "spline" refers to free-form curves defined with a set of control points. Drawing of a spline curve is by placement of these points. An open or closed spline can be selected using a spline dialog. An object or point can be moved by holding down an input key, such as <Shift>. The control points can be edited using a point editing mode where a handle to move the control point. For example, holding down <Control> and dragging on a handle to alter the shape factor of that control point.

The term "programmatically" refers to operations directed and/or primarily carried out electronically by computer program modules, code and instructions.

The term "high radiofrequency" or "high RF" refers to RF frequencies that are at or above about 1 MHz, and includes radiofrequencies in the range of about 1 MHz to about 256 MHz. Some embodiments of the present invention configure devices so as to have high impedance circuit segments or a high impedance circuit at high RF and low impedance circuit segments or circuit at DC or low frequency (at a kHz or less frequency or frequency range), i.e., at frequencies used for treatment such as stimulation or ablation. For example, for 1.5T, 3.0T and 6.0T systems, the respective frequencies are 64 MHz, 128 MHz and 256 MHz. The frequencies of the different MRI systems are well known to those of skill in the art. The devices can be configured to have high impedance at several of the radiofrequencies associated with high-field magnet MRI systems, such as systems with magnets above about 1.0T, such as about 1.0T, 1.5T, 2.0T, 3.0T, 4.0T, 5.0T, 6.0T and 9.0T, typically between about 1T to 15T.

The term "high impedance" means an impedance sufficiently high to inhibit, block or eliminate flow of RF-induced current at a target frequency range(s). The impedance has an associated resistance and reactance as is well known to those of skill in the art. Some embodiments provide an impedance of at least about 300 Ohms, typically between about 400 Ohms to about 600 Ohms, such as between about 450 Ohms to about 500 Ohms, while other embodiments provide an impedance of between about 500 Ohms to about 1000 Ohms. Embodiments of the invention configure lead systems that provide sufficiently high-impedance at frequencies associated with a plurality of different conventional and future magnetic field strengths of MRI systems, such as at least two of 1.5T, 2.0T, 2.5T, 3.0T, 9.0T, and the like, allow for safe use in those environments (future and reverse standard MRI system compatibility).

The term "tuned" means that a parallel resonant circuit with inductive and capacitive characteristics defined by certain components and configurations has high impedance at one or more target frequencies, typically including one or more MRI operating frequencies.

The term "coiled segment" refers to a conductive lead (trace, wire or filar) that has a coiled configuration. The term "co-wound segments" means that the affected leads, conductors, wires and/or filars can be substantially concentrically coiled at different radii, one above the other, or concentrically coiled closely spaced at substantially the same diameter. The term "co-wound" is used to describe structure and is not limiting to how the structure is formed (i.e., the coiled segments are not required to be wound concurrently or together, but may be so formed). The terms "conductive element", "conductive lead" and "conductors" are used interchangeably and refer to a conductive path that connects target components (such as, for example, a stimulation source and an electrode) and can include one or combinations of a metallic trace, a wire, a flex circuit, a filar(s), or other conductive configuration. As such, the conductors or conductive elements include long linear and/or non-linear conductors that can be formed with one or more of discrete wires, flex circuits, filars (bi, quadra or other winding), or by plating, etching, deposition, or other fabrication methods for forming conductive electrical paths.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this application and should not be interpreted in an idealized or overly formal sense unless expressly so defined herein.

Embodiments of the present invention can be configured to guide and/or place interventional devices and/or therapies to any desired internal region of the body or object. The object can be any object, and may be particularly suitable for animal and/or human subjects. Some probe embodiments can be sized and configured to place implantable DBS leads for brain stimulation, typically deep brain stimulation. Some embodiments can be configured to deliver tools or therapies that stimulate a desired region of the sympathetic nerve chain. Other uses inside or outside the brain include stem cell placement, gene therapy or drug delivery for treating physiological conditions. Some embodiments can be used to treat tumors.

In some embodiments the interventional tools can be configured to facilitate high resolution imaging via integral imaging coils (receive antennas), and/or the interventional tools can be configured to stimulate local tissue, which can facilitate confirmation of proper location by generating a physiologic feedback (observed physical reaction or via fMRI).

Some embodiments can be used to deliver bions, stem cells or other target cells to site-specific regions in the body, such as neurological target and the like. In some embodiments, the systems deliver stem cells and/or other cardio-rebuilding cells or products into cardiac tissue, such as a heart wall via a minimally-invasive MRI guided procedure, while the heart is beating (i.e., not requiring a non-beating heart with the patient on a heart-lung machine). Examples of known stimulation treatments and/or target body regions are described in U.S. Pat. Nos. 6,708,064; 6,438,423; 6,356,786; 6,526,318; 6,405,079; 6,167,311; 6,539,263; 6,609,030 and 6,050,992, the contents of which are hereby incorporated by reference as if recited in full herein.

Generally stated, some embodiments of the invention are directed to MRI interventional procedures and provide interventional tools and/or therapies that may be used to locally place interventional tools or therapies in vivo to site specific regions using an MRI system. The interventional tools can be used to define an MRI-guided trajectory or access path to an in vivo treatment site. Some embodiments of the invention provide interventional tools that can provide positional data regarding location and orientation of a tool in 3-D space with a visual confirmation on an MRI. Embodiments of the invention may provide an integrated system that may allow physicians to place interventional devices/leads and/or therapies accurately and in shorter duration procedures over conventional systems (typically under six hours for DBS implantation procedures, such as between about 1-5 hours).

In some embodiments, an MRI can be used to visualize (and/or locate) a therapeutic region of interest inside the brain and utilize an MRI to visualize (and/or locate) an interventional tool or tools that will be used to deliver therapy and/or to place a permanently implanted device that will deliver therapy. Then, using the three-dimensional data produced by the MRI system regarding the location of the therapeutic region of interest and the location of the interventional tool, the system and/or physician can make positional adjustments to the interventional tool so as to align the trajectory of the interventional tool, so that when inserted into the body, the interventional tool will intersect with the therapeutic region of interest. With the interventional tool now aligned with the therapeutic region of interest, an interventional probe can be advanced, such as through an open lumen inside of the interventional tool, so that the interventional probe follows the trajectory of the interventional tool and proceeds to the therapeutic region of interest. It should be noted that the interventional tool and the interventional probe may be part of the same component or structure. A sheath may optionally form the interventional tool or be used with an interventional probe or tool.

In particular embodiments, using the MRI in combination with imaging coils and/or MRI contrast material that may be contained at least partially in and/or on the interventional probe or sheath, the location of the interventional probe within the therapeutic region of interest can be visualized on a display or image and allow the physician to either confirm that the probe is properly placed for delivery of the therapy (and/or placement of the implantable device that will deliver the therapy) or determine that the probe is in the incorrect or a non-optimal location. Assuming that the interventional probe is in the proper desired location, the therapy can be delivered and/or the interventional probe can be removed and replaced with a permanently implanted therapeutic device at the same location.

In some embodiments, in the event that the physician determines from the MRI image produced by the MRI and the imaging coils, which may optionally be contained in or on the interventional probe, that the interventional probe is not in the proper location, a new therapeutic target region can be determined from the MRI images, and the system can be updated to note the coordinates of the new target region. The interventional probe is typically removed (e.g., from the brain) and the interventional tool can be repositioned so that it is aligned with the new target area. The interventional probe can be reinserted on a trajectory to intersect with the new target region.

Embodiments of the present invention will now be described in detail below with reference to the figures. FIG.

1A illustrates a MRI guided interventional placement system 10 that includes a mount 15, a targeting cannula 20, and an elongate probe 30. Although shown as a frameless mount 15, frame-based or other suitable mounting systems may also be used that allow for the adjustability (typically at least two degrees of freedom, including rotational and translational) and calibration/fixation of the trajectory of the targeting cannula 20 and/or probe or tool 30. The mount 15 or components thereof (and/or the patient) may include fiducial markers that can be detected in an MRI to facilitate registration of position in an image.

The system 10 may also include a decoupling/tuning circuit 40 that allows the system to cooperate with an MRI scanner 60. An intermediate MRI scanner interface 50 may be used to allow communication with the scanner 60. The interface 50 may be hardware, software or a combination of same.

The elongate probe 30 can include at least one electrode 31 on a distal tip portion thereof. The electrode 31 can be a recording and/or stimulating electrode. The electrode 31 can be configured to deliver test voltages for physiologic confirmation of location/efficacy that can be done by fMRI or by feedback from a non-anesthetized patient. Thus, a patient can be stimulated with the interventional probe 30 (the stimulation may be via a transducer on a distal tip portion of the probe), to help confirm that the interventional probe is in the correct location (i.e., confirm proper location via anatomical as well as provide physiologic information and feedback). During (and typically substantially immediately after) stimulation from the interventional probe, the physician can monitor for a physiologic response from the patient that can be observed either directly from the patient as a physical response or via an fMRI-visible response.

The elongate probe 30 can be MRI-visible and may optionally be configured to define an MRI antenna. The system 10 can be configured to allow for real-time tracking under MRI, with an SNR imaging improvement in a diameter of at least 5-10 mm proximate the probe 30 or cannula 20.

The targeting cannula 20 can also or alternately be MRI-visible. The cannula 20 can include an axially extending open lumen 25 that slidably receives the probe 30. In some particular embodiments, the cannula 20 may optionally comprise a plurality of spaced apart microcoils 21, 22 configured to provide data used to provide 3-D dimensional data in MRI 3-D space, such as a trajectory, or 3-D spatial coordinates of position of the cannula 20. As shown, the microcoils 21, 22 can each provide data that can be correlated to a three-dimensional (X,Y,Z) position in 3-D space in the body. The mircocoils 21, 22 can be in communication with the MRI scanner, and tracking sequences can be generated and data from one or more of the MRI scanner channels can be used to define positional 3-D positional data and a trajectory thereof.

In some particular embodiments, the progress of the cannula 20 and/or interventional probe 30 may optionally be tracked in substantially real-time as it advances to the target via the coils 21, 22 (similar ones of which may also or alternatively be on or in probe 30) and/or antenna 30a. However, real-time tracking may not be desired in some embodiments.

Figure 1B:
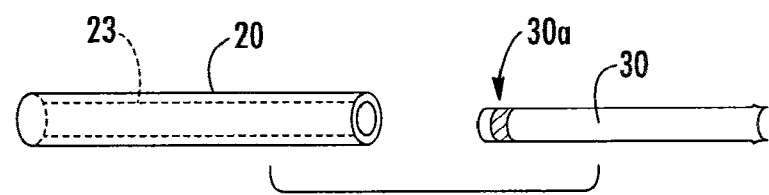
FIG. 1B is a schematic partial side view illustration of a targeting cannula and probe according to some embodiments of the invention.

As shown in FIG. 1B, the cannula 20 can include at least one axially extending fluid-filled hollow lumen or closed channel 23 with fluid that can generate MRI signal that can be detected by the MRI scanner and/or by an internal MRI antenna incorporated on and/or into the cannula 20 that can increase the SNR of the fluid to increase its visibility in an MRI. The fluid may be an aqueous solution (able to resonate at the proton frequency). The cannula 20 can include an axially extending, relatively thin segment, which creates a high contrast MRI image (a segment filled with water or other suitable contrast solution filled section/lumen). The thickness of the segment may be between about 0.25-4 mm (and the segment can have a tubular shape with a diameter or may define another cross-sectional shape such as a square section). The cannula 20 may include MRI imaging coils (MR antenna 30a) to increase the signal from the high contrast fluid. The targeting cannula 20 may fit in the mount directly or in a multilumen insert (as will be discussed further below).

Figure 1C:
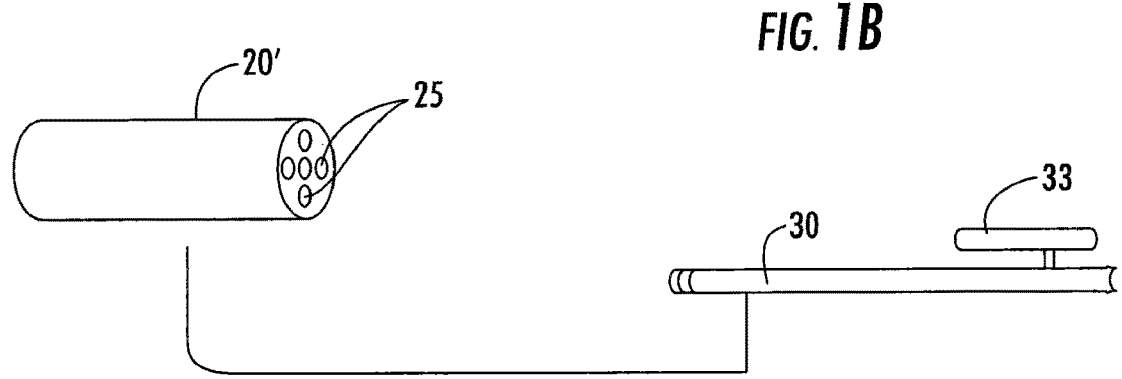
FIG. 1C is a partial side view illustration of a different targeting cannula configuration and a different probe configuration according to embodiments of the invention.
Figure 12D:
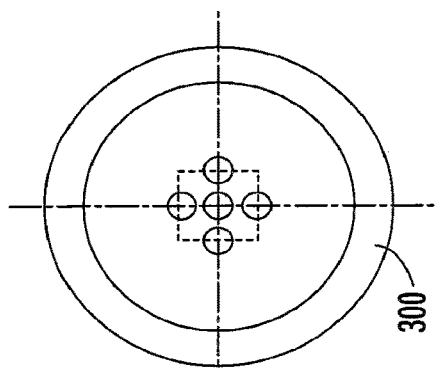
FIGS. 12C and 12D are end views and FIG. 12E is a side view (with the top facing down) of the device shown in FIG. 12A.
Figure 12B:
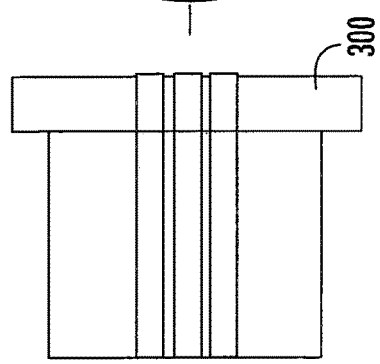
FIG. 12B is a side view.
Figure 12C:
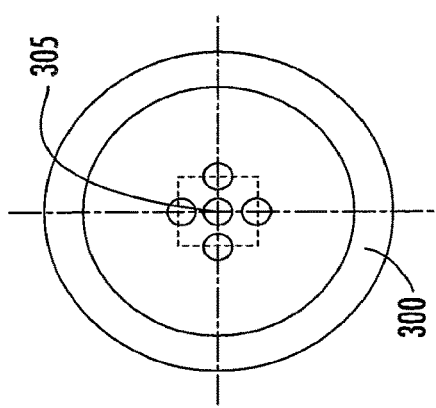
Figure 12E:
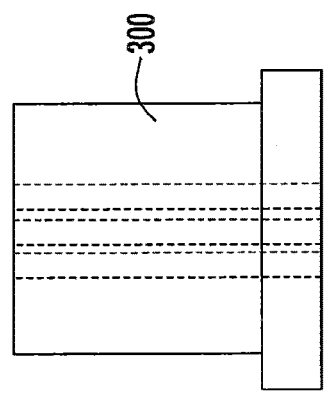
Figure 12A:
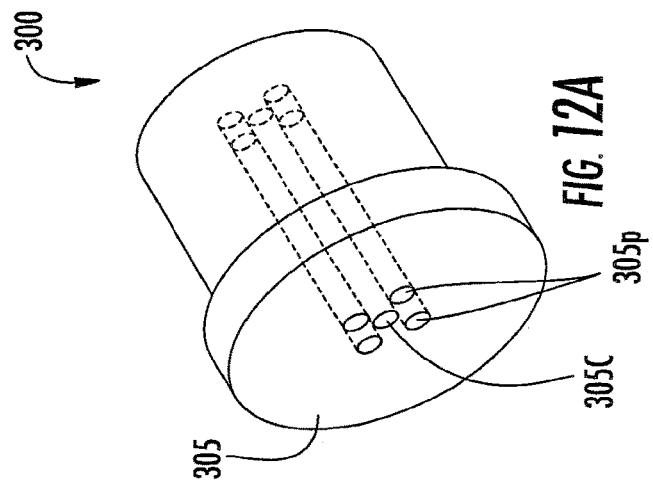
FIG. 12A is a perspective side view of a multi-lumen insert that can be held by a mount according to embodiments of the invention.
Figure 13C:
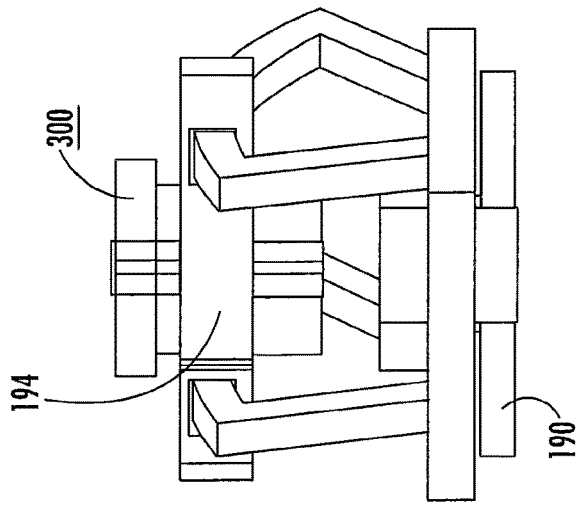
FIGS. 13B and 13C are side and front views thereof.
Figure 13B:
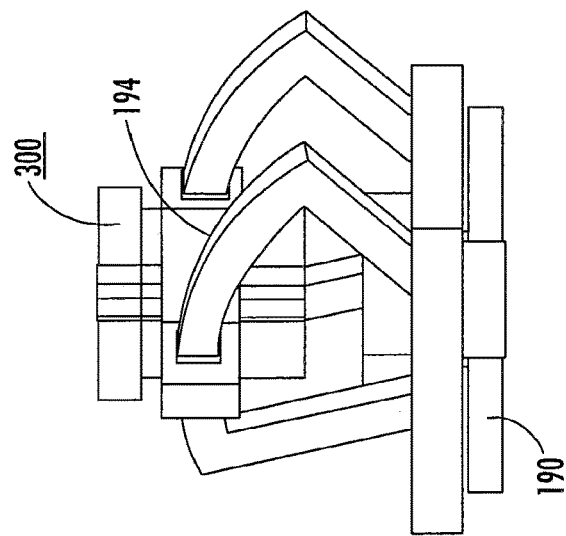
Figure 13A:
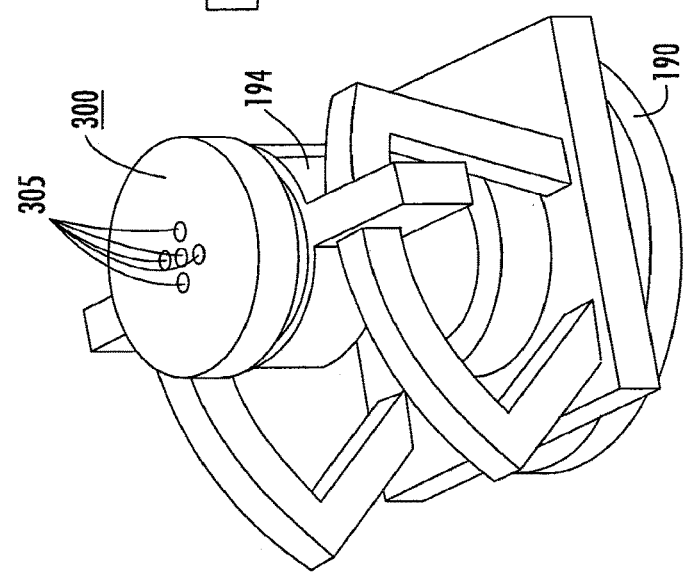
FIG. 13A is a side perspective view of the mount shown in FIG. 12A with the multi-lumen insert shown in FIG. 12A according to some embodiments of the invention.

FIG. 1C illustrates that the targeting cannula 20 can include a plurality of lumens 25. At least some of the lumens 25 can be parallel with others and extend axially along and through the cannula 20. These lumens 25 can define parallel tracts to a target in vivo site that can be selectively used to advance an interventional or localization probe, such as probe 30. The probe 30 can be configured to be selectively input into one lumen 25, typically over a distance that is proximate a pivot point or zone over a burr hole or other patient access entry location, or serially input into some or all of the lumens 25, thereby providing a corresponding change of trajectory of the access path to the target site. Some of the lumens 25 may be MRI-active such as being fluid filled or configured to slidably and releasably receive a fluid filled tube. Some of the lumens 25 may not extend the entire length of the cannula 20. FIG. 1C also illustrates that the probe 30 can include one or more axially extending side arms 33 that can be sized and configured to reside, at least partially, in a respective lumen 25 to provide MRI signal and appear in an MRI image. The fluid filled lumens 25 can define trajectories in MRI 3D space that extend into the body. The cannula 20 (and/or multi-lumen insert 300, FIG. 12A) can include fiducial orientation markers that indicate which side lumen is associated with which trajectory in an image. The fiducial marker can be defined by shapes, sizes or MRI visible signature shapes or features.

Figure 2E:
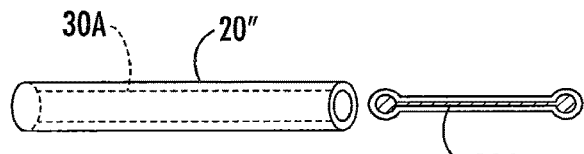
FIG. 2E is a side view of the sheath acting as a targeting cannula in combination with a fluid filled or MRI visible tube according to some embodiments of the invention.
Figure 2D:
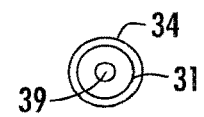
FIG. 2D is a sectional view of the probe and sheath shown in FIG. 2C according to embodiments of the present invention.
Figure 2A:
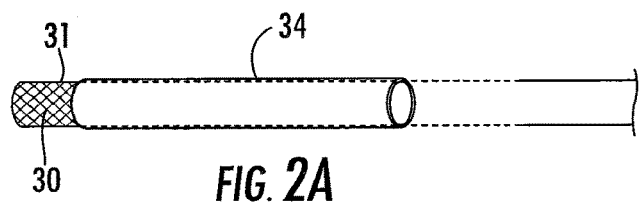
FIG. 2A is a partial side view illustration of a device with a retractable sheath according to embodiments of the invention.
Figure 2B:
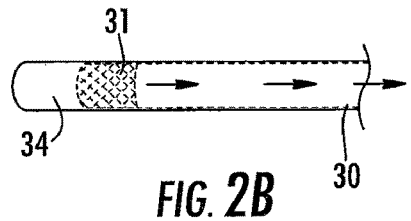
FIG. 2B a partial side view illustration of the device shown in FIG. 2A illustrating the sheath remaining in position as the probe is retracted according to embodiments of the invention.
Figure 2C:
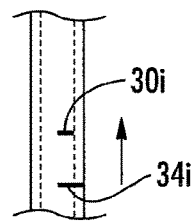
FIG. 2C is a schematic partial top view of a probe and sheath shown in FIG. 2A illustrating visual indicia of movement according to embodiments of the present invention.

FIGS. 2A-2D illustrate that, in some embodiments, the probe 30 can include an external sheath or sleeve 34 that can be configured to snugly reside about the probe 30 but remain in the body as the probe is slidably removed. The sheath 34 can include a lubricious coating or material or be otherwise configured with a suitable reduced coefficient of friction to allow a snug but slidable fit between the components 30, 34. The sheath or sleeve 34 can be a relatively thin biocompatible elastomeric tubular body with sufficient structural rigidity to maintain the defined delivery path to the local tissue after removal of the probe 30. That is, when the probe 30 is removed, the sheath 34 does not collapse on itself and does not move from the position as another lead is directed down the sheath to the defined therapeutic location. The sheath 34 can be slidably advanced over the electrode 31 before the probe 30 is retracted and removed from at least a distal end portion of the sheath 34 and from the targeting cannula 20. As shown in FIG. 2C, the sheath 34 and/or probe 30 can include externally visible indicia 34i, 30i, of axial extension that can be visually aligned so that a clinician can readily identify the correct movement extension for the sheath to be extended to be substantially precisely placed at the desired location identified by the electrode 31. The sheath 34 may also optionally include a collar or other member that can inhibit over-extension and/or bias the sheath to translate to the desired extension length (not shown). The sheath 34 typically extends up above and out of the frameless mount 15 to allow a clinician ease of access to retrieve (pull) the sheath 34 after the therapy and/or lead placement is complete.

In some embodiments, as shown in FIG. 2E, the delivery sheath 34 described above as enclosing and housing the multipurpose probe 30 may also be used first as a targeting cannula 20". In this embodiment, the delivery sheath 34 can be MRI-active and include on-board MRI coils or an MRI antenna 30a that is built-in and during the targeting/alignment steps, a contrast filled tube 134 can be advanced in the delivery sheath 34 (before the multi-purpose probe 30). Once the localization and/or alignment steps are completed, the fluid filled tube can be replaced by the multipurpose probe 30 and the active delivery sheath 34 and the multipurpose probe 30 can be advanced in the tissue. The fluid filled tube 134 may be deflated before removal to facilitate easy of removal.

As also shown in FIG. 1A, the system 10 may optionally be used with and/or also include at least one deep brain stimulation lead 35 with at least one electrode 36, typically a plurality of electrodes as shown. The lead 35 can be delivered via the cannula 20 after the trajectory and location target are defined using the probe 30 and cannula 20. The electrodes 31 and 36 are shown in FIG. 1A as generally cylindrical, but other configurations of electrodes may be used. The terms "lead" and "probe" can be used interchangeably to indicate a body used to support an interventional component such as, for example, the respective electrodes 31, 36. Other numbers of electrodes as well as other electrode configurations can be used. For example, the electrodes may be translatable with respect to the probe body or may be statically configured thereon. It is contemplated that the electrodes can be sized and configured to "fit" the desired internal target, which may be a relatively small region, such as less than about 1-3 mm. Typically, as shown in FIG. 1A, the electrodes can be held on a distal portion of the probe body. A connector 32 on the proximal end portion of the probe body 30 can be configured to reside outside of the body during lead placement. The proximal portion of the probe body can be configured to releasably connect with a circuit 40 and/or an MRI scanner interface 50 via connector 32.

As shown by the broken line, the system 10 may optionally also include at least one implantable pulse generator 38 that can connect to the implantable lead 35. The IPG 38 and lead 35 can also comprise MRI compatible materials and/or components. The frameless mount 15, the targeting cannula 20, and the probe 30 may be provided as single-use disposable sterilized components in a medical kit or may be re-sterilized by a clinic between uses.

The probe 30 is typically an elongate flexible probe comprising an outer layer of elastomeric material, such as a polymer, that extends across the outer surface of the probe body while leaving the electrode(s) 31 configured to contact the tissue in position in the body. The probe 30 includes at least one conductor lead that electrically connects the electrode 31 to a remote input or output source, such as the MRI scanner interface 50. The lead(s) can comprise any suitable material, and may, in some embodiments, comprise a shape memory alloy such as Nitinol.

The targeting cannula 20 can be an MRI-compatible, generally rigid cannula and/or a cannula 20 with increased rigidity relative to the probe 30, and can be configured to slidably receive at least the distal and intermediate portions of the probe body 30 to guide the distal end portion of the probe 30 into the intrabody target position. The cannula 20 can be configured according to a desired body entry location; e.g., for oral entry, the cannula 20 can be formed into a bite block, nasal cavity or ear plug member, and for non-neural uses, such as placement in the spinal column, no cannula may be required.

In some embodiments, the targeting cannula 20 and the interventional probe 30 can be configured as a unitary tool. In some embodiments, it is also possible that the targeting cannula 20 and the frameless mount 15 (with or without the probe 30) can be a unitary tool such that the components are affixed together.

As for other components noted above, in some embodiments, the implantable pulse generator 38 as well as the implantable lead 35 may also comprise MRI compatible materials to allow placement of the subject using the targeting cannula 20.

In some embodiments, as shown for example in FIG. 1B, the probe 30 comprises an MRI antenna 30a that is configured to pick-up MRI signals in local tissue during an MRI procedure. The MRI antenna 30a can be configured to reside on the distal portion of the probe 30. The MRI antenna 30a may also optionally be defined by the head mount 15, the targeting cannula 20 and/or by cooperating components of one or more of the head mount 15, cannula 20 and/or the probe 30. The MRI coils built on any of the targeting cannulas 20 herein, or on the mount 15, probes 30, sheath 34, multilumen insert 300, alone or in combination, can include one or more imaging coils of the following types: loop, solenoid, loopless, dipole antennas, saddle, and birdcage coils. These can be actively tuned and decoupled, inductively coupled, etc.

In some embodiments, the antenna 30a has a focal length or signal-receiving length of between about 1-5 cm, and typically is configured to have a viewing length to receive MRI signals from local tissue of between about 1-2.5 cm. The MRI antenna 30a can be formed as comprising a coaxial and/or triaxial antenna. However, other antenna configurations can be used, such as, for example, a whip antenna, a coil antenna, a loopless antenna, and/or a looped antenna. See, e.g., U.S. Pat. Nos. 5,699,801; 5,928,145; 6,263,229; 6,606,513; 6,628,980; 6,284,971; 6,675,033; and 6,701,176, the contents of which are hereby incorporated by reference as if recited in full herein. See also U.S. Patent Application Publication Nos. US 2003/0050557; US 2004/0046557; and 2003/0028095, the contents of which are also hereby incorporated by reference as if recited in full herein.

As noted above, the probe 30 can include at least one electrode 31 that can operate as a sensing electrode (i.e., for micro-electric recording). The at least one electrode 31 can be more than one electrode and/or the electrode 31 may be able to both sense and stimulate. For neural uses, different regions in the brain provide different sensed intensities, frequencies and/or pitches (typically readings of between about 1-4 microvolts) which are identifiable and can allow a clinician or software additional data to confirm that the probe 30 and/or lead 35 reaches a proper target location.

As will be discussed further below, the mount 15 can be in communication with a drive system that can move the mount in desired directions, such as rotate, adjust pitch or translation, and may advance and/or retract the cannula 20 and/or probe 30.

Figure 3A:
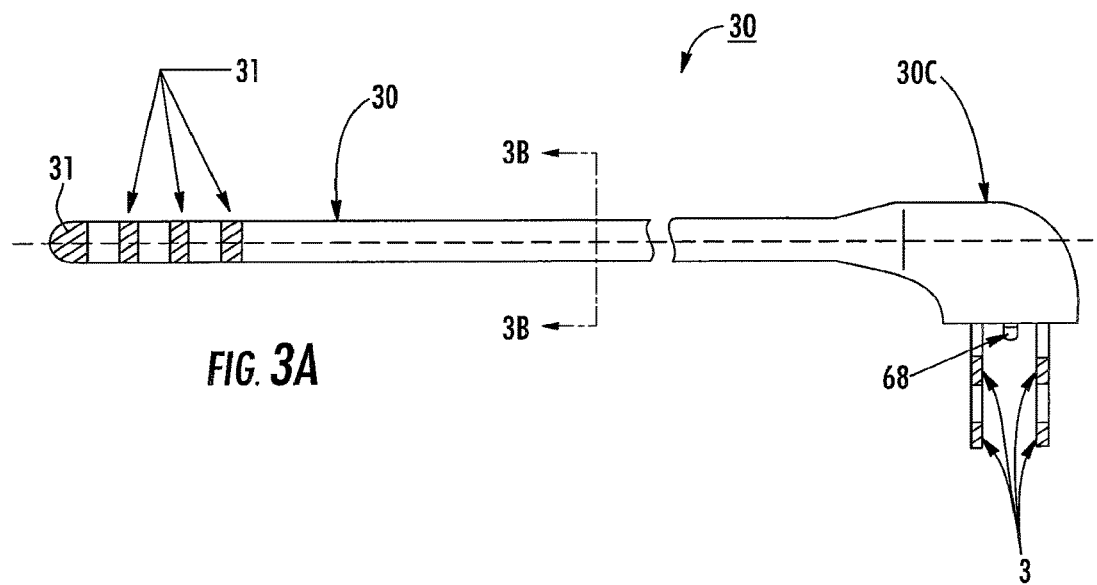
FIG. 3A is a side view of a stimulation lead according to embodiments of the present invention.
Figure 3B:
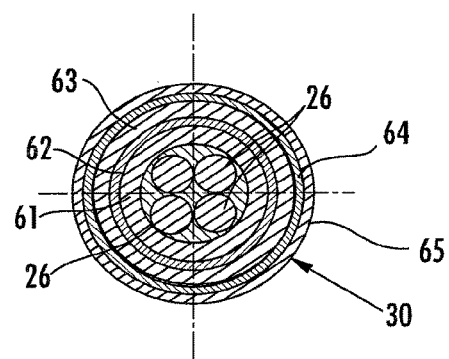
FIG. 3B is a section view of the device shown in FIG. 3A, taken along line 3B-3B.

FIGS. 3A and 3B illustrates that, in some embodiments, the core of the probe 30 can be configured to hold at least one (shown as a plurality of) axially extending conductor(s) 26, typically a respective one for each electrode 31. In other embodiments, greater or fewer numbers of conductors than electrodes 31 may be used. As noted above, the probe 30 can be a multi-purpose probe. The conductors 26 may be static and held generally encapsulated in a first insulating dielectric layer 61. In other embodiments, the conductors 26 may be held in the first dielectric material 61 so that they can translate in the axial and/or generally outward or transverse directions. Referring again to FIG. 3B, an axially extending first shielding layer 62 can surround the first dielectric layer 61. A second axially extending insulating dielectric layer 63 can surround the first shielding layer 62. A second axially extending shielding layer 64 can be electrically connected to the first shield layer 62 (that may also be called a primary shield layer) at a proximal end portion thereof. An outer polymeric insulator layer 65 can surround the inner layers 61-64 while terminating to typically expose the electrodes 31 to allow stronger stimulation contact during operation. The conductors 26 extend from the connector 30 to the respective electrode 31. The probe 20 includes an electrical ground 68 and the connector 30 connects the ground 68 and each electrode 31. As shown, the connector 30 can include connector prongs (shown as two, but additional prongs may be used), each having a connection for a respective conductor 26 that merges into a respective electrode 31. Where combinations of electrodes 31 are used, the conductor 26 can connect to two or more electrodes 31 and share a common connector 30e.

As discussed above, the probe 30 can be configured with an imaging coil 30a to collect MRI signal data for MRI imaging/data collection capability and include at least one discrete electrode 31, which can be a directional electrode (directional/volumetric specific electrode) to be able to controllably generate different stimulation field patterns in different directions in situ. Directional electrodes may allow a more precise stimulation therapy that can be adjusted based on a patient's particular neural circuitry and/or physiology. For additional description of probes and/or components thereof, see, e.g., PCT/US/2005/026508, the contents of which are hereby incorporated by reference as if recited in full herein.

For example, once the stimulation lead 35 is inserted to a target neural region in the brain, the stimulation lead can be activated to use at least one electrode 36, which provides the desired therapeutic response while minimizing undesired responses. It is contemplated that a more precise stimulation of neural tissue that is directionally specific can stimulate only desired neural circuitry and/or tissue. The stimulation may be output to stimulate target cellular or subcellular matter. In some embodiments, the stimulation can generally be transmitted within about a small stimulation volume. The probe 30 with an MRI antenna 30a can help position the probe to between about 0.5 mm to about 1.5 mm of a target neural space, and in other embodiments, between about 0.1-0.5 mm. Once in the target neural space, the stimulation electrode 31 and/or stimulation lead electrode 36 can generate a locationally precise, controlled directional volumetric stimulation that may allow an increase in therapeutic efficacy for different disorders, diseases or impairments.

Figure 3C:
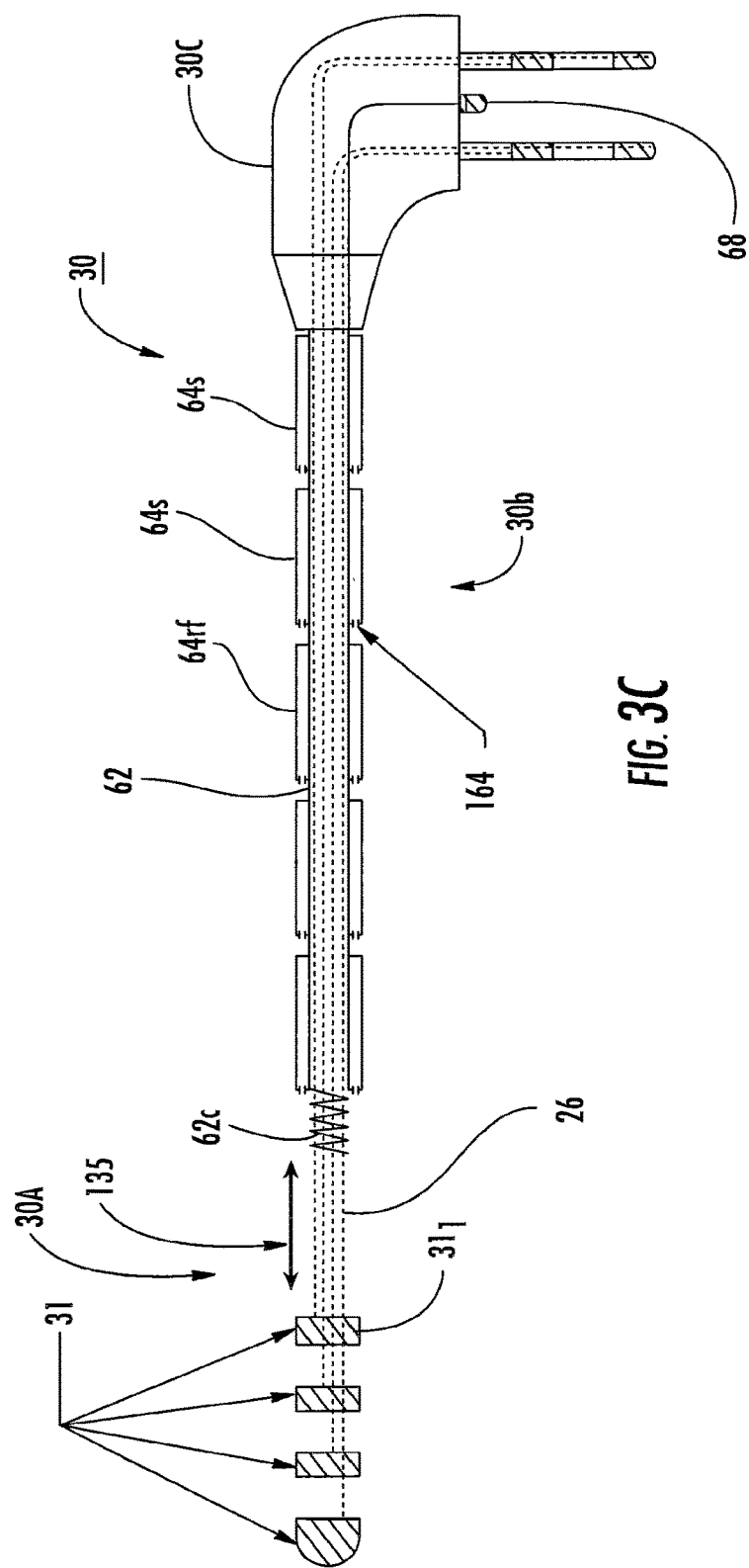
FIG. 3C is an electrical schematic diagram of the device shown in FIG. 3A according to embodiments of the present invention.

FIG. 3C illustrates an electrical schematic of the probe 30 shown in FIGS. 3A and 3B. As shown, the primary or first shield layer 62 axially terminates at a distal portion of the probe in advance of the first electrode 31. Although shown with a plurality of electrodes 31, a single electrode or fewer or greater numbers may be used. The primary shielding 62 may be formed into a coil 62c at a distal portion of the probe 30. In other embodiments, the primary shielding 62 can terminate without coiling (not shown). In yet other embodiments, the shielding 62 may be coiled a distance past one or more electrodes 31, including all the way forward to the distal end portion (not shown). In some embodiments, a respective conductor 26 can extend to a corresponding electrode 31, with the longest conductor 26 corresponding to the more distal electrode 31. The conductor(s) 26 may be substantially linear along the length in the probe body as shown, or may be coiled. If coiled, the coil for the conductor 26 may be at a distal portion, just before the respective electrode 31, which may increase signal (not shown). Each electrode 31 is typically in communication with at least one of the insulated conductors 26. At the proximal end of the probe 20, the conductors 26 are connected to a connector 30 so as to be connected to the implantable signal generator 50 or to the interface circuit 40 during MRI guided probe/lead/cable placement. These insulated conductors 26 are typically covered with a polymeric insulator sleeve 61, and a conducting material is cylindrically layered to form the first shielding layer 62 over the insulator. This shielding 62 is terminated proximal to the electrodes and is not in electrical contact with the conductors or the electrodes. A second insulator/polymeric/dielectric layer 63 further insulates this shielding to form a multi-core coaxial type cable system with an impedance that is typically between about 10-1000 ohms. The RF chokes 64rf can be integrated or built into the shielding 64 in the form of a second shielding, which is not continuous and has multiple sections each $\lambda/4$ or less in length.

As shown in FIG. 3C, at the proximal end, each section or segment 64s is connected to the primary shielding 62, and the distal end may not be electrically connected to the primary shielding 62, or may be connected with a capacitance 164 in between the primary and secondary shielding, 62, 64, respectively. A top insulator/polymeric layer 65 can be used to insulate the probe body 30b, except for the electrodes 31.

As shown by the axial arrow in FIG. 3C, the antenna 30a can include an MRI active portion 135 that may extend between a location where the primary shield 62 terminates and the first electrode $31_1$. However, as noted above, other antenna configurations may also be used. As shown, the second shield layer 64 comprises a plurality of axially spaced apart RF chokes 64rf. The term "RF chokes" refers to an electrical configuration formed in a shielding layer and/or internal electrode lead configuration that provides an electrical disconnect and/or an electrical length of less than or equal to $\lambda/4$ (from the perspective of external electromagnetic waves) to inhibit the formation and/or propagation of RF-induced current or standing waves in an AC (alternating current, e.g., diathermy applications) or RF exposure environment. The physical length that provides the electrical wavelength may vary depending on the materials used in fabricating the probe (such as dielectric constant) and the magnetic field in which it is used. In some embodiments, the probe 30 has a physical length that is greater than 10 cm, typically between about 20 cm to about 150 cm. In some embodiments, the implantable lead segment 35 can also include RF chokes 64rf formed along target regions or along substantially the entire implantable length. In the embodiment shown in FIG. 3C, the RF chokes 64rf comprise a plurality of disconnects of the shield 64 and/or discrete electrically isolated second shield segments. In other embodiments, the RF chokes 64rf can include a series of axially spaced apart Balun circuits or other suitable circuit configurations. See, e.g., U.S. Pat. No. 6,284,971, and co-pending U.S. Patent Application Publication, US-2006-0252314-A1, the contents of which are hereby incorporated by reference as if recited in full herein, for additional description of electrical leads.

As shown in FIG. 3C, the second shield layer 64 may be coupled to the first shielding layer 62 at opposing ends of the segments 64s. As shown, one end (typically the proximal end portion) of the disconnected segment 64s is directly coupled to the shielding layer 62 and the other end (typically the distal end portion) is capacitively coupled to the first shielding layer 62. Each segment 64s may be configured to engage the first shield layer 62 in the same manner or in an opposing different electrical manner (not shown).

Figure 4A:
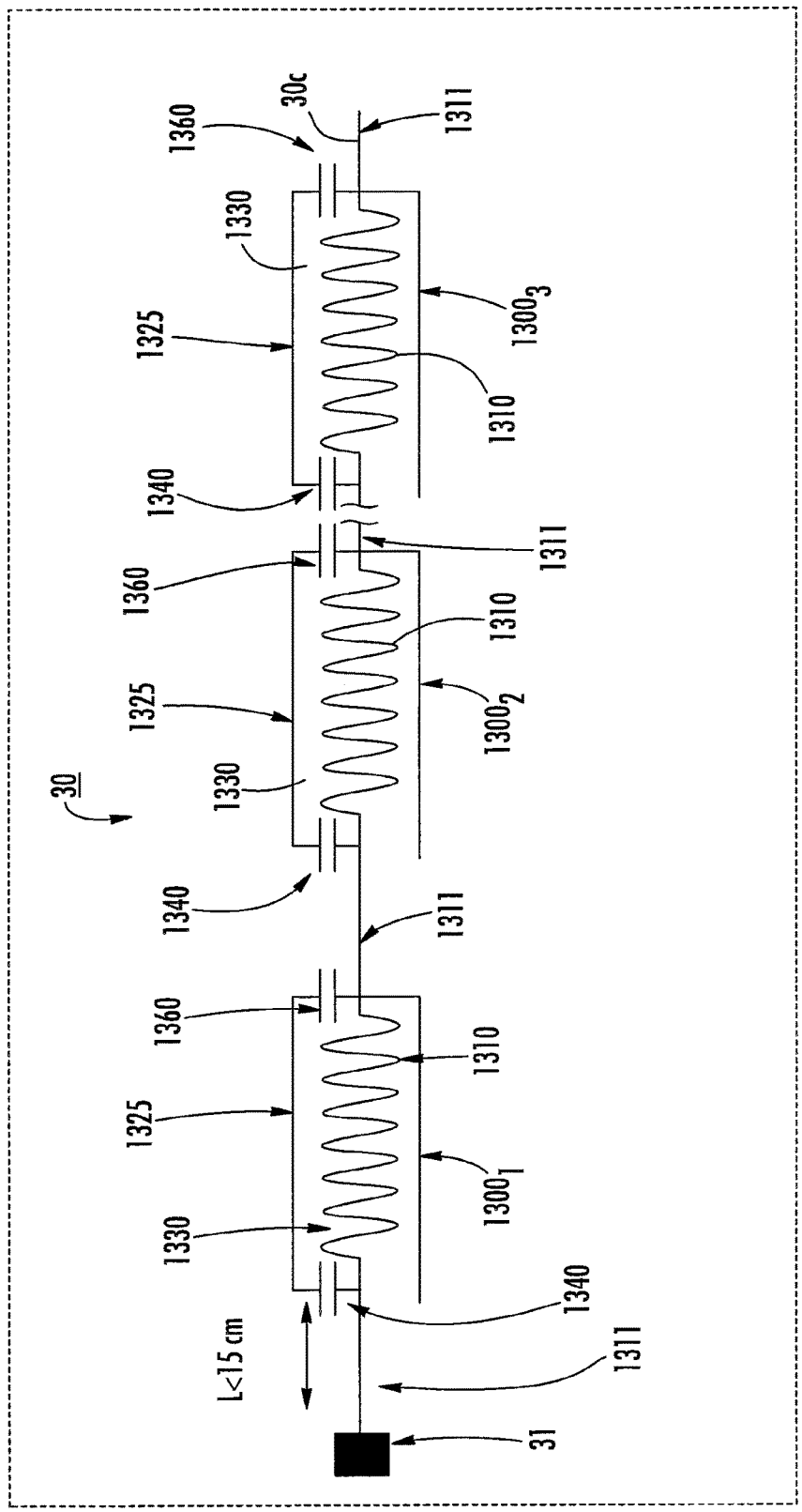
FIG. 4A is a schematic illustration of a long lead with a plurality of axially spaced apart RF traps along a length of a conductor or lead according to embodiments of the invention.
Figure 4B:
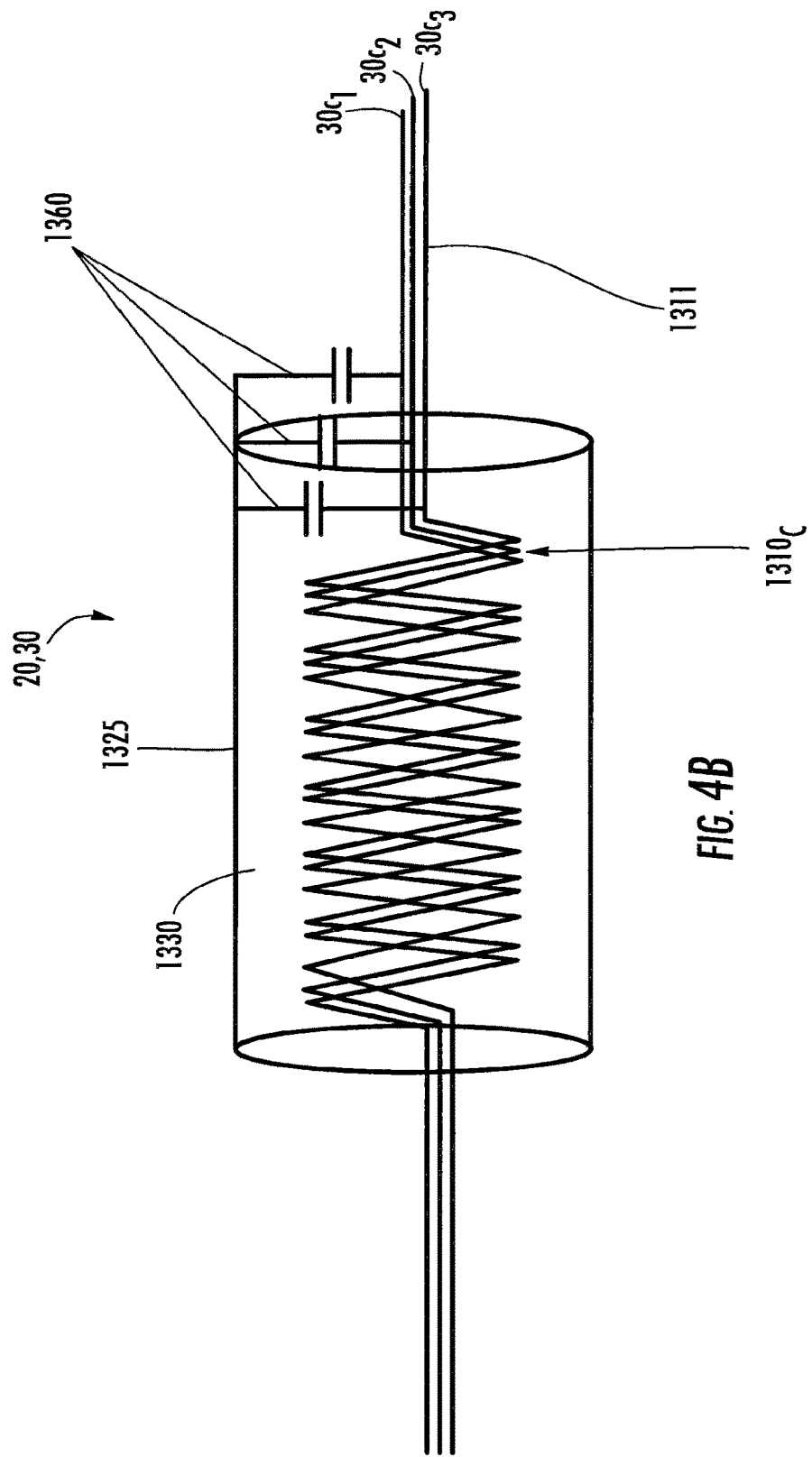
FIG. 4B is a schematic illustration of a lead system with RF traps having co-wound conductors in a common shield according to embodiments of the invention.

FIGS. 4A and 4B illustrate additional exemplary electrical safety circuits that can be used in combination with other RF safety features described herein or alone, for probes 30 or other leads or components that may be exposed to MR systems. Thus, although described as used with respect to probe 30, the circuit and conductor configurations may be used with other components or devices associated with embodiments of the invention.

As shown in FIG. 4A, a conductive lead 30c can include a plurality of high impedance segments 1300 that can be positioned along the length of the lead system 30 at regular or irregular intervals, but typically so that the spacing provides an electrical length of less than about λ/4 therebetween. The RF traps 1300 are placed less than about λ/4 apart, where λ is the wavelength in the medium of the operating frequency, to electrically break the long conductor into multiple sections.

The probe 30 or other member can include multiple high impedance sections or segments 1300 along the length thereof. The high impedance sections or segments can be created by arranging the components of the medical device, i.e., the conductor, etc. as an RF trap. These high impedance RF traps inhibit the flow of induced RF current (at the frequency to which the RF trap is tuned) and prevent it from heating tissue adjacent to the electrodes, thus minimizing or preventing RF induced tissue damage. Since the physiological and stimulation signals are at low frequencies (KHz range), the RF trap allows the lower frequency signal(s) to go through, trapping only the higher frequencies of interest to which the traps are tuned.

As shown in FIG. 4A, the conductor 30c can be in electrical communication with the shield at the distal portion of the high impedance segment 1300 via a tuning capacitor 1340. The high impedance segment 1300 (e.g., RF trap) can be tuned to a MRI frequency. The segment 1300 can also be configured so that the conductor 30c at the proximal end portion of the segment 1300p is connected to the shield 1325 via a capacitor 1360. One or more of the different high impedance segments 1300 (shown as $1300_1$, $1300_2$, $1300_3$) may be tuned to different MRI frequencies (i.e., 64 MHz and 128 MHz or other standard operating frequencies of commercial MRI scanners). The impedance of the segment 1300 can be at least 400 Ohms, typically greater than about 450 Ohms. The at least one high impedance segment 1300 can be placed at between about 0.1-12 cm from the electrode(s) 31. The lead 30c can be configured with a straight segment 1311 that merges into the coiled segment 1310.

In operation, the RF trap(s) 1300 with the shield 1325, inductor 1310 and tuning capacitor 1340 form a high impedance parallel resonant circuit at the desired frequency to block RF currents along the conductor. The tuning capacitor can include one or more of a discrete capacitor 1340 and/or stray capacitance between the inductor 1310 and the shield 1325.

FIG. 4B illustrates that a plurality of conductors (shown as three) $30c_1$, $30c_2$, $30c_3$ can be co-wound (see element 1310c) and reside within a common flexible shield 1325. Each conductor $30c_1$, $30c_2$, $30c_3$ can be electrically connected to the shield 1325 at a proximal portion thereof, directly or indirectly, such as using a respective capacitor 1360 as shown. The capacitor 1360 can provide an RF short. The high impedance segments 1300 (RF traps) are placed less than a λ/4 apart from each other at the desired frequency. The coiled segments of the conductors can define inductors and can each connect a different distal electrode.

When multiple high impedance segments 1300 (using, for example RF traps) are incorporated over the length of a device such that the distance between two adjacent traps is less than one-quarter wavelength, this effectively breaks the long conductor into multiple sections, each shorter than a quarter wavelength. The RF current induced on a conductor is a function of length of the conductor at the RF frequency, and when the conductor is shorter than a quarter wavelength, the RF current induced is not large enough and may not cause undue RF deposition RF induced-treating of the tissue.

In some embodiments, as shown for example in FIG. 2D, the probe 30 can be configured with one or more lumens 39 and exit ports that deliver desired cellular, biological, and/or drug therapeutics to the target area, such as the brain. The probe 30 may also cooperate with and/or incorporate biopsy and/or injection needles and/or ablation means.

Embodiments of the present invention can provide a multi-function MRI safe lead or probe 30 that can operate at least bimodally: namely, during MRI procedures to obtain MRI signal from local tissue in vivo and to stimulate the target tissue during an MRI procedure. The system 10 can be configured for use in any suitable MRI scanner, such as low field magnets (typically about 0.5-1.0 T fields), to a conventional 1.5T magnet or higher, such as 2T, 3T or even higher. MRI scanners are well known to those of skill in the art and include, but are not limited to, SIEMENS and GE MRI systems.

Configuring a probe 30 to function both as an MRI antenna 30a (alone or cooperating with other components) and a stimulation and/or recording probe 31 may reduce the time needed to place the electrodes in the desired location, provide for increased accuracy in location and/or reduce the number of times a device is inserted into the brain or other target region.

Figure 5:
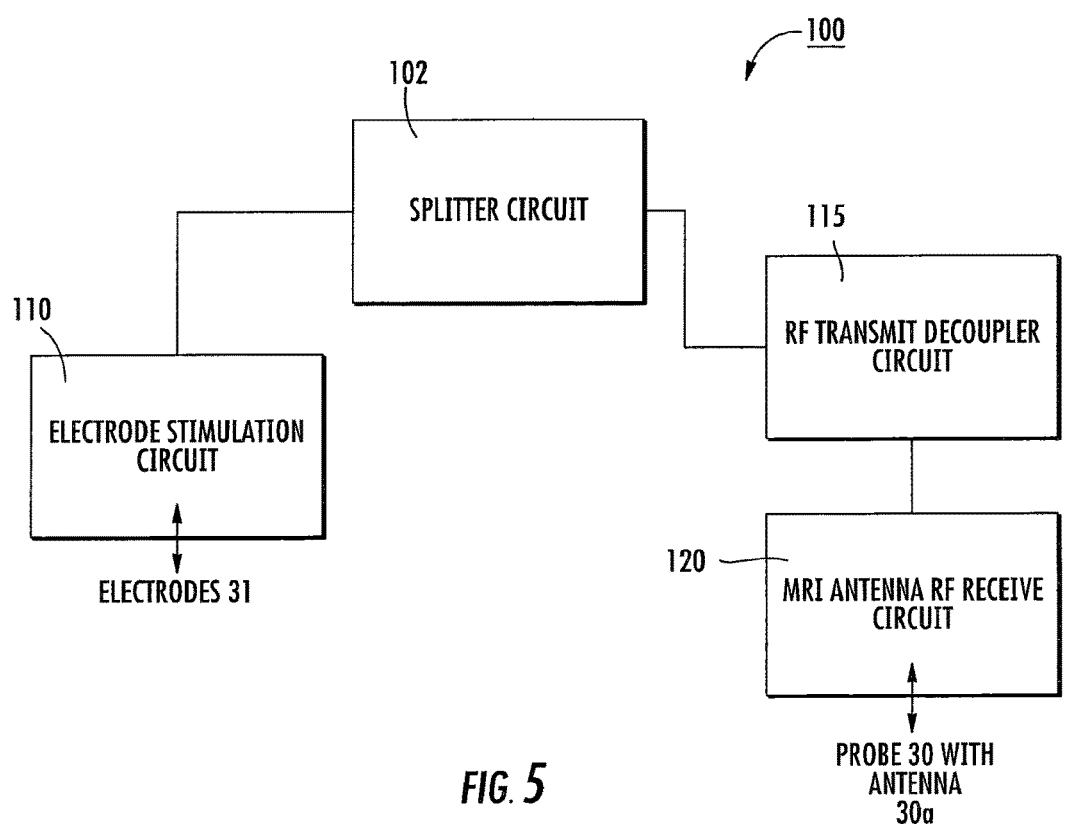
FIG. 5 is a block diagram of a bimodal lead operating circuit according to embodiments of the present invention.

FIG. 5 illustrates a circuit 100 that can provide the bimodal operation of the probe 20. As shown, the circuit 100 includes a splitter circuit 102 that is in communication with an electrode stimulation circuit 110 that provides the stimulation to the electrode(s) 31. The splitter circuit 102 is also in communication with an RF transmit decoupler circuit 115 that is in communication with an MRI antenna RF receive circuit 120 and the antenna 30a on probe 30. Certain or all of the components can be held in the MRI scanner interface 50. In other embodiments, certain or all of the components of the circuit 100 can be held in the connector 32.

Generally stated, in some embodiments, the probe 30 can have at least two primary operational modes with different electric transmission paths, which are electrically directed using the splitter circuit 102. In operation, during an MRI procedure, an RF excitation pulse is transmitted to a subject. The MRI antenna 30a is decoupled during RF transmission, then operative during a receive cycle to receive signal from local tissue. The at least one stimulation electrode 31 is typically isolated via the splitter circuit 102 so that only the MRI antenna portion of the probe 30 is active. The MRI interface 50 (FIG. 1) communicates with the MRI scanner and may be configured with a supplemental port to allow the implantable pulse generator or another stimulation source to connect thereto, thereby allowing the IPG or another stimulation source to stimulate the electrodes without decoupling the interface during the placement procedure (confirming proper placement). In some embodiments, the MRI interface 50 can include a stimulation and/or sensing mode that operates the electrodes.

During MRI-guided clinical implantation of the probe 30, the probe 30 can first be used as an MRI antenna to provide high resolution imaging of the target internal anatomy (such as neural tissue) and to locate the position of the electrodes 31 in the body by obtaining MRI signals and, hence, images that are acquired by the external coils and/or internal MRI antenna. The electrodes 31 can also be used to assess location via acquiring electrical signals from and/or stimulating the target (neural) anatomy.

Figure 6:
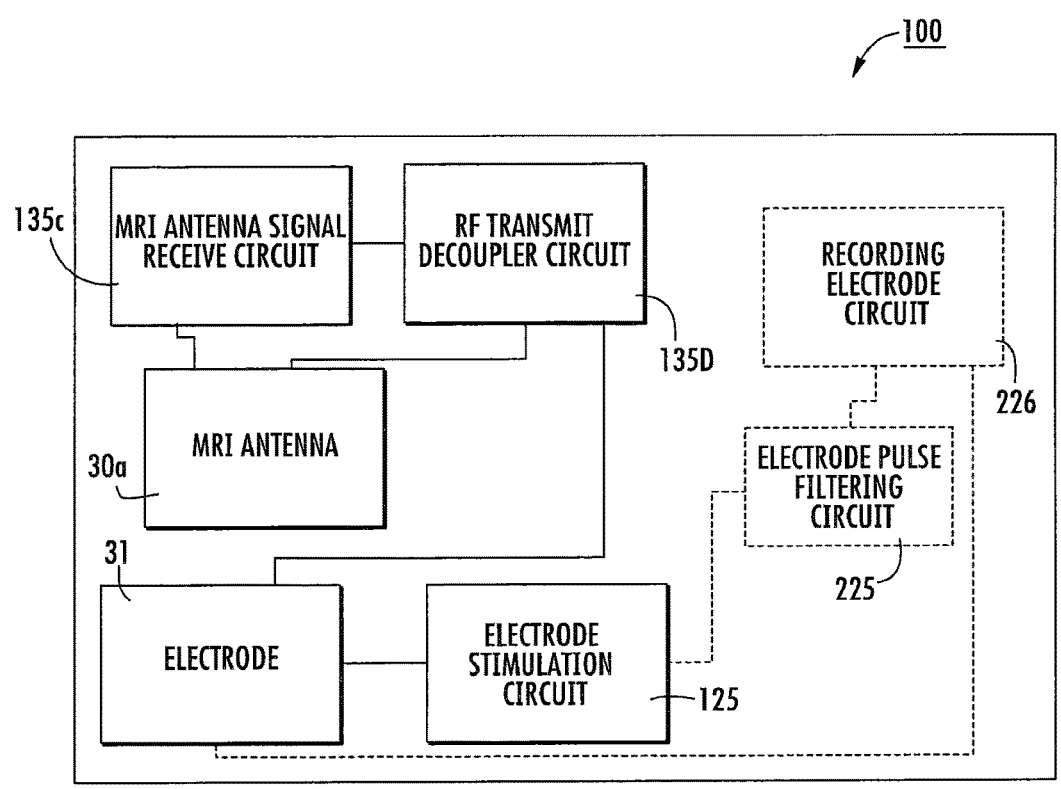
FIG. 6 is a block diagram of another operating circuit according to embodiments of the present invention.

FIG. 6 illustrates a different circuit 100 that may be used to provide the different operational modes of the probe 30. FIG. 6 illustrates an MRI antenna receive circuit 135*c* that receives the MRI responsive signal from local tissue and an RF transmit decoupler circuit 135D that can decouple the antenna 30*a* and the electrodes during RF transmission. The circuit 100 also includes an electrode stimulation circuit 125 that provides the stimulation pulses to the electrode(s) 31 and can include an electrode pulse filtering circuit 225 and a recording electrode circuit 226 used to gather local microelectric signals.

Figure 7A:
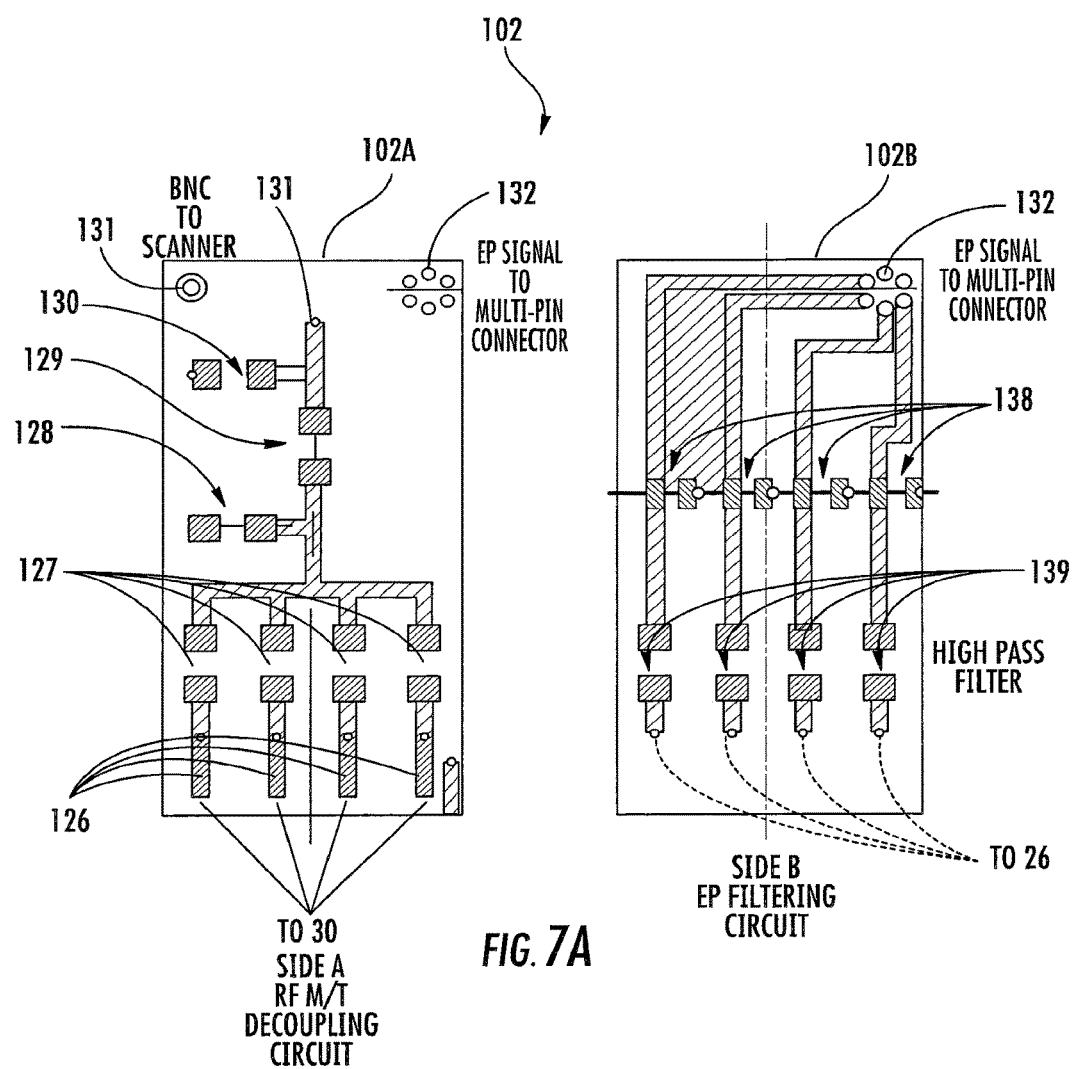
FIG. 7A is a schematic illustration of a splitter circuit according to embodiments of the present invention.
Figure 7B:
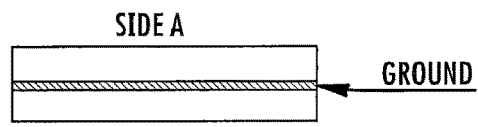
FIG. 7B is an end view of the circuit shown in FIG. 7A.

FIG. 7A is a schematic illustration of an exemplary splitter circuit 102 that provides different transmission paths for signals operating in the imaging (MR signal) mode and in the sensing microelectrical mode according to some embodiments of the present invention. FIG. 7A illustrates that the circuit 102 can have two sides, 102A, 102B, respectively that substantially overlie each other as shown in FIG. 7B with a ground plane therebetween. Side A 102A includes the active path of the MRI antenna 30*a* with matching and tuning components including decoupling capacitors 127, conductor connections 126 (to respective conductors 26), an input (shown as a BNC input) to the MRI scanner 131, an input to a multi-pin connector for an electrode pulse signal 132 (EP signal) a PIN diode 128, a matching tuning inductor 129 and a matching/tuning circuit capacitor 130. Side B 102B is the electrode operational circuit configured to act as a high pass filter. As shown, the respective electrical transmission paths to the conductors 26 include capacitors 138 (shown as 1000 pF capacitors) and 64 MHz RF blocking inductors 139. The blocking inductors 139 can be changed to block the frequency of the MRI system in use (higher frequencies for higher field magnets, i.e., for proton imaging, 96 MHz for 2T, 128 MHz for 3T). It is noted that components of the exemplary circuits are shown with respect to side A or B for ease of discussion, but certain of the circuits (or the entire circuit) may reside on a different side than that shown (and are not required to be on one side).

In some embodiments, the probe 30 can be placed in the brain, such as in the subthalamic nucleus or other deep brain target via a burr hole formed in the skull. MR imaging using the probe 30 can guide an increased accurate placement in the thalamus or other desired anatomies. Further, the electrical signals from the local tissue can be analyzed and evaluated to determine a final location of the electrodes 31 for stimulation electrodes 36 on lead 35. During this time, the probe can be connected to the MRI scanner interface 50 that can include a matching-tuning decoupling circuit 40 (FIG. 1A), and a splitter circuit to separate MR signal from the electrical signals generated by the local target tissue. Once the probe system is appropriately located in the desired anatomy, the stimulator can be connected for physiological confirmation of the function. A telescopic system to lengthen or shorten the lead may be implemented in the proximal section of the probe, since diameter/profile may not be a significant concern in this region.

As noted above and shown with respect to FIG. 2D, the probe 30 may have one or more lumens 39 configured to deliver cellular and/or biological therapeutics to the desired neural tissue. The delivery lumens 39 may be medially located or be formed off-center, such as a channel in a sidewall of the device (not shown). The lumens 39 may be configured to receive an extendable needle that may exit the probe from the distal end or from the sides, proximal, distal, or even through the electrodes to precisely deliver cellular/biological therapeutics to the desired anatomy target. This delivery configuration may be a potential way to treat patients, where the cellular/biological therapeutics are delivered into the desired anatomy and the neurotransmitter/signal generator paces the cells to modify their function. In this way, even if the signal generator fails, the cells (stem cells) may differentiate and take over the function. MRI can be used to monitor the efficacy of the therapy in the brain.

The stimulation lead 35 and probe 30 can be sized and configured to have substantially the same cross-sectional area or one may cooperate with a sleeve so as to be held snugly in the sheath 34 and/or targeting cannula 20 and/or mount 15. For example, in some embodiments, a non-conductive elastomeric sleeve (not shown), coating or other configuration can be used to size the stimulation lead 35 and/or probes 30 to snugly fit the cannula 20 as desired. In other embodiments, an insert can be used to adjust the size of the holding port or lumen of the cannula 20 to correspond to that of the probe in use (also not shown). The cannula 20 and both lead/probes 30, 35, respectively, can be MRI-compatible and may include the RF-safe circuits such as RF chokes, Balun circuits and/or other RF safe configurations. See, e.g., co-pending PCT patent application identified by U.S. Pat. No. 6,284,971, the contents of which are hereby incorporated by reference as if recited in full herein.

In some embodiments, the antenna portion of the probe 30 can define a relatively small MRI receiver length "L," such as less than about 5 cm, typically between about 1-2.5 cm as noted above. As before, the antenna 30*a* can be any suitable type and is not limited to a coaxial cable type (including, for example, a dipole or loopless antenna as discussed above). The probe 30 can be configured to define the antenna 30*a* alone or in combination with other components. For example, in some particular embodiments, the cannula 20 or sheath 34 can form a shielding layer. In some embodiments, the cannula 20 may comprise a polymer and may include MRI compatible conductive material, such as Nitonal.

In some embodiments, one or more of the mount 15, a multi-lumen insert 300 (FIG. 12A) or cannula 20 can be configured to cooperate with the probe 30 to define an MRI antenna 30*a*. The insert 300, mount 15 and/or cannula 20 can provide a ground and positive signal path. With reference again to FIG. 3C, the cannula 20 can provide one or more insulating layers 61, 63 or shielding layers 62, 64 with the antenna probe 30 providing at least one conductor 26 and potentially one or more of the insulating layer 61 or shielding layers 62, 64. In particular embodiments, the cannula 20 provides the secondary shield layer 64 and may include RF chokes 64*rf*.

As will be discussed further below, the system 10 can include circuits and/or modules that can comprise computer program code used to automatically or semi-automatically carry out operations to stimulate, sense signals in vivo, and/or determine a probe location, a scan plane and localization trajectory(ies) and the like. The module can be in communication with the probe 30.

The system 10 can be configured to electronically obtain and monitor patient response data can include electrophysiological input from sensors held on the body, such as, but not limited to, heart rate, blood pressure, movement sensors to detect an increase or decrease in patient movement (to detect shaking or tremors in limbs and the like), fMRI data, local cellular audio and/or electrical activity (such as using a sensing electrode), or other patient response data. Supplemental external or internal sensing electrodes may also be positioned on/in the patient and automatically input to a module to assess whether detrimental responses or inadvertent activation of non-target neural circuitry may be stimulated. The module may also be configured to accept input of patient response data (that may be input by a clinician using a computer entry screen) to input when detrimental or advantageous responses are indicated. The patient response data can be input as an input variable for correlation analysis with other input variables. Where used, the clinician may enter data using a remote or local computer, a portable communications device, or other wireless or wired device. However, in some embodiments, it may be desired to carry out the evaluation in a substantially automated manner, allowing for a potentially faster stimulation evaluation protocol and patient-specific stimulation determination.

Figure 8:
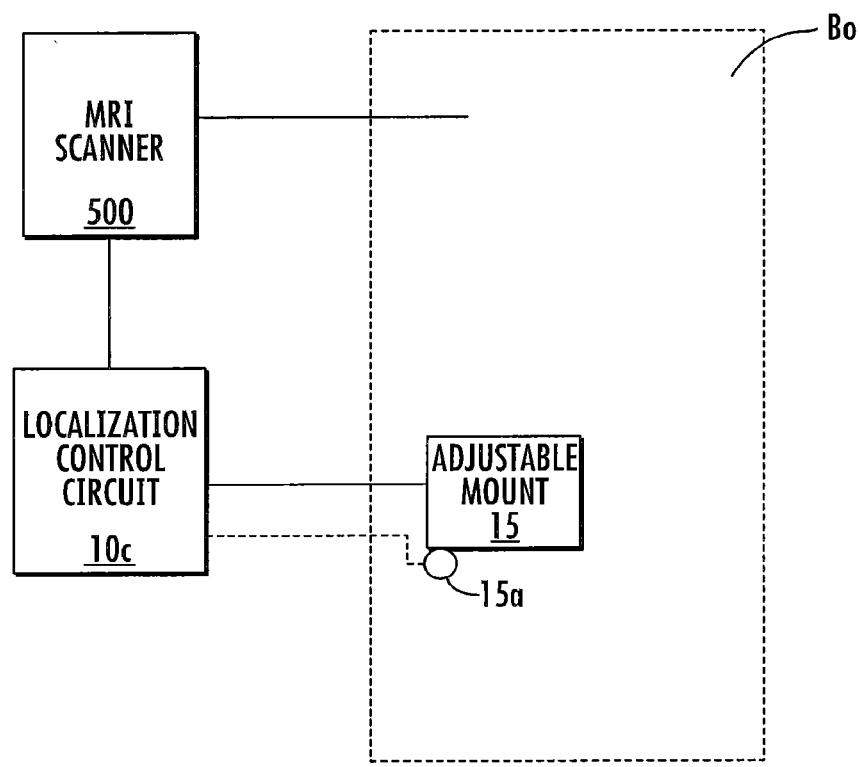
FIG. 8 is a schematic illustration of a localization system according to embodiments of the invention.

In some embodiments, as shown in FIG. 8, the system 10 can include an automated Localization Control Circuit 10c that communicates with an MRI scanner 500 and, optionally, the adjustable mount 15 that resides in the magnetic field $B_o$ of the MRI scanner. The Circuit 10c can direct the MRI scanner 500 to run certain imaging sequences to identify the scan plane that an elongate member resides in, in 3D MRI space, held in the mount 15. The system 10 may interface with the MRI scanner and provide input to drive the scanner 500 to the desired imaging planes, as they are prescribed on the system (circuit and/or software) as opposed to the scanner 500. Alternatively, the system 10 (circuit and/or software) can provide information to an operator that allows the scanner operator to select and initiate the imaging planes identified by the system 10.

The Circuit 10c can include a signal processor configured to analyze pixel or voxel data to define the scan plane automatically and relatively quickly from image data that renders the elongate member with higher intensity (greater SNR) in a target region of a patient. The system can cooperate with an MRI scanner to identify the scan plane in which an elongate targeting marker, such as a sheath 34, insert 300, targeting cannula 20 and/or probe 30 reside. That is, the elongate member is MRI-visible and configured to have increased SNR relative to other features in the image such that data review of pixels or voxels can define the location of the member and identify the scan plane associated therewith.

The Circuit 10c can determine what adjustments are suitable to move the mount 15 to a desired configuration so as to define the targeting or desired access path trajectory to intersect with target tissue.

Figure 9:
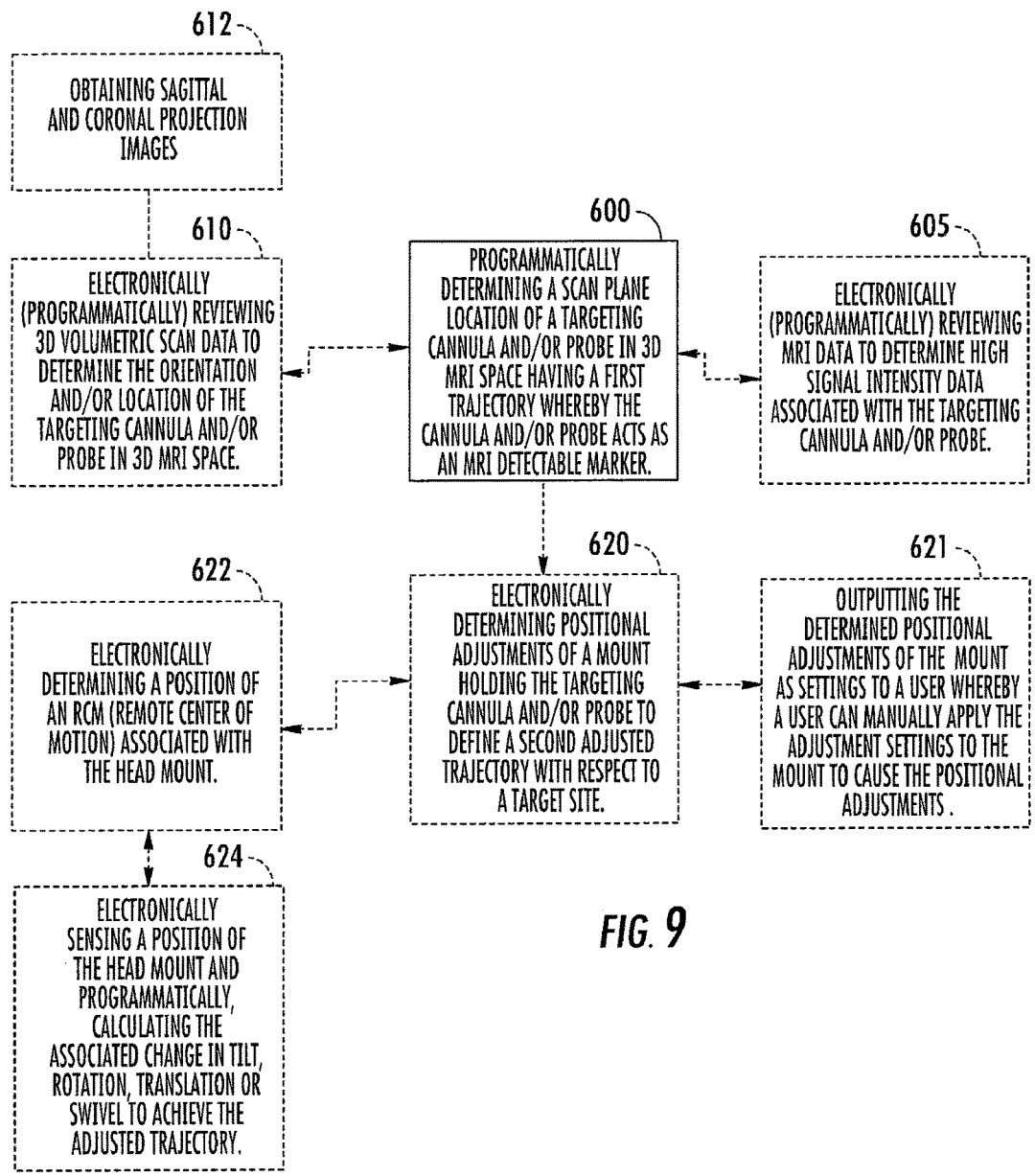
FIG. 9 is a flow chart of operations that can be used to carry out embodiments of the invention.

FIG. 9 is a block diagram of some operations that may be carried out according to embodiments of the invention. As shown, a scan plane associated with the elongate targeting cannula and/or probe (or other MRI visible elongate member) residing in 3D MRI space and having a first trajectory can be programmatically, typically automatically, determined (block 600), whereby the cannula or probe acts as an MRI detectable marker. That is, the system 10 can be configured to identify and provide 3D coordinates of one or more of the elongate member the target, the burr hole location, etc. in the MRI space. This data can direct which imaging plane to use to observe the probe and/or access path trajectory or direct the operator to prescribe the imaging plane on the scanner.

In some embodiments, the scan plane can be determined by electronically (programmatically) reviewing MRI data (typically from at least two images taken at oblique angle images) to determine high signal intensity data associated with the targeting cannula and/or probe (or sheath or other elongate member) (block 605). The signal intensity data may be of pixels or voxels. In some embodiments, the methods may also or alternatively include electronically (programmatically) reviewing 3D volumetric scan data for high signal intensity data to determine the location of the target elongate component, i.e., targeting cannula and/or probe in 3D MRI space (block 610).

In some embodiments, after the scan plane is determined, positional adjustments (e.g., degrees of rotation, or translation) of the mount holding the cannula and/or probe (or other member) can be electronically determined to generate a second adjusted trajectory to the target site (block 620). The adjustments can be output to a user to allow the user to physically manually change the mount settings using visual indexing or electronic inputs (touch screen or other input means) to allow a user to alter the mount configuration (block 621). Alternatively, the system can be fully automated so that the new adjustments can be automatically applied via an automated drive system. That is, a position of an RCM associated with a head mount can be electronically determined (i.e., registered in an image) (block 622). A calibrated "current" or "start" position of the head mount can be electronically determined and registered to a first trajectory in 3D MRI space using transducers, optical encoders and the like. A change in one or more of rotation, tilt or translation of the mount can be programmatically calculated to achieve the desired adjusted trajectory (block 624).

The system 10 can also include an automated MRI scan plane and trajectory determination module that can define position adjustment data for the mount 15 (e.g., head mount or other mount type). The adjustment data can be output to a clinician to define the frame adjustment inputs (i.e., coordinates) to adjust the trajectory of the frame to the desired intersection with target tissue. In other embodiments, the adjustment data can be used to automatically adjust the frame position on the patient using automated position or adjustment drive systems to obtain an adjusted trajectory without requiring manual input.

In some embodiments, the system 10 can include a Graphic User Interface (GUI) that allows a clinician to define a desired trajectory and/or end position on a displayed image, then can electronically convert the orientation/site input data programmatically to generate the frame position data (not shown). The GUI can include an interactive tool that allows a clinician to draw, trace or otherwise select and/or identify the target treatment site and/or access path trajectory. The system 10 can then be configured to identify the lumen of choice and/or adjustments to the mount 15 that is most likely to achieve this trajectory.

In some embodiments, the system 10 includes a user interface that can be configured to carry out one or more of the following: (a) electronically determine the location of the targeting cannula/frameless headmount and a trajectory associated therewith; (b) based on the determined location of the frameless headmount, determine adjustments to the headmount so that the desired trajectory is achieved, and provide the adjustment/setting information to an operator (or automatically adjust the settings for automated systems with feedback control); and (c) display MRI images with the projected trajectory and intersection point(s) on that will be followed if the interventional/surgical device/lead is advanced using a defined position of the headmount.

In some embodiments, the location and orientation of one or more elongate marker(s) (e.g., targeting cannula) in 3D MRI space may be programmatically determined by obtaining sagittal and coronal projection images, applying high intensity filtering, then using image recognition (such as an image recognition mask) and/or linear regression to find coordinates of the elongate marker (e.g., cannula) in space.

Alternatively or additionally, the location and orientation of the above-described elongate marker(s) (e.g., targeting cannula) in 3D MRI space may be determined by obtaining a 3D volumetric scan, applying high intensity filtering, then using 3D image recognition (such as an image recognition mask) and/or linear regression to find coordinates of the elongate marker (e.g., cannula) in space.

More particularly, the location and orientation methods described above with respect to the projection images can be carried out as described below. First, sagittal and coronal projection images can be taken of the region encompassing the marker (e.g., targeting cannula). Next, these image arrays are "padded" by adding zeros to the left, right, top, and bottom of the image arrays so that an image recognition mask can be effectively applied to the edges. These images are processed so that points in the arrays with signal intensity less than a given threshold are assigned a value of 0, and points above the threshold are given a value of 1. Then, an image recognition mask A (an a*b array) that traces out the shape of the marker (e.g., targeting cannula) for a given angle is applied to the images as follows:

a. Starting at the point (0,0) in the image I (which is an m by n array) calculate the sum of the values of $I(x,y)*A(x,y)$ for x:[0,a], y:[0,b].
b. Repeat at points (1,0), (2,0), . . . , (m−a,0) in A.
c. Repeat in rows 1, 2, . . . , n−b in A.

After these steps are completed for a filtering mask at a given angle, repeat with a mask where the cannula is to be recognized at a different angle. Repeat the process for suitable angles (such as all reasonably possible angles). The point where a mask creates the highest summation at a given angle can be recognized as the lower left corner of the rectangle defined by the position of the marker (e.g., cannula) in space, and the angle for that sum is the angle of the marker (e.g., cannula).

As an alternative to the image mask, the sagittal and coronal image data can be processed so that points in the arrays with signal intensity less than a given threshold are assigned a value of 0, and points above the threshold are given a value of 1. Next, a linear regression is performed on the points in the image to obtain the line the cannula lies on in each projection. The first and last points along this line having a value of 1 define the marker (e.g., cannula) in space.

With respect to the 3D scan methodology, first a 3D scan of the region encompassing the marker (e.g., targeting cannula.) is taken and/or obtained. Next, the image array is "padded" by adding zeros to the left, right, top, bottom, front, and back of the image arrays so that an image recognition mask can be effectively applied to the edges. These images are processed so that points in the arrays with signal intensity less than a given threshold are assigned a value of 0, and points above the threshold are given a value of 1. Next, a image recognition mask A (an a*b*c array) that traces out the shape of the targeting cannula for a given angle is applied to the images as follows:

a. Starting at the point (0,0,0) in the image I (which is an m by n by o array) calculate the sum of the values of $I(x,y,z)*A(x,y,z)$ for x:[0,a], y:[0,b], z:[0,c].
b. Repeat at points (1,0,0), (2,0,0), . . . , (m−a,0,0) in A.
c. Repeat in rows 1, 2, . . . , n−b in A.
d. Repeat in planes 1, 2, . . . , o−c in A.

After these steps are completed for a filtering mask at a given angle, repeat with a mask where the cannula is to be recognized at a different angle. Repeat for all desired angles (typically for all reasonably possible angles). The point where a mask created the highest summation at a given angle is recognized as the lower left front corner of the rectangular solid defined by the position of the marker (e.g., cannula) in space, and the angle for that sum is the angle of the marker (e.g., cannula).

As an alternative to the image mask for the 3D scan analysis, these images can be processed so that points in the arrays with signal intensity less than a given threshold are assigned a value of 0, and points above the threshold are given a value of 1. Next, a linear regression is performed on the points in the image to obtain the line the marker (e.g., cannula) lies in. The first and last points along this line having a value of 1 define the marker (e.g., cannula) in space.

If the elongate marker is a targeting cannula that is used with a multi-lumen insert that attaches to the mount 15 and/or if the targeting cannula itself includes multiple lumens, additional information about the path defined by each or more than one lumen can be projected and serially or concurrently displayed on the display, typically a display at a clinician imaging interface workstation.

Figure 10A:
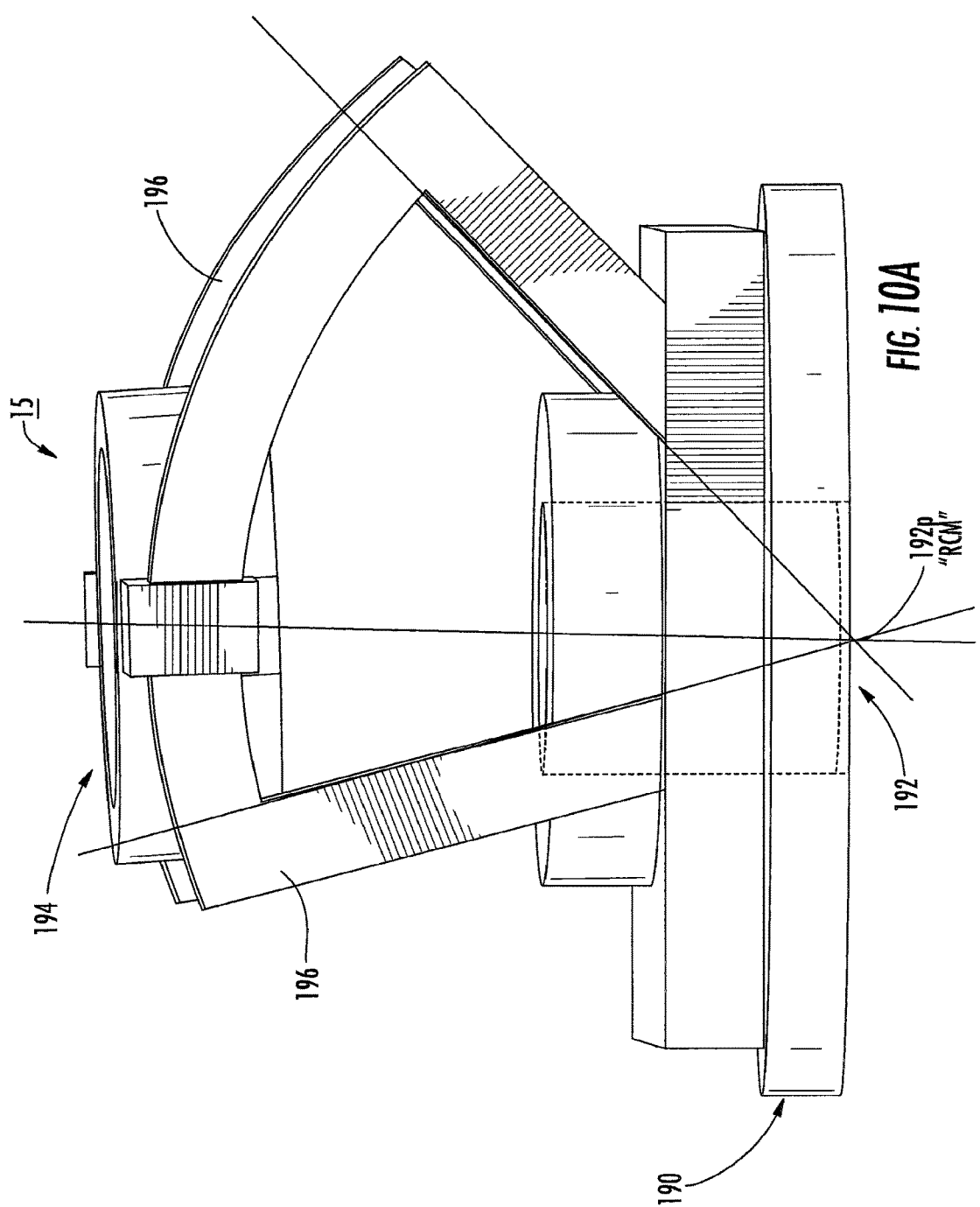
FIG. 10A is a greatly enlarged side view of a frameless mount according to embodiments of the invention.

FIG. 10A illustrates an example of a frameless mount 15. As shown, the mount 15 includes a base plate 190 with an open access lumen 192 that can be affixed to a patient, such as to a skull over a burr hole. The mount 15 also includes a port 194 configured to hold the targeting cannula 20 or multi-lumen insert 300 (FIG. 12A), or both (serially). As shown, the mount 15 also includes upwardly projecting arms 196 that hold the port 194. The port 194 can slide (translate) forward and rearward over a curvilinear path defined by the arms 196. The arms 196 can translate and rotate with respect to the base 190. In the embodiment shown, the arms 196 attach to a rotatable platform 198 that is attached to the base 190.

FIGS. 10B-10E illustrate exemplary user adjustment members 198r, 196t. The rotation adjustment member 198r and the translation adjustment member 196t can each comprise at least two members as shown in FIG. 10C, to allow for ease of access to the members when mounted and the patient resides in the bore of a magnet associated with an MRI scanner (and/or accommodate either right or left handed users). The translation adjustment member can adjust pitch (tilt or swivel) while the rotation adjustment member 198r allows the rotation of the receiving port 194.

In some embodiments, one or both of the adjustment members 198r, 196t can be in communication with non-ferromagnetic flexible drive shafts or cables 198d, 196d (FIGS. 10B, 10D) that may extend a suitable distance (e.g., between about 1-4 feet) to allow a clinician to adjust the settings on the mount 15 without moving the patient and from a position outside the bore of the magnet. In other embodiments, the flexible drive shafts can extend a longer distance to an automated control module associated with the Control Circuit 10C (FIG. 8) that can automatically adjust the mount trajectory using the input members 198r, 196t, based on an electronic analysis of a target trajectory in MRI data.

In some embodiments, the location/trajectory of the mount 15 can be adjusted manually or via a drive (manual, mechanical, electrical, piezoelectric, pneumatic, hydraulic, etc.) and manually or automatically and locked in the final desired orientation. If drive cables 198d, 196d and electrical connections are used, these may be removable once the mount 15 is aligned in the desired position. The mount 15 may have calibrations (markings) and/or optical encoders, piezoelectric encoders, etc. to determine the settings of the mount and extent of adjustment carried out. The sensors or position encoders can provide a feedback loop that can be used if automated features in positional adjustment are used. Also, once the (head) mount is locked, these encoders can provide data to a monitoring system to monitor the locked position and alert of any unplanned changes to the head-mount settings during a procedure.

Figure 10B:
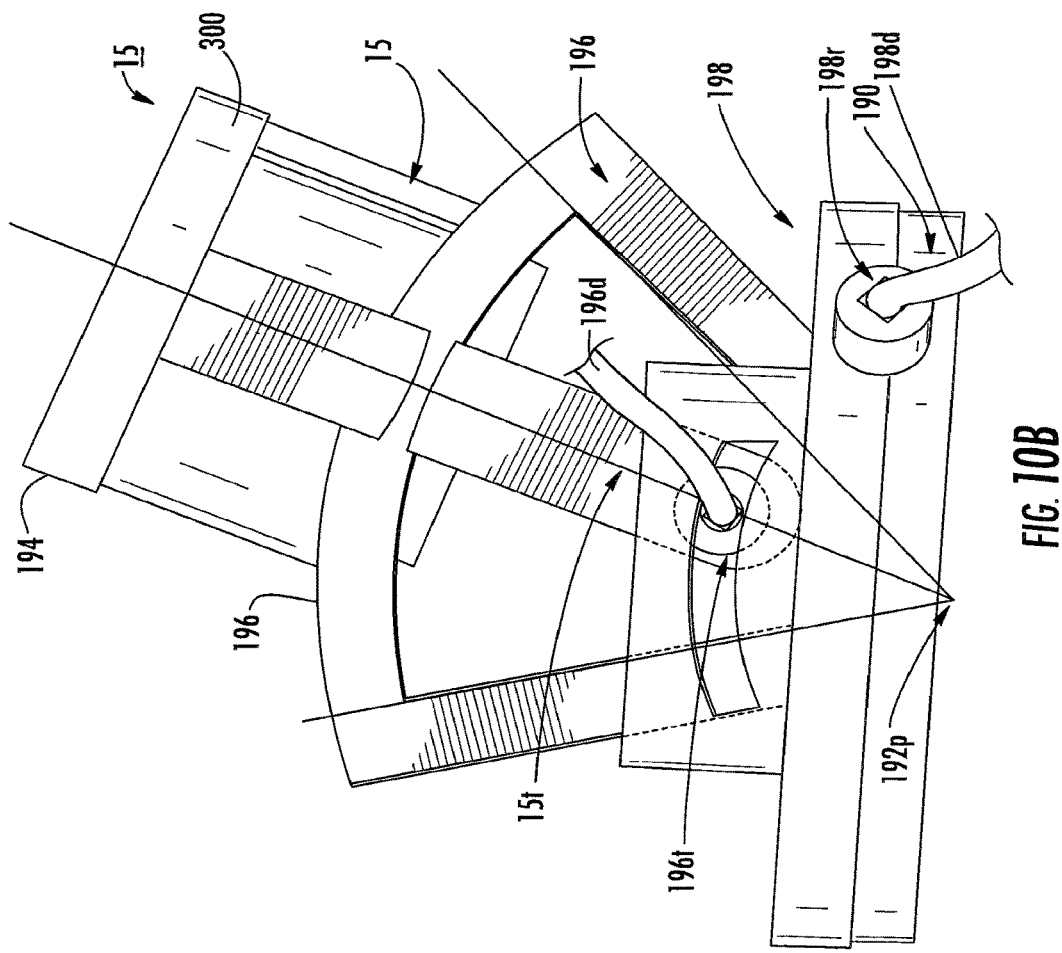
FIG. 10B is a greatly enlarged side view of a frameless mount similar to that shown in FIG. 10A, illustrating pitch and rotation adjustment members according to embodiments of the invention.
Figure 10E:
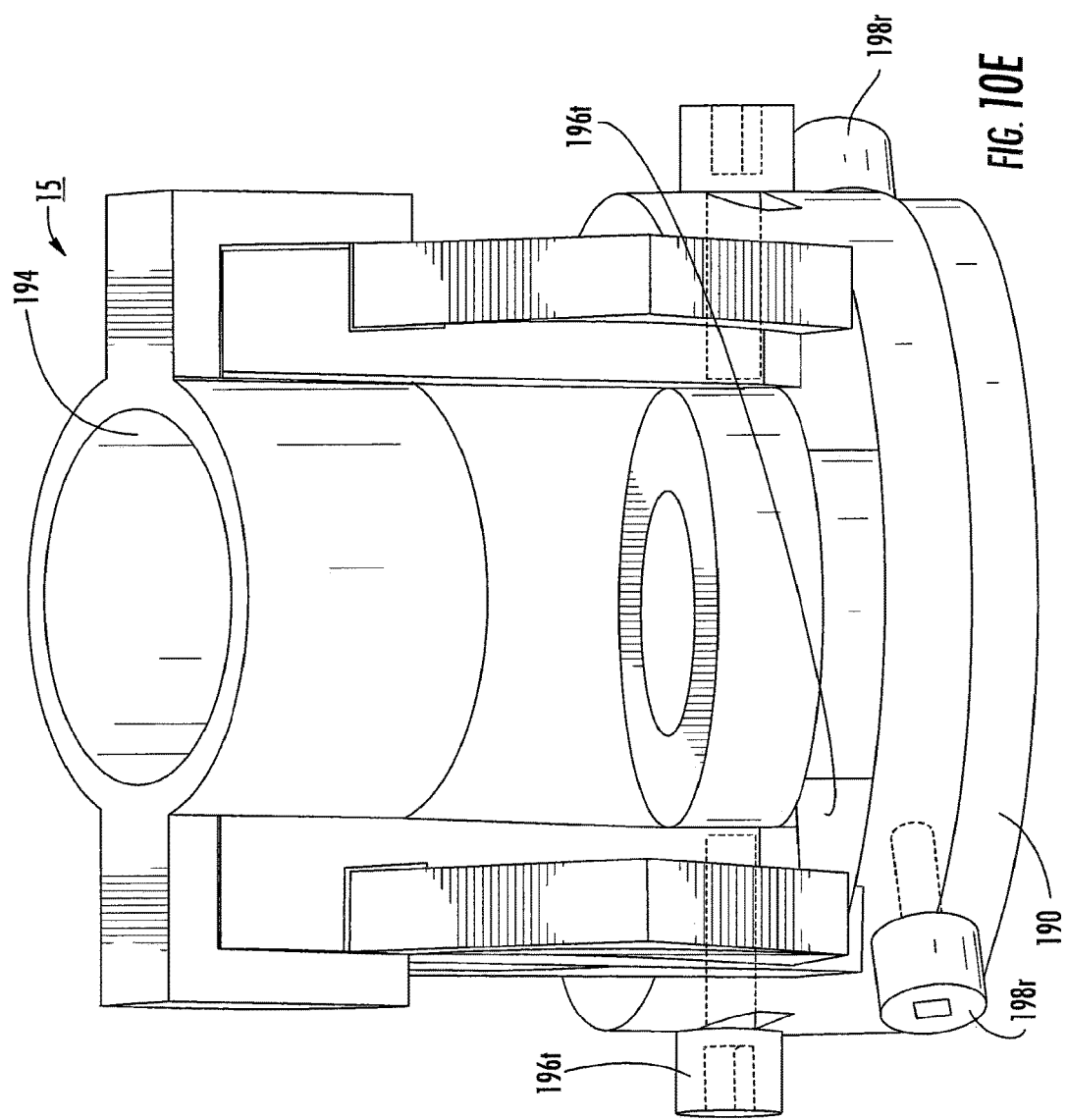
FIG. 10E is a greatly enlarged front view of a different configuration of the device shown in FIG. 10B according to embodiments of the invention.

FIG. 10B illustrates that the multilumen insert 300 can be integral with the mount 15. As shown, the insert 300 can attach directly to the mount arms 196. In other embodiments, as shown in FIG. 10E, the insert 300, if used, can be a separate component or releasably attached to a holding member defining the mount port 194.

FIGS. 11A-11F illustrate different configurations that the mount 15 can take to define a desired access path trajectory extending from the port 194 down and through the RCM (pivot zone) 192p into a patient.

Where the mount 15 is configured as a head mount, the fixture is mounted to the patient's skull, typically threaded or friction fit to a rigid (threaded) burr insert or ring over the burr hole, to provide a stable frame to advance surgical devices, leads, etc. in the brain. The frameless headmount 15 may be a fixture with two or more degrees of freedom (rotate and translate/swivel) around the RCM. This RCM may be between about ±3 cm from the surface of the skull.

The frameless headmount 15 allows the operator to align the access path trajectory to an internal target site, such that the interventional/surgical device/lead, therapy, etc. will be delivered to the target site following the desired trajectory thorough the cranial tissue. This trajectory goes through the RCM point.

In some embodiments, after a burr hole is drilled and the frameless headmount is fixed to (in or on) the patient's skull, the first step is to register the position of the headmount, and the trajectory the interventional/surgical device/lead will follow if advanced through the headmount. This may be done by multiple ways. For example, the frameless head-mount may have active or passive MRI/CT/ultrasound/optical fiducial markers, tracking coils for MRI, which can allow the operator to register the position of the frameless headmount and the RCM point at any given time based on MRI/CT/ultrasound/optical images. The position registration can be determined by analyzing image data obtained in any suitable ways, such as, but not limited to, projection images in a plurality (2 or more) of substantially orthogonal planes, etc., or 3D volumetric scans as described above.

As shown in FIGS. 12A-12E and 13A-13C, the mount 15 (frameless or framed) may hold a multilumen insert 300, through which the cannula 20, the probe 30 and the lead 35 may be advanced. Fiducial markers may optionally be incorporated as appropriate on the mount 15 and/or the multilumen insert 300 to facilitate registration of the orientation of the lumens 305 of the multilumen insert 300. One or more of the lumens 305 may hold a fluid-filled tube, i.e., 201 (FIG. 15A) or include a fluid-filled channel 1305 (FIG. 10D) that makes the lumen MRI visible. Each or some of the lumens 305, alone or with elongate inserts, may be in communication or include MRI imaging coils (not shown). The insert 300 can include Uncial markers that allow a clinician to visually denote which lumen provides the desired trajectory (particularly relevant for the outer lumens 305p (FIG. 12A) rather than the medial lumen 305c).

The fiducial markers referenced herein may be provided by tracking coils, imaging coils or even, for devices having segments with fluid filled or MRI contrast material, configuring those segments or lumens with a different MRI visible shape and/or axial starting location (such as, for example, to be arranged as longer to shorter in a defined perimeter direction), or combinations thereof.

FIG. 14 illustrates a targeting cannula 20 with an open through lumen 25 that is sized and configured to allow a probe 30 (typically with an external sheath 34, FIG. 2C) to slidably advance therethrough. This cannula 20 may reside in the port 194 without the use of a multi-lumen insert 300 (e.g., directly or with a fitting sleeve or collar, and the like). As shown, the cannula 20 can also include at least one closed axially extending fluid-filled hollow lumen 23 that surrounds the lumen 25. The closed fluid lumen 23 can include at least one fluid (typically liquid) fill port 23p that can be used to inflate the lumen 23 before, during and/or after the lumen 23 is placed in the cannula 20. The fluid lumen 23 can be defined by a tubular elastomeric body or may be defined by a channel formed in the cannula 20. The cannula 20 can also include one or more grooves 27 to hold an MRI imaging coil. As also shown, the cannula 20 can include at least one substantially spherical fluid-filled end portion $20s_1$ that may reside a distance of between about 5-15 cm above the RCM point. The cannula 20 may also include a second fluid-filled substantially spherical end portion $20s_2$ typically residing proximate the RCM point. The spherical end portions $20s_1$, $20s_2$ may be a part of the lumen 23 or may be discrete and separate from the lumen 23.

In some embodiments, the MRI coil can reside on the outside of the cannula 20, and may be a loop MRI coil. The MRI coil can enhance the MRI signal in the fluid, thereby allowing the operator to visualize the fluid filled sections very clearly. If required, another fluid filled tube may be inserted in the through lumen during the primary registration and alignment steps. Once the alignment is done, this tube is removed and replaced with a multipurpose probe 30 with delivery sheath 34.

In some embodiments, the targeting cannula 20, the multipurpose probe 30 and/or delivery sheath 34 can be used to provide additional signal from the contrast filled fluid in the targeting cannula 20. This may be used in place of the MRI coil built on the outer sides of the targeting cannula shown in FIG. 14. It is also noted that, different designs can be incorporated so that the probe lumen of the cannula 20 is at locations other than that at the central trajectory, i.e., it may be parallel to the central trajectory or at controlled angle to the central trajectory.

FIG. 15A illustrates a targeting cannula 20 that is configured to reside in a lumen 305 of the insert 300. This targeting cannula 20 can include axially spaced apart, substantially spherical fluid-filled segments $20s_1$, $20s_2$. In this embodiment, the segments may reside above the lumen 305. A fluid-filled lower leg 201 can reside in the lumen 305 and extend to the RCM point 192p. The fluid can comprise an MRI contrast-enhancing liquid that can be used to define the trajectory of the mount 15 when residing in a lumen 305. FIG. 15B illustrates that the targeting cannula 20 can include at least one side arm 20a that can reside in a different lumen 305 of the insert 300. The side arm 20a can also include a fluid filled channel and may optionally include axially spaced apart substantially spherical segments. The targeting cannula (contrast medium filled) side arm 20a can provide data that can allow identification of a precise orientation of the multilumen insert 300.

In the embodiments shown in FIGS. 15A and 15B, the fluid/contrast filled segments may be relatively thin, such as between about 0.5 mm to about 4 mm, typically between about 1 mm to about 3 mm. The segments can delineate the trajectory the interventional device 35 and multipurpose probe 30 (with delivery sheath 34) will take with the alignment of the head mount 15. The contrast-filled spherical sections and the straight thin contrast-filled sections of the targeting cannula may provide the imaging signature that can be used for finding the location of the targeting cannula in the 3D MRI space and provide visual confirmation of the trajectory of the device in the tissue. The targeting cannula 20 can have one or more MRI coils (loop, loopless, solenoid, etc. incorporated in the design). Also, tracking coils can be optionally incorporated at various sections of the targeting cannula to provide 3D location information in MRI space.

FIGS. 16A and 16B illustrate that, where a multi-lumen insert 300 is used, images can be displayed with lines that indicate the trajectory $300t_1$-$300t_4$ (where four lumens are used) followed by each lumen 305 of the multilumen insert from the lumen 305 to the target site $1000t$. FIG. 16A corresponds to projections in an oblique coronal/sagittal image while FIG. 16B illustrates the corresponding end points of the lines in an axial/oblique scan. The targeting cannula 20 may be modified as shown in FIG. 15 and/or fiducial markers may be incorporated on the multi-lumen insert 300 and/or mount 15.

Figure 17A:
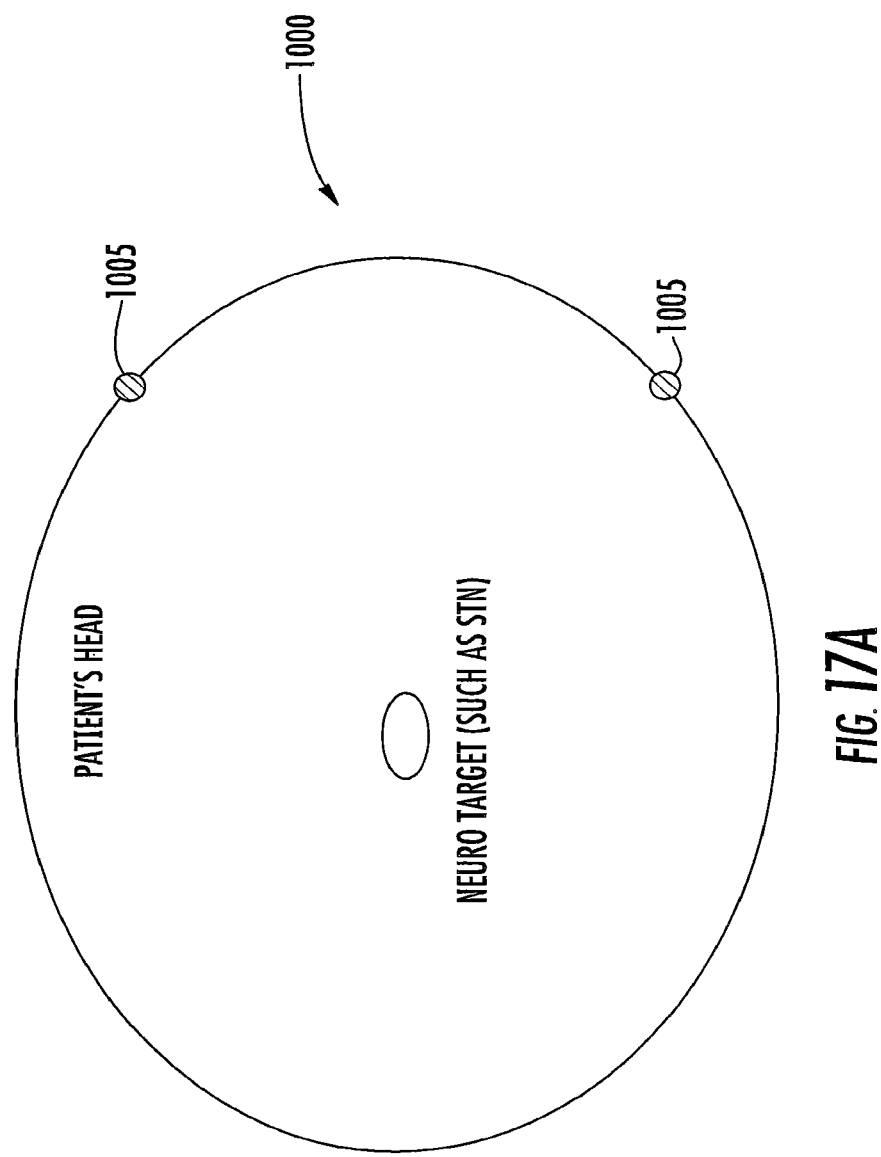
FIGS. 17A-17C are schematic illustrations of steps that can be taken to place a site-specific interventional device or therapy according to some embodiments of the invention.
Figure 17B:
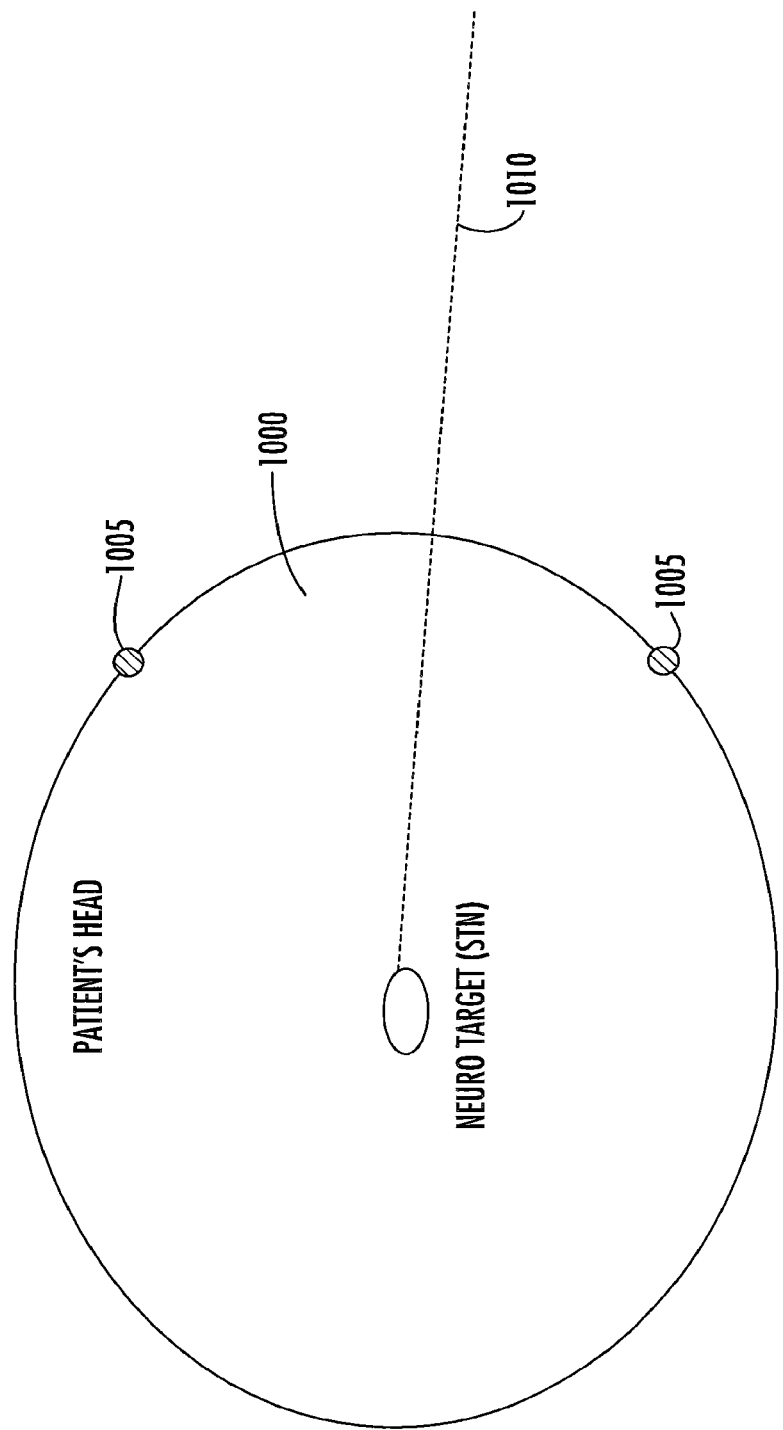
Figure 17C:
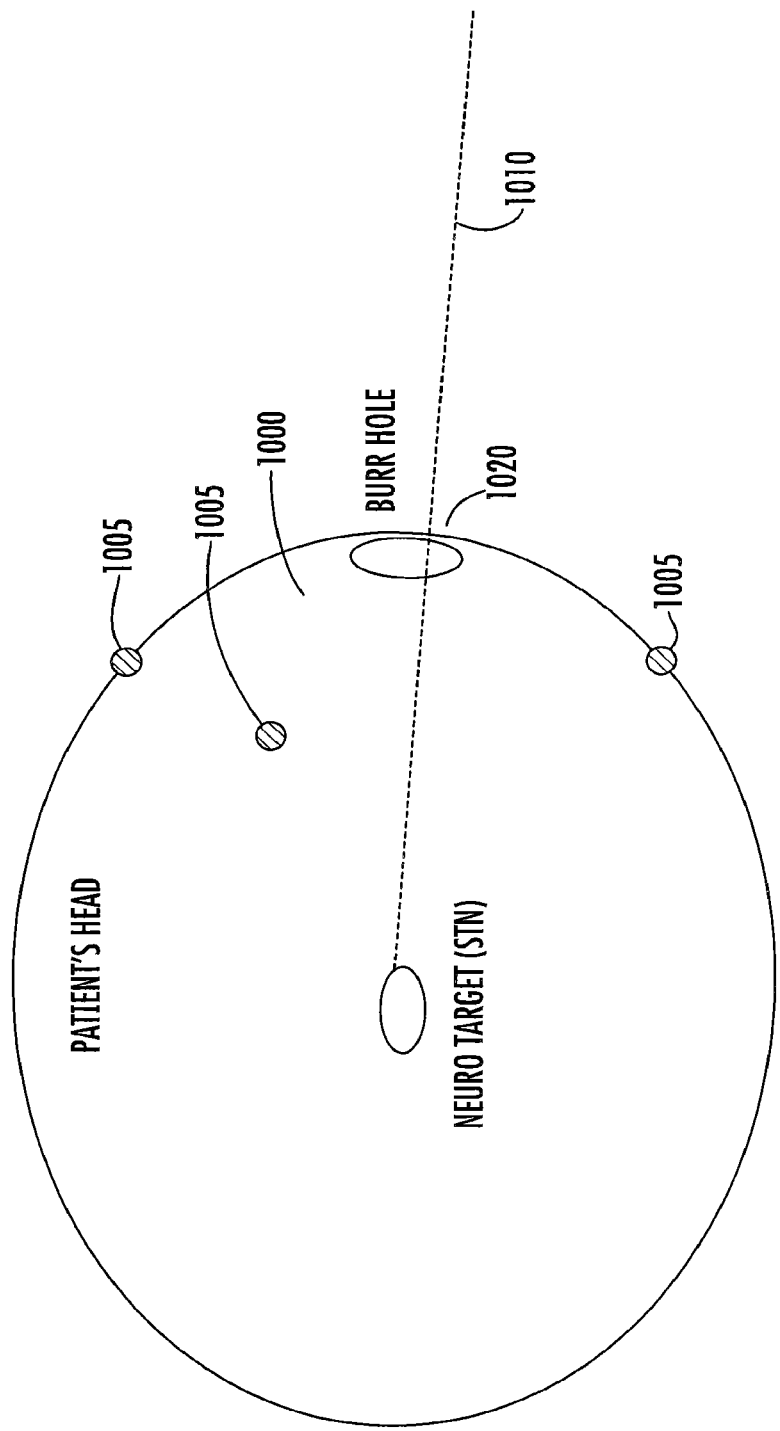
Figure 18A:
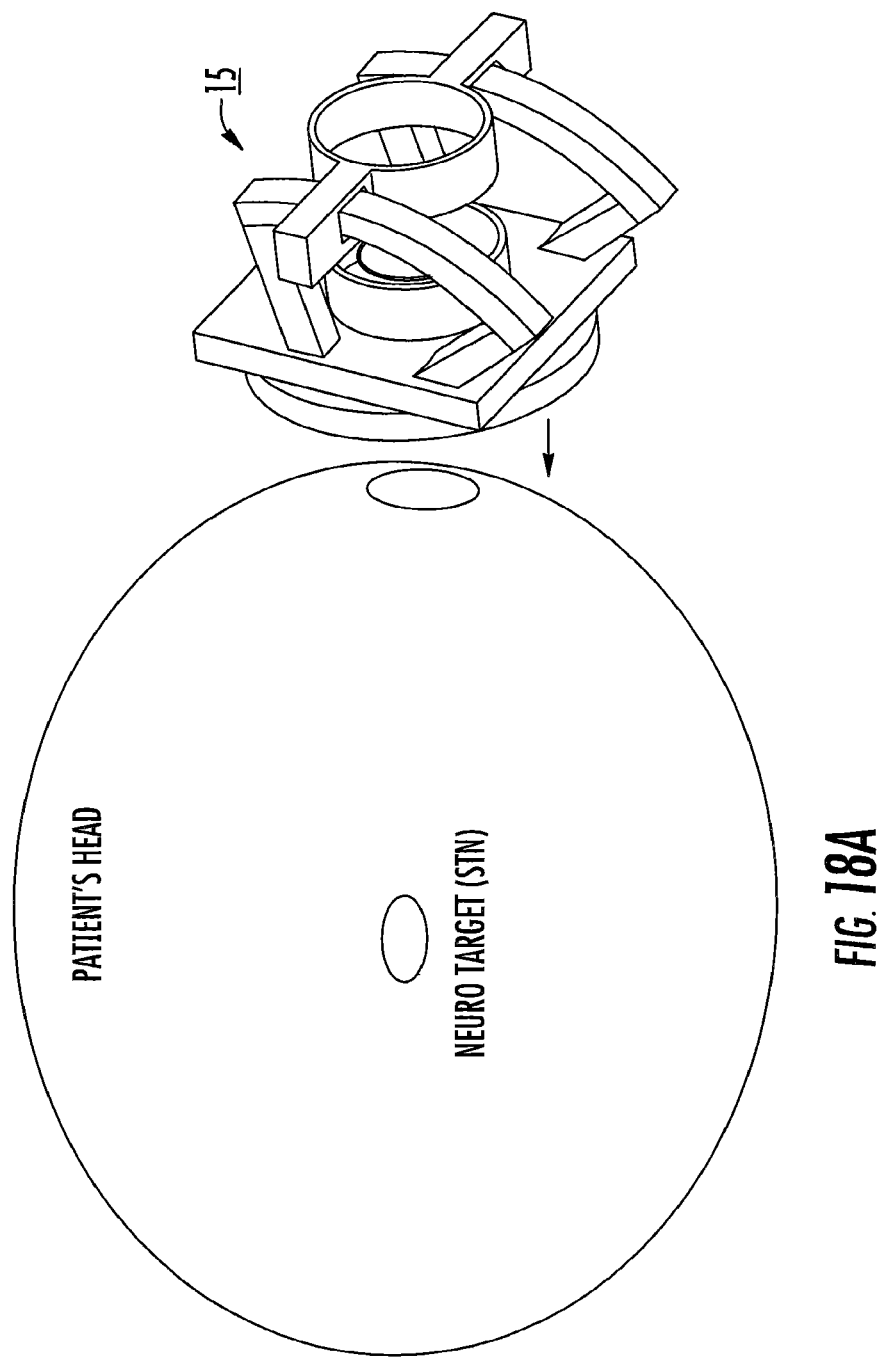

FIGS. 17A-17C illustrate steps associated with a typical surgical procedure.

1—Place the patient in an MR scanner and obtain MR images of the patient's head 1000 that visualize the patient's skull, brain, fiducial markers 1005 and ROI (region of interest or target therapeutic site). The MR images can include volumetric high-resolution images of the brain.

2—To identify the target ROI, certain known anatomical landmarks can be used, i.e., reference to the AC, PC and MCP points (brain atlases give the location of different anatomies in the brain with respect to these point) and other anatomical landmarks.

3—The location of the burr hole may optionally be determined manually by placing fiducial markers on the surface of the head or programmatically by projecting the location in an image.

4—Image in the planned plane of trajectory 1010 and confirm that the trajectory is viable, i.e., that no complications with anatomically sensitive areas should occur.

5—Optically or manually mark one or more desired locations to drill the burr hole.

6—Drill the burr or patient access hole.

7—Fix the burr hole ring (where used).

As shown in FIGS. 18A-18E, the following sequence can then be carried out.

8—Fix the Frameless or frame based head mount.

9—Fit the targeting cannula.

10—Obtain localization scan to determine/register the location of the targeting cannula, in direct orientation of the headmount.

11—Electronically derive the settings to which the headmount should be adjusted so that the targeting cannula is in the desired trajectory plane.

12—Confirm this by imaging in one or more planes orthogonal to the desired trajectory plane.

13A—If the targeting cannula is so configured (as shown in FIGS. 18D and 18E) advance the multipurpose probe and delivery sheath through the targeting cannula.

13B—If the targeting cannula will not allow that; remove the targeting cannula and use the central lumen of the multi-lumen insert—advance the multipurpose probe and delivery sheath in the central lumen of the multilumen insert. Also, the targeting cannula can be configured to fit in the central lumen of the multilumen insert.

14—Advance the multipurpose probe and delivery sheath, when imaging in the trajectory plane, monitoring that the multipurpose probe is in that imaging plane and it will reach the target accurately.

15—On positioning the multipurpose probe in the target site, obtain high-resolution images of the anatomy, deliver a stimulation pulse, and optionally measure EEG signal with the multipurpose probe.

16—If multipurpose probe and delivery sheath are at the desired target, leave the sheath in place and remove the multipurpose probe; this sheath will now act as the delivery cannula for the implantable lead.

17—If the multipurpose probe and delivery sheath are not at the desired/optimal location, decide where the multipurpose probe and delivery sheath need to be. Adjust the headmount accordingly or use another appropriate lumen of the multi-lumen insert and readvance the multipurpose probe and delivery sheath.

18—Once the multipurpose probe and delivery sheath are at the desired location, remove the multipurpose probe and leave the delivery sheath in place.

19—Advance the lead to the target location using the sheath as a guide.

20—Confirm the location of the lead by reviewing an image, acoustic recording and/or stimulation.

21—Remove the sheath, leaving the lead in place.

It is contemplated that embodiments of the invention can provide an integrated system that may allow the physician to place the interventional device/leads accurately and in short duration of time. In some embodiments, once the burr hole is drilled, and the frameless head mount is fixed to the skull; the head mount is oriented such that the interventional device advanced using the frameless headmount follows the desired trajectory and reaches the target as planned in preoperative setup imaging plans. As described herein, the system 10 can employ hardware and software components to facilitate an automated or semiautomated operation to carry out this objective.

Figure 19:
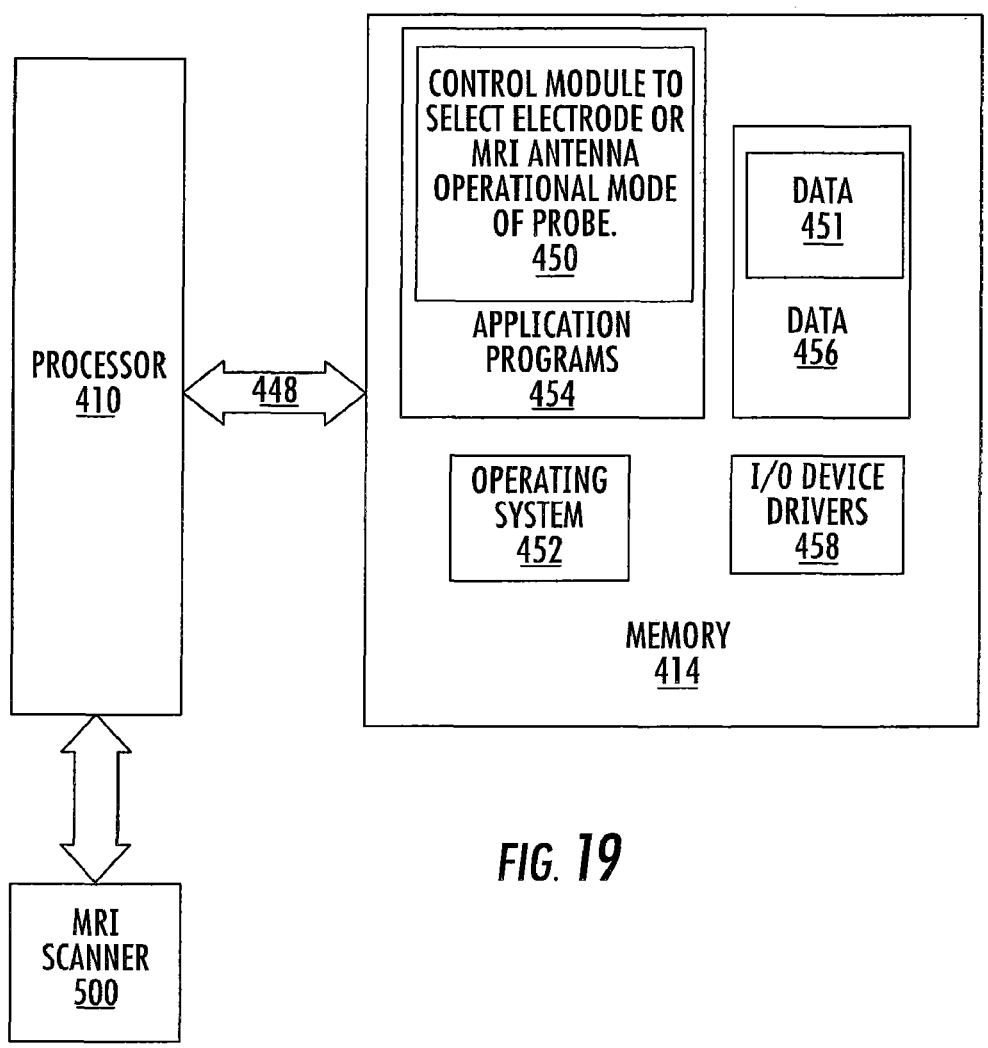
FIGS. 19 and 20 are block diagrams of data processing systems according to embodiments of the present invention.
Figure 20:
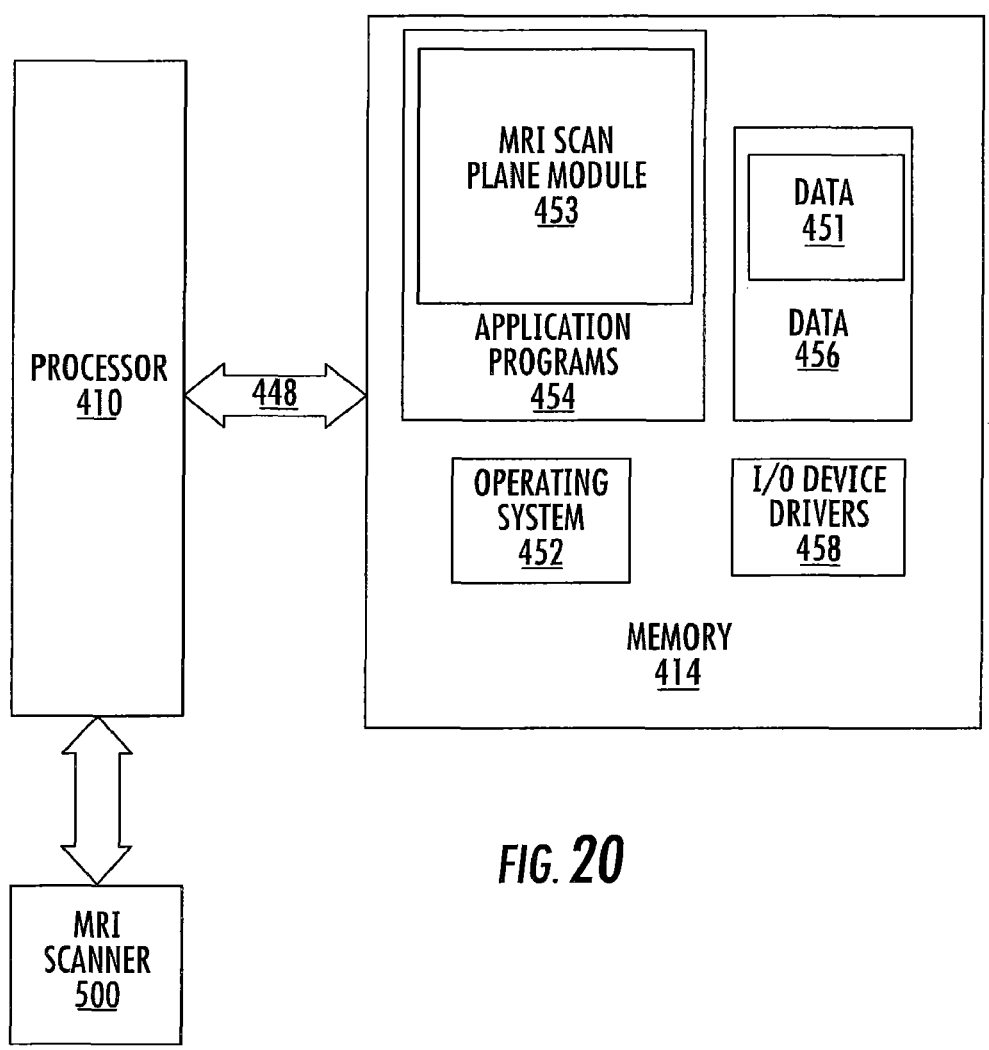

In some embodiments, the system 10 can include one or more software modules that can automate or carry out aspects of the invention, as shown for example, in FIGS. 19 and 20.

The modules can include data processing systems and computer program products in accordance with embodiments of the present invention. The data processing systems may be incorporated in a digital signal processor in any suitable device. The processor 410 communicates with the memory 414 via an address/data bus 448. The processor 410 can be any commercially available or custom microprocessor. The memory 414 is representative of the overall hierarchy of memory devices containing the software and data used to implement the functionality of the data processing system. The memory 414 can include, but is not limited to, the following types of devices: cache, ROM, PROM, EPROM, EEPROM, flash memory, SRAM, and DRAM.

As shown in FIGS. 19 and 20, the memory 414 may include several categories of software and data used in the data processing system: the operating system 452; the application programs 454; the input/output (I/O) device drivers 458; and data 456. FIG. 19 illustrates the MRI Antenna operation or Electrode Operation Module 450 and FIG. 20 illustrates the automated MRI scan plane determination module 453 (with optional mount setting/adjustment module).

As will be appreciated by those of skill in the art, the operating systems 452 may be any operating system suitable for use with a data processing system, such as OS/2, AIX, DOS, OS/390 or System390 from International Business Machines Corporation, Armonk, N.Y., Windows CE, Windows NT, Windows95, Windows98, Windows2000 or other Windows versions from Microsoft Corporation, Redmond, Wash., Unix or Linux or FreeBSD, Palm OS from Palm, Inc., Mac OS from Apple Computer, LabView, or proprietary operating systems. The I/O device drivers 458 typically include software routines accessed through the operating system 452 by the application programs 454 to communicate with devices such as I/O data port(s), data storage 456 and certain memory 414 components. The application programs 454 are illustrative of the programs that implement the various features of the data processing system and can include at least one application, which supports operations according to embodiments of the present invention. Finally, the data 456 represents the static and dynamic data used by the application programs 454, the operating system 452, the I/O device drivers 458, and other software programs that may reside in the memory 414.

While the present invention is illustrated, for example, with reference to the Modules 450, 453 being an application program in FIGS. 19, 20, as will be appreciated by those of skill in the art, other configurations may also be utilized while still benefiting from the teachings of the present invention. For example, the Modules 450, 453 and/or may also be incorporated into the operating system 452, the I/O device drivers 458 or other such logical division of the data processing system. Thus, the present invention should not be construed as limited to the configuration of FIGS. 19 and 20 which are intended to encompass any configuration capable of carrying out the operations described herein. Further, one or more of modules, i.e., Module 450, 453 can communicate with or be incorporated into other components, such as an MRI scanner 500 or MRI scanner interface.

The I/O data port can be used to transfer information between the data processing system, the MRI scanner, a display associated with a clinician workstation, the mount, cannula, and the probe (such as, for example MRI imaging data from the MRI imaging coils) and the stimulation lead and another computer system or a network (e.g., the Internet) or to other devices controlled by the processor. These components may be conventional components such as those used in many conventional data processing systems, which may be configured in accordance with the present invention to operate as described herein.

With respect to certain embodiments, the computer-readable program code can include computer readable program code that controllably engages a first or second operational mode for a MRI compatible stimulation probe with at least one electrode and an MRI antenna. The first operational mode having a first transmission path connecting the MRI antenna with an MRI scanner and decoupling the electrodes during MRI operation and the second operational mode having a second transmission path connecting the electrodes with a stimulation or recording source during electrical stimulation or recording.

The computer readable program code may be configured to time the selection of the second operational mode to occur proximate in time but after an MRI signal acquisition by the MRI antenna in the first operational mode. The computer readable program code may be configured to obtain microrecordings of local tissue in substantially real time proximate in time to an MRI signal acquisition by the MRI antenna in the first operational mode. The computer readable program code may be configured to obtain a plurality of MRI signals of local neural tissue proximate the MRI antenna in substantially real time, and then obtain a plurality of microrecordings of the local neural tissue to allow a clinician to track placement of the probe using both MRI data and audio data.

The flowcharts and block diagrams of certain of the figures herein illustrate the architecture, functionality, and operation of possible implementations of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

The documents incorporated by reference are done so to describe the state of the art but are not to be used to narrow the interpretation of the terms or components in the claims.

In the drawings and specification, there have been disclosed embodiments of the invention and, although specific terms are employed, they are used in a generic and descriptive sense only and not for purposes of limitation, the scope of the invention being set forth in the following claims. Thus, the foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A localization and/or guidance system for facilitating placement of an interventional device in vivo, comprising:
   a base plate adapted to be affixed to a skull of a patient;
   a mount attached to the base plate, the mount holding a multi-lumen member that, in use, is adapted to be external to the skull of the patient, wherein the multi-lumen member comprises a plurality of longitudinally extending lumens, wherein the plurality of longitudinally extending lumens includes a center lumen and a plurality of perimeter lumens positioned about the center lumen and the plurality of longitudinally extending lumens are parallel and have a common length and width; and at least one tube comprising image contrast fluid sized and configured to be slidably received in at least a plurality of lumens of the plurality of longitudinally extending lumens, wherein the system is configured to segment Magnetic Resonance (MR) image data to locate and orient the lumens to define trajectories that extend into a brain of the patient in three-dimensional (3D) Magnetic Resonance Image (MRI) space.

2. The system of claim 1, further comprising a pair of arcuate laterally spaced apart arms that hold the mount therebetween and above the base plate, wherein the arcuate arms have a common length and are symmetrical with the length extending beyond each side of a patient access aperture in the base plate.

3. The system of claim 1, wherein the plurality of longitudinally extending lumens are provided as five lumens.

4. The system of claim 1, wherein the plurality of longitudinally extending lumens comprise a center lumen with adjacent lumens residing spaced apart about the center lumen, and wherein the at least one tube comprising image contrast fluid is configured so that the image contrast fluid extends a length sufficient to reside inside and external to the longitudinally extending lumen.

5. The system of claim 1, wherein the mount is configured to serially and interchangeably hold an elongate guide and the multi-lumen member.

6. The system of claim 5, wherein the elongate guide comprises a longitudinally extending through channel that can align with a patient access aperture of the base plate for slidably receiving an intrabody device.

7. A localization and/or guidance system for facilitating placement of an interventional device in vivo, comprising:
   a base plate adapted to be affixed to a skull of a patient;
   a mount attached to the base plate, the mount holding a multi-lumen member that, in use, is adapted to be external to the skull of the patient, wherein the multi-lumen member comprises a plurality of longitudinally extending lumens;
   at least one tube comprising image contrast fluid sized and configured to be slidably received in at least a plurality of lumens of the plurality of longitudinally extending lumens; and
   a pair of arcuate laterally spaced apart arms that hold the mount therebetween and above the base plate, wherein the arcuate arms have a common length and are symmetrical with the length extending beyond each side of a patient access aperture in the base plate,
   wherein the mount is slidably supported by the arms and the mount slidably travels forward and rearward over a curvilinear path defined by the arms, wherein each of the arms is attached to the base plate by first and second leg portions, and wherein lower ends of the first and second leg portions are attached to the base plate at respective locations that are spaced apart from and outside the patient access aperture.

8. A localization and/or guidance system for facilitating placement of an interventional device in vivo, comprising:
   a base plate adapted to be affixed to a skull of a patient; and
   a mount attached to the base plate, the mount comprising a port configured to releasably hold a multi-lumen member above and outside the patient, wherein the multi-lumen member comprises a plurality of longitudinally extending lumens,
   wherein the plurality of longitudinally extending lumens includes a center lumen and a plurality of perimeter lumens positioned about the center lumen, wherein the plurality of longitudinally extending lumens are parallel, have a common length and width and a plurality of the lumens enclose image contrast fluid, and wherein, the system is configured to segment Magnetic Resonance (MR) image data to locate and orient the lumens to define trajectories in three-dimensional (3D) Magnetic Resonance Image (MRI) space that extend into a body of the patient.

9. A localization and/or guidance system for facilitating placement of an interventional device in vivo, comprising:
   a base plate adapted to be affixed to a skull of a patient;
   a mount attached to the base plate, the mount holding a multi-lumen member that, in use, is adapted to be external to the skull of the patient, wherein the multi-lumen member comprises a plurality of longitudinally extending lumens;
   at least one tube comprising image contrast fluid sized and configured to be slidably received in at least a plurality of lumens of the plurality of longitudinally extending lumens,
   wherein the base plate defines a patient access aperture, wherein the system comprises only a single pair of spaced apart upwardly extending arcuate arms attached to the base plate, wherein the arms are attached to the base plate by front and back leg portions that, when viewed from a lateral direction, extend upward from the base plate so as to rise up a distance from the base plate before merging into the arcuate arms, wherein lower ends of the front and back leg portions are attached to the base plate at locations that are spaced apart from and outside the patient access aperture, and wherein, when viewed from the lateral direction, the front and back leg portions define an open space therebetween to thereby provide a side viewing window, wherein the side viewing window and the base plate cooperate to define an open path to the patient access aperture to allow a user to view the patient access aperture and thereby a patient access entry location of the patient, through the side viewing window, and wherein the multi-lumen member is held by the arms above the base plate and is configured to be visible through the side viewing window.

10. A localization and/or guidance system for facilitating placement of an interventional device in vivo, comprising:
   a base plate adapted to be affixed to a skull of a patient; and
   a mount attached to the base plate, the mount comprising a port configured to releasably hold a multi-lumen member, wherein the multi-lumen member comprises a plurality of longitudinally extending lumens,
   wherein the mount is configured to serially and interchangeably hold an elongate guide and the multi-lumen member,
   wherein the elongate guide comprises an elongate body with an internal wall surrounding a longitudinally extending open channel, wherein a longitudinally extending fluid filled lumen extends adjacent the open channel over at least a major portion of a length of the elongate body to merge into a spherical lower end portion, and wherein the open channel extends through a center of the spherical lower end portion.

11. The system of claim 10, further comprising an electronic in vivo access path trajectory determination circuit, the circuit comprising a non-transitory computer readable storage medium having computer readable program code embodied in the medium, the computer-readable program code comprising:
computer readable program code configured to electronically determine coordinates of a position in three-dimensional (3-D) image space using the multi-lumen member of the system which remains external of the patient based on pixels or voxels with increased signal to noise ratio (SNR).

12. A localization and/or guidance system for facilitating placement of an interventional device in vivo, comprising:
a base plate adapted to be affixed to a skull of a patient;
a mount attached to the base plate, the mount holding a multi-lumen member that, in use, is adapted to be external to the skull of the patient, wherein the multi-lumen member comprises a plurality of longitudinally extending lumens;
at least one tube comprising image contrast fluid sized and configured to be slidably received in at least a plurality of lumens of the plurality of longitudinally extending lumens; and
an electronic in vivo access path trajectory determination circuit, the circuit comprising a non-transitory computer readable storage medium having computer readable program code embodied in the medium, the computer-readable program code comprising:
computer readable program code configured to electronically determine coordinates of a position in three-dimensional (3-D) image space and generate longitudinally extending parallel virtual trajectory lines that extend from a location outside the patient to a target intrabody site and that correspond to lumens of the multi-lumen member that indicate projected trajectories to the target intrabody site using the multi-lumen member of the system which remains external of the patient based on pixels or voxels with increased signal to noise ratio (SNR).

13. A localization and/or guidance system comprising:
a base adapted to be affixed to a skull of a patient; and
a mount attached to the base, the mount comprising a port configured to releasably serially and interchangeably hold (a) a multi-lumen member, wherein the multi-lumen member comprises a plurality of parallel longitudinally extending lumens and (b) an elongate guide, wherein the elongate guide comprises at least one longitudinally extending through channel that can align with a patient access aperture of the base for slidably receiving an intrabody device,
wherein the multi-lumen member has a body with a circumferentially extending planar upper surface, and wherein each of the plurality of longitudinally extending lumens has an upper end defined by the planar upper surface and is flush with the planar upper surface, wherein the plurality of longitudinally extending lumens are arranged as a center lumen and a plurality of adjacently positioned outer lumens that reside radially outward a distance from the center lumen and have a common length and common diameter, and wherein a plurality of the lumens comprise image contrast fluid.

14. The system of claim 13, wherein the plurality of longitudinally extending lumens comprise five lumens.

15. The system of claim 13, wherein the mount comprises first and second arcuate arms each of which are attached to first and second leg portions coupled to the base, wherein the arms have a common length and are symmetrical with the length extending beyond each side of a patient access aperture in the base, wherein the mount is slidably supported by the arms to allow the mount to slidably travel forward and rearward over a curvilinear path defined by the arms, and wherein lower ends of the first and second leg portions are attached to the base at locations that are spaced apart from and outside the patient access aperture.

16. A trajectory guide system for a Magnetic Resonance Image (MRI) surgical navigation system, comprising:
a mount sized and configured to attach to a skull of a patient; and
a targeting member held by the mount, wherein the targeting member comprises a plurality of parallel longitudinally extending lumens that are external to the patient, and wherein the mount cooperates with the targeting member to adjust an angular orientation of the lumens relative to a target intrabody site, wherein the plurality of longitudinally extending lumens includes a center lumen and a plurality of peripheral lumens laterally spaced apart from the center lumen, and wherein one of:
(i) at least the center lumen and a plurality of the peripheral lumens have a common length and width and comprise MRI visible image contrast fluid; or
(ii) at least the center lumen and some or all of the peripheral lumens are configured to slidably and releasably receive a fluid filled tube.

17. The system of claim 16, wherein the system includes (i) with at least the center lumen and the plurality of the peripheral lumens having a common length and width and comprise MRI visible image contrast fluid.

18. The system of claim 16, wherein the system includes (ii) with each of the center and some or all of the peripheral lumens configured to slidably and releasably receive the fluid filled tube.

19. The system of claim 16, wherein the mount comprises a frameless head mount, and wherein the system further comprises a data processing system configured to locate the targeting member which remains external of the patient based on pixels or voxels with increased signal to noise ratio (SNR) and generate images that comprise longitudinally extending parallel virtual trajectory lines corresponding to the lumens that indicate projected trajectories from a location outside the patient to the target intrabody site using the lumens.

20. The system of claim 16, further comprising a single pair of arcuate laterally spaced apart arms that hold the mount therebetween and above the base plate, wherein the arcuate arms have a common length and are symmetrical with the length extending beyond each side of a patient access aperture in the base plate, wherein the mount is slidably supported by the arms to allow the mount to slidably travel forward and rearward over a curvilinear path defined by the arms, wherein each of the arms are attached to the base plate by first and second leg portions, and wherein lower ends of the first and second leg portions are attached to the base plate at locations that are spaced apart from and outside the patient access aperture.

* * * * *

UNITED STATES PATENT AND TRADEMARK OFFICE
CERTIFICATE OF CORRECTION

| | |
|---|---|
| PATENT NO. | : 10,492,881 B2 |
| APPLICATION NO. | : 15/492747 |
| DATED | : December 3, 2019 |
| INVENTOR(S) | : Karmarkar et al. |

Page 1 of 1

It is certified that error appears in the above-identified patent and that said Letters Patent is hereby corrected as shown below:

In the Specification

Column 8, Line 4: Please correct "MR'" to read -- MRI --

Signed and Sealed this
Tenth Day of March, 2020

Andrei Iancu
*Director of the United States Patent and Trademark Office*